United States Patent
Elford et al.

(10) Patent No.: US 10,266,539 B2
(45) Date of Patent: *Apr. 23, 2019

(54) POLYMORPH OF SYK INHIBITORS

(71) Applicant: Gilead Connecticut, Inc., Foster City, CA (US)

(72) Inventors: Tim G. Elford, Sherwood Park, CA (US); Peter Chee-Chu Fung, San Mateo, CA (US); Michael Laird Hurrey, San Ramon, CA (US); Dimitrios Stefanidis, Saratoga, CA (US); Dragos Vizitiu, Edmonton (CA)

(73) Assignee: Gilead Connecticut, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,583

(22) Filed: Oct. 19, 2017

(65) Prior Publication Data

US 2018/0099971 A1   Apr. 12, 2018

Related U.S. Application Data

(60) Continuation of application No. 15/484,844, filed on Apr. 11, 2017, now abandoned, which is a division of application No. 14/446,011, filed on Jul. 29, 2014, now Pat. No. 9,657,023.

(60) Provisional application No. 61/860,197, filed on Jul. 30, 2013.

(51) Int. Cl.
   *C07D 487/04* (2006.01)
   *C07C 309/04* (2006.01)

(52) U.S. Cl.
   CPC .......... *C07D 487/04* (2013.01); *C07C 309/04* (2013.01)

(58) Field of Classification Search
   CPC .................................................. C07D 487/04
   See application file for complete search history.

(56) References Cited

U.S. PATENT DOCUMENTS

| | | |
|---|---|---|
| 5,593,997 A | 1/1997 | Dow et al. |
| 5,658,857 A | 8/1997 | Dow et al. |
| 5,783,576 A | 7/1998 | Roos et al. |
| 5,846,514 A | 12/1998 | Foster et al. |
| 6,334,997 B1 | 1/2002 | Foster et al. |
| 6,919,340 B2 | 7/2005 | Currie et al. |
| 6,919,341 B2 | 7/2005 | Paruch et al. |
| 7,160,885 B2 | 1/2007 | Currie et al. |
| 7,189,723 B2 | 3/2007 | Mitchell et al. |
| 7,259,164 B2 | 8/2007 | Mitchell et al. |
| 7,312,341 B2 | 12/2007 | DeSimone et al. |
| 7,405,295 B2 | 7/2008 | Currie et al. |
| 8,440,667 B2 | 5/2013 | Mitchell et al. |
| 8,450,321 B2 | 5/2013 | Mitchell et al. |
| 8,455,493 B2 | 6/2013 | Mitchell et al. |

(Continued)

FOREIGN PATENT DOCUMENTS

| | | |
|---|---|---|
| CA | 2175837 | 5/1995 |
| DE | 4337609 | 5/1995 |

(Continued)

OTHER PUBLICATIONS

Abrisqueta et al. Personalizing treatment for chronic lymphocytic leukemia. Expert Rev Hematol. 2011; 4(1):27-35.

(Continued)

*Primary Examiner* — Laura L Stockton
(74) *Attorney, Agent, or Firm* — Sheppard Mullin Richter & Hampton LLP

(57) ABSTRACT

Polymorphs of a bis-mesylate salt of a compound of Formula I:

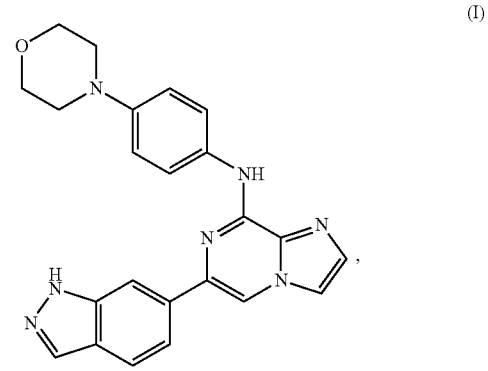

(I)

or a hydrate thereof, are provided. The bis-mesylate salt may also be depicted as a compound of Formula IA:

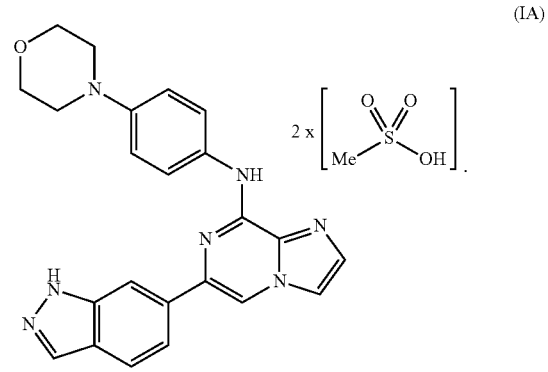

(IA)

Provided herein are also compositions thereof, methods for their preparation and methods for such polymorphs.

19 Claims, 23 Drawing Sheets

(56) References Cited

U.S. PATENT DOCUMENTS

| | | |
|---|---|---|
| 8,697,699 B2 | 4/2014 | Mitchell et al. |
| 8,748,607 B2 | 6/2014 | Mitchell et al. |
| 8,765,761 B2 | 7/2014 | Mitchell et al. |
| 8,796,270 B2 | 8/2014 | Mitchell |
| 8,962,835 B2 | 2/2015 | Mitchell et al. |
| 9,120,811 B2 | 9/2015 | Mitchell et al. |
| 9,212,191 B2 | 12/2015 | Mitchell et al. |
| 9,290,505 B2 | 3/2016 | Blomgren et al. |
| 9,376,441 B2 | 6/2016 | Currie et al. |
| 9,382,256 B2 | 7/2016 | Casteel et al. |
| 9,504,684 B2 | 11/2016 | Blomgren et al. |
| 9,562,056 B2 | 2/2017 | Blomgren et al. |
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 9,918,939 B2 * | 3/2018 | Casteel ............... A61K 9/2095 |
| 9,949,932 B2 * | 4/2018 | Casteel ............... A61K 9/2095 |
| 9,974,792 B2 * | 5/2018 | Di Paolo ........... A61K 31/5377 |
| 2003/0212073 A1 | 11/2003 | Currie et al. |
| 2004/0063715 A1 | 4/2004 | Paruch et al. |
| 2004/0067951 A1 | 4/2004 | Desimone et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0009832 A1 | 1/2005 | Sun et al. |
| 2005/0054648 A1 | 3/2005 | Mitchell et al. |
| 2005/0054649 A1 | 3/2005 | Currie et al. |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0222199 A1 | 10/2005 | Hayman et al. |
| 2005/0288295 A1 | 12/2005 | Currie et al. |
| 2006/0069084 A1 | 3/2006 | Burns et al. |
| 2006/0084650 A1 | 4/2006 | Dong et al. |
| 2006/0183746 A1 | 8/2006 | Currie et al. |
| 2007/0027135 A1 | 2/2007 | Bruncko et al. |
| 2007/0072860 A1 | 3/2007 | Bruncko et al. |
| 2007/0117804 A1 | 5/2007 | Zhao et al. |
| 2009/0221612 A1 | 9/2009 | Zhao et al. |
| 2010/0152159 A1 | 6/2010 | Zhao et al. |
| 2010/0222323 A1 | 9/2010 | Mitchell et al. |
| 2010/0305122 A1 | 9/2010 | Bruncko et al. |
| 2010/0305125 A1 | 12/2010 | Borchardt et al. |
| 2011/0002989 A1 | 1/2011 | Curatolo et al. |
| 2012/0157470 A1 | 6/2012 | Catron et al. |
| 2013/0023499 A1 | 1/2013 | Mitchell et al. |
| 2013/0210802 A1 | 8/2013 | Blomgren et al. |
| 2013/0231330 A1 | 9/2013 | Mitchell et al. |
| 2013/0237520 A1 | 9/2013 | Mitchell et al. |
| 2013/0237521 A1 | 9/2013 | Mitchell et al. |
| 2013/0267496 A1 | 10/2013 | Mitchell et al. |
| 2013/0310363 A1 | 10/2013 | Mitchell et al. |
| 2013/0338142 A1 | 12/2013 | Blomgren et al. |
| 2014/0051696 A1 | 2/2014 | Lannutti et al. |
| 2014/0148430 A1 | 5/2014 | Blomgren et al. |
| 2014/0336169 A1 | 11/2014 | Mitchell et al. |
| 2014/0357627 A1 | 12/2014 | Mitchell et al. |
| 2015/0038488 A1 | 2/2015 | Currie et al. |
| 2015/0038504 A1 | 2/2015 | Casteel et al. |
| 2015/0175626 A1 | 6/2015 | Blomgren et al. |
| 2015/0266902 A1 | 9/2015 | Blomgren et al. |
| 2016/0031894 A1 | 2/2016 | Mitchell et al. |
| 2016/0058758 A1 | 3/2016 | Blomgren et al. |
| 2016/0166580 A1 | 6/2016 | Casteel et al. |
| 2016/0168155 A1 | 6/2016 | Fung et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0095490 A1 | 4/2017 | Blomgren et al. |
| 2017/0121350 A1 | 5/2017 | Blomgren et al. |
| 2017/0258804 A1 | 9/2017 | Di Paolo et al. |
| 2018/0008608 A1 | 1/2018 | Di Paolo et al. |
| 2018/0117052 A1 * | 5/2018 | Di Paolo ............. A61K 31/437 |

FOREIGN PATENT DOCUMENTS

| | | |
|---|---|---|
| EP | 0480713 | 4/1992 |
| JP | 2001-302667 | 10/2001 |
| JP | 2004-528295 | 9/2004 |
| JP | 2005-530739 | 10/2005 |
| JP | 2011-511835 | 10/2005 |
| JP | 2008-519843 | 6/2008 |
| NZ | 593460 | 11/2013 |
| WO | WO-1988/004298 | 6/1988 |
| WO | WO-1995/012594 | 5/1995 |
| WO | WO-1996/004298 | 2/1996 |
| WO | WO-1996/034866 | 11/1996 |
| WO | WO-1999/028322 | 6/1999 |
| WO | WO-2001/027119 | 4/2001 |
| WO | WO-2001/083485 | 11/2001 |
| WO | WO-2002/010170 | 2/2002 |
| WO | WO-2002/030428 | 4/2002 |
| WO | WO-2002/060492 | 4/2002 |
| WO | WO-2002/066481 | 8/2002 |
| WO | WO-2002/076985 | 10/2002 |
| WO | WO-2003/070732 | 8/2003 |
| WO | WO-2003/089434 | 10/2003 |
| WO | WO-2004/022562 | 3/2004 |
| WO | WO-2004/026310 | 4/2004 |
| WO | WO-2004/026867 | 4/2004 |
| WO | WO-2004/026877 | 4/2004 |
| WO | WO-2004/072080 | 4/2004 |
| WO | WO-2004/072081 | 4/2004 |
| WO | WO-2005/005429 | 1/2005 |
| WO | WO-2005/014599 | 2/2005 |
| WO | WO-2005/019220 | 3/2005 |
| WO | WO-2005/047290 | 5/2005 |
| WO | WO-2005/085252 | 9/2005 |
| WO | WO-2006/044687 | 4/2006 |
| WO | WO-2006/053121 | 5/2006 |
| WO | WO-2008/025821 | 3/2008 |
| WO | WO-2008/033854 | 3/2008 |
| WO | WO-2009/039397 | 3/2009 |
| WO | WO-2009/070639 | 6/2009 |
| WO | WO-2009/077334 | 6/2009 |
| WO | WO-2009/102468 | 8/2009 |
| WO | WO-2009/156284 | 12/2009 |
| WO | WO-2010/000633 | 1/2010 |
| WO | WO-2010/006947 | 1/2010 |
| WO | WO-2010/027500 | 3/2010 |
| WO | WO-2010/068257 | 6/2010 |
| WO | WO-2010/068258 | 6/2010 |
| WO | WO-2011/074961 | 6/2011 |
| WO | WO-2011/112995 | 9/2011 |
| WO | WO-2012/147832 | 11/2012 |
| WO | WO-2014/028665 | 2/2014 |
| WO | WO-2015/017460 | 2/2015 |
| WO | WO-2015/017466 | 2/2015 |
| WO | WO-2015/017610 | 2/2015 |
| WO | WO-2015/100217 | 7/2015 |

OTHER PUBLICATIONS

Ackler, et al. Navitoclax (ABT-263) and bendamustine ± rituximab induce enhanced killing of non-Hodgkin's lymphoma tumours in vivo. British Journal of Pharmacology, 2012, vol. 167, pp. 881-891.

Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.

Ashizawa et al., "Optimization of Salt and Crystal Form and Crystallization Technique", Pharm Tech Japan, 2002, vol. 18, No. 10, pp. 81-96.

Bastin et al., "Salt Selection and Optimisation Procedures for Pharmaceutical New Chemical Entities", Organic Process Research and Development, American Chemical Society, US, vol. 4, No. 5, 2000, pp. 427-435.

(56) References Cited

OTHER PUBLICATIONS

Berge et al, J Pharm Sci 1977, vol. 66, Issue 1, pp. 1-19.
Blazar, et al. Advances in Graft-Versus-Host Disease Biology and Therapy. Nat. Rev. Immunol. Jun. 1, 2013; 12(6):443-458.
Bouloc et al., Bioorg Med Chem Ltrs vol. 20 Iss 20 (2010) pp. 5988-5993.
Brittain, H.G., "Polymorphism in Pharmaceutical Solids", Informa Healthcare, NY, 2009.
Buchner, et al. Spleen tyrosine kinase inhibition prevents chemokine- and integrin-mediated stromal protective effects in chronic lymphocytic leukemia. Blood, 2010, vol. 115, No. 22, pp. 4497-4506.
Bundgaard, H., (1985). Design of Prodrugs, Elsevier Science Publishers, B.V., The Netherlands, p. 1.
Burke, et al. A potential therapeutic strategy for chronic lymphocytic leukemia by combining Idelalisib and GS-9973, a novel spleen tyrosine kinase (Syk) inhibitor. Oncotarget. Feb. 2014; 5(4): 908-915.
Burrell, et al. The causes and consequences of genetic heterogeneity in cancer evolution. Nature. Sep. 19, 2013;501(7467):338-345. doi: 10.1038/nature12625.
Cancer Types. A to Z List. National Cancer Institute. 2017.
CancerConnect.com. Ibrutinib Highly Active in Patients with Chronic Lympocytic Leukemia with 17p Deletion. (Aug. 17, 2013). 2 pages.
Clinical Trials. A {hase 2 of GS-9973 in Subjects With Relapsed or Refractory Hematologic Malignancies. NCT01799889. Jun. 2013. 5 pages.
Communication pursuant to Article 94(3) for European Application No. 14750289.2 dated Dec. 14, 2017. (4 pages).
Communication pursuant to Rules 161(1) and 162 EPC for European Application No. 14750289.2 dated Mar. 8, 2016. (2 pages).
Currie, et al. Discovery of GS-9973, a selective and orally efficacious inhibitor of spleen tyrosine kinase. J. Med. Chem., 2014, vol. 57, pp. 3856-3873.
Dean, (2000). "Recent Advances in the Synthesis and Applications of Radiolabeled Compounds for Drug Discovery and Development," Curr. Pharm Des. 6(10): Preface, 1 page.
Ding, et al. (2002) "A Combinatorial Scaffold Approach Toward Kinase-Directed Heterocycle Libraries," J. Am Chem Soc., 124(8):1594-1596.
Elder, et al, (2010) J Pharm Sci, vol. 99, Issue 7, pp. 2948-2961.
European Communication dated Jun. 18, 2013, for EP Patent Application No. 11 709 600.8 filed on Mar. 11, 2011, 6 pages.
European Communication dated Jun. 6, 2013, for EP Patent Application No. 09 832 228.2 filed on Jun. 21, 2011, 5 pages.
European Communication dated Oct. 24, 2012, for European Patent Application No. 09710901.1, filed on Feb. 12, 2009, 5 pages.
Evans, (1981). "Synthesis of Radiolabeled Compounds," J. Radioanal. Chem. 64(1-2):9-32.
Examiner's Report for Canadian Application No. 2919661 dated Oct. 3, 2017. (3 pages).
Extended European Search Report dated Apr. 26, 2012, for EP 09 83 2229, filed on Jun. 21, 2011, 6 pages.
Extended European Search Report dated Jul. 27, 2012, for EP 09 83 2228.2, filed on Jun. 21, 2011, 12 pages.
Extended European Search Report dated Mar. 12, 2014, for EP 13005979.3, 5 pages.
Final Office Action dated Jan. 27, 2012, for U.S. Appl. No. 12/632,151, 15 pages.
Final Office Action dated May 2, 2013 for U.S. Appl. No. 13/343,624, 9 pages.
Final Office Action dated May 25, 2012, for U.S. Appl. No. 12/632,140, 9 pages.
Final Office Action dated Oct. 30, 2012, for U.S. Appl. No. 12/632,140, 9 pages.
Final Office Action dated Sep. 15, 2011, for U.S. Appl. No. 12/632,140, 15 pages.
Final Office Action dated Sep. 5, 2012, for U.S. Appl. No. 12/632,151, 11 pages.
Flynn. B Cells, T Follicular Helpers, and Germinal Centers as Facilitators of Chronic Graft-Versus-Host disease. Doctoral Dissertation. University of Minnesota, Aug. 2014.
Gavezzotti. Are Crystal Structures Predictable? Acc. Chem. Res., 1994, 27 (10), pp. 309-314.
GenBank Accession No. AY050647.1, created on Oct. 7, 2001, located at <http://www.ncbi.nlm.nih.gov/nuccore/AY050647.1>, last visited on Dec. 28, 2011, 1 page.
Golub et al., "Molecular Classification of Cancer: Class Discovery and Class Prediction by Gene Expression Monitoring". Science. Oct. 15, 1999; 286:531-537.
Hackam, et al. (2006). "Translation of Research Evidence From Animals to Humans," JAMA 296(14):1731-1732.
Hill, et al. B-cell antigen receptor signaling in chronic lymphocytic leukemia: therapeutic targets and translational opportunities. International Reviews of Immunology, 2013, vol. 32, pp. 377-396.
Hirayama, N., "Handbook for creating organic compound crystals—principle and technical know-how", Maruzen KK, Jul. 25, 2008, pp. 17-23, pp. 37-40, pp. 45-51, and pp. 57-65.
International Preliminary Examination Report dated Aug. 5, 2004, for PCT Application No. PCT/US2003/12222, 11 pages.
International Preliminary Examination Report dated Oct. 27, 2004, for PCT Application No. PCT/US2003/28329, 5 pages.
International Preliminary Report on Patentability for International Application No. PCT/US2014/048733 dated Feb. 2, 2016. (6 pages).
International Preliminary Report on Patentability dated Aug. 17, 2010, for PCT Application No. PCT/US2009/000919, 8 pages.
International Preliminary Report on Patentability dated Jan. 5, 2011, for PCT Application No. PCT/US2009/006445, 6 pages.
International Preliminary Report on Patentability dated Jun. 8, 2011, for PCT Application No. PCT/US/2009/006446, 6 pages.
International search report and written opinion dated Jun. 23, 2016 for PCT/US2016/028303, 9 pages.
International Search Report and Written Opinion for International Application No. PCT/US2014/048733 dated Oct. 8, 2014. (8 pages).
International Search Report and Written Opinion dated Oct. 13, 2014, for PCT Application No. PCT/US2014/048741, 10 pages.
International Search Report and Written Opinion dated Dec. 30, 2004, for PCT Application No. PCT/US2004/018227, 10 pages.
International Search Report and Written Opinion dated Dec. 8, 2004, for PCT Application No. PCT/US2004/021150, 10 pages.
International Search Report and Written Opinion dated Feb. 1, 2005 for PCT Application No. PCT/US2004/025884, 8 pages.
International Search Report and Written Opinion dated Jul. 7, 2004, for PCT Application No. PCT/US2004/003922, 12 pages.
International Search Report and Written Opinion dated Jul. 7, 2004, for PCT Application No. PCT/US2004/003923, 12 pages.
International Search Report and Written Opinion dated Jun. 23, 2005, for PCT Application No. PCT/US2004/037433, 15 pages.
International Search Report dated Apr. 26, 2011, for Application No. PCT/US2011/028194, 5 pages.
International Search Report dated Feb. 12, 2010, for PCT Application No. PCT/US/2009/006446, 3 pages.
International Search Report dated Feb. 12, 2010, for PCT Application No. PCT/US2009/006445, 3 pages.
International Search Report dated Feb. 9, 2004, for PCT Application No. PCT/US2003/28329.
International Search Report dated May 12, 2009, for PCT Application No. PCT/US2009/000919, 5 pages.
International Search Report dated May 3, 2015, for PCT Application No. PCT/US2014/071842, 3 pgs.
International Search Report dated Oct. 22, 2003, for PCT Application No. PCT/US2003/12222.
Invitation to Pay Additional Fees with Partial International Search Report dated May 3, 2005, for PCT Application No. PCT/US2004/037433, 9 pages.
Japanese Notice of Reasons for Rejection dated Feb. 4, 2014 for Japanese Patent Application No. 2011-539524, 10 pages. (with English translation).
Japanese Notice of Reasons for Rejection dated Feb. 6, 2014, for Japanese Patent Application No. 2011-539525, 11 pages. (with English translation).

(56) References Cited

OTHER PUBLICATIONS

Jeffrey, T.K. et al. (1998). "Phosphodiesterase III and V Inhibitors on Pulmonary Artery from Pulmonary Hypertensive Rats: Differences Between Early and established Pulmonary Hypertension", *J. Cardiovascular Pharmacology*, 32(2): 213-219.
Jordan, V.C. (Mar. 2003). "Tamoxifen: A Most Unlikely Pioneering Medicine" *Nature Reviews: Drug Discovery* 2:205-213.
Kabalka, et al. (1989). "The Synthesis of Radiolabeled Compounds via Organometallic Intermediates," *Tetrahedron* 45(21):6601-6621.
Kojima et al., "Aiming for better efficiency of crystalline selection in the development of pharmaceuticals", Journal of Pharmaceutical Science and Technology, Japan, Sep. 1, 2008, vol. 68, No. 5, p. 344-349.
Krisenko, et al. Calling in SYK: SYK's Dual Role as Tumor Promoter and Tumor Suppressor in Cancer. Biochimica et Biophysica Acta. Jan. 2015; 1853(1):254-263.
Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," The American Society for Pharmacology and Experimental Therapeutics 26(11)1120-1127.
Le Huu, et al. Blockade of Syk Ameliorates the Development of Murine Sclerodermatous Chronic Graft-Versus-Host Disease. Journal of Dermatological Science. 2014; 74:214-221.
Lumma, Jr., et al. (1983) "Piperazinylimidazo [1,2-a]pyrazines with Selective affinity for in Vitro a-Adrenergic Receptor Subtypes," *J. Med. Chem.* 26(3):357-363.
Ma, et al. Signal transduction inhibitors in chronic lymphocytic leukemia. Current Opinion in Oncology, 2011, vol. 23, pp. 601-608.
Merino, et al. Bcl-2, Bcl-x(L), and Bcl-w are not equivalent targets of ABT-737 and navitoclax (ABT-263) in lymphoid and leukemic cells. Blood, 2012, vol. 119, No. 24, pp. 5807-5816.
Non-Final Office Action dated Jul. 7, 2015, for U.S. Appl. No. 14/578,973, 11 pages.
Non-Final Office Action dated Feb. 12, 2016, for U.S. Appl. No. 14/795,123, 13 pages.
Non-Final Office Action dated Apr. 13, 2011 for U.S. Appl. No. 12/370,103, 11 pages.
Non-Final Office Action dated Apr. 3, 2006, for U.S. Appl. No. 10/776,002, 13 pages.
Non-Final Office Action dated Dec. 31, 2013, for U.S. Appl. No. 13/901,523, 22 pages.
Non-Final Office Action dated Feb. 17, 2012 for U.S. Appl. No. 12/632,140, 11 pages.
Non-Final Office Action dated Jan. 25, 2013, for U.S. Appl. No. 13/343,624, 18 pages.
Non-Final Office Action dated Jan. 8, 2007, for U.S. Appl. No. 10/915,696, 8 pages.
Non-Final Office Action dated Jun. 29, 2011, for U.S. Appl. No. 12/632,151, 17 pages.
Non-Final Office Action dated May 10, 2011 for U.S. Appl. No. 12/632,140, 18 pages.
Non-Final Office Action dated May 17, 2012, for U.S. Appl. No. 12/632,151, 15 pages.
Non-Final Office Action dated May 24, 2006, for U.S. Appl. No. 10/776,631, 10 pages.
Non-Final Office Action dated Nov. 4, 2013, for U.S. Appl. No. 13/862,147, 18 pages.
Non-Final Office Action dated Oct. 11, 2012, for U.S. Appl. No. 13/441,441, 8 pages.
Non-Final Office Action dated Oct. 11, 2013, for U.S. Appl. No. 13/868,967, 17 pages.
Non-Final Office Action dated Oct. 16, 2013, for U.S. Appl. No. 13/868,971, 16 pages.
Non-Final Office Action dated Sep. 26, 2006, for U.S. Appl. No. 10/658,121, 7 pages.
Notice of Allowance dated Jan. 12, 2017 for U.S. Appl. No. 14/446,011. 8 pages.
Notice of Allowance dated Feb. 16, 2016 for U.S. Appl. No. 14/448,160. 25 pages.
Notice of Allowance dated Feb. 24, 2017 for U.S. Appl. No. 14/559,707. 7 pages.
Notice of Allowance dated Mar. 9, 2016 for U.S. Appl. No. 14/445,970. 8 pages.
Notice of Allowance dated Mar. 17, 2015 for U.S. Appl. No. 14/274,618. 9 pages.
Notice of Allowance dated Apr. 27, 2017 for U.S. Appl. No. 14/796,795. 5 pages.
Notice of Allowance dated Apr. 28, 2016 for U.S. Appl. No. 14/629,390. 10 pages.
Notice of Allowance dated Jun. 16, 2017 for U.S. Appl. No. 14/882,278. 8 pages.
Notice of Allowance dated Jul. 13, 2015 for U.S. Appl. No. 14/300,189. 9 pages.
Notice of Allowance dated Aug. 3, 2017 for U.S. Appl. No. 15/178,164. 7 pages.
Notice of Allowance dated Sep. 22, 2016 for U.S. Appl. No. 14/446,011. 8 pages.
Notice of Allowance dated Oct. 4, 2016 for U.S. Appl. No. 13/806,094. 8 pages.
Notice of Allowance dated Oct. 13, 2015 for U.S. Appl. No. 14/629,390. 10 pages.
Notice of Allowance dated Oct. 14, 2016 for U.S. Appl. No. 14/629,390. 11 pages.
Notice of Allowance dated Dec. 5, 2016 for U.S. Appl. No. 14/796,795. 5 pages.
Notice of Allowance dated Apr. 20, 2007, for U.S. Appl. No. 10/915,696, 7 pages.
Notice of Allowance dated Aug. 11, 2006, for U.S. Appl. No. 10/776,002, 10 pages.
Notice of Allowance dated Aug. 8, 2007, for U.S. Appl. No. 10/658,121, 6 pages.
Notice of Allowance dated Mar. 6, 2007, for U.S. Appl. No. 10/658,121, 6 pages.
Notice of Allowance dated Aug. 12, 2013, for U.S. Appl. No. 13/343,624, 9 pages.
Notice of Allowance dated Dec. 26, 2013, for U.S. Appl. No. 13/343,624, 10 pages.
Notice of Allowance dated Feb. 12, 2014, for U.S. Appl. No. 13/862,147, 9 pages.
Notice of Allowance dated Feb. 5, 2014, for U.S. Appl. No. 13/868,967, 8 pages.
Notice of Allowance dated Jan. 14, 2013, for U.S. Appl. No. 12/632,151, 8 pages.
Notice of Allowance dated Jan. 25, 2013, for U.S. Appl. No. 12/632,140, 8 pages.
Notice of Allowance dated Jan. 28, 2013, for U.S. Appl. No. 13/441,441, 8 pages.
Notice of Allowance dated Jan. 30, 2014, for U.S. Appl. No. 13/868,971, 8 pages.
Notice of Allowance dated Oct. 16, 2014, for U.S. Appl. No. 13/862,194, 8 pages.
Notice of Allowance dated Sep. 7, 2006, for U.S. Appl. No. 10/776,631, 7 pages.
Office Action and Search Report dated Oct. 28, 2016 for CN Application No. 201480043503.5. (9 pages).
Office Action dated Jan. 20, 2017 for CA Application No. 2,919,661. (4 pages).
Office Action dated Jan. 20, 2017 for U.S. Appl. No. 15/010,906. 30 pages.
Office Action dated Feb. 3, 2015 for U.S. Appl. No. 14/300,189. 17 pages.
Office Action dated Feb. 11, 2016 for U.S. Appl. No. 13/806,094. 8 pages.
Office Action dated Mar. 1, 2017 for U.S. Appl. No. 14/882,278. 18 pages.
Office Action dated Mar. 10, 2017 for U.S. Appl. No. 14/907,767. (80 pages).
Office Action dated Mar. 27, 2017 for U.S. Appl. No. 15/298,950. 10 pages.
Office Action dated Apr. 13, 2017 for EP Application No. 14750289.2. (6 pages).

(56) References Cited

OTHER PUBLICATIONS

Office Action dated Apr. 14, 2017 for U.S. Appl. No. 14/906,248. 10 pages.
Office Action dated Apr. 17, 2017 for JP Application No. 2016-531837. (4 pages).
Office Action dated Apr. 19, 2017 for EA Application No. 201690172. (4 pages).
Office Action dated Apr. 21, 2017 for U.S. Appl. No. 15/404,120. 16 pages.
Office Action dated Apr. 22, 2016 for U.S. Appl. No. 14/446,011. (22 pages).
Office Action dated Apr. 27, 2017 for AU Application No. 2014296308. (3 pages).
Office Action dated Apr. 29, 2010 for U.S. Appl. No. 10/985,023. 14 pages.
Office Action dated May 5, 2016 for Pakistan Application No. 550/2014. (2 pages).
Office Action dated Jun. 13, 2017 for CN Application No. 201480043503.5. (7 pages).
Office Action dated Jun. 14, 2016 for U.S. Appl. No. 13/806,094. 12 pages.
Office Action dated Jun. 16, 2017 for U.S. Appl. No. 15/010,906. 36 pages.
Office Action dated Jun. 16, 2017 for U.S. Appl. No. 15/017,394. 24 pages.
Office Action dated Jun. 17, 2016 for U.S. Appl. No. 14/796,795. 11 pages.
Office Action dated Jul. 2, 2015 for U.S. Appl. No. 13/806,094. 13 pages.
Office Action dated Jul. 10, 2009 for U.S. Appl. No. 10/985,023. 32 pages.
Office Action dated Jul. 14, 2016 for AU Application No. 2014296308. (3 pages).
Office Action dated Jul. 15, 2015 for U.S. Appl. No. 14/445,970. 13 pages.
Office Action dated Jul. 17, 2017 for U.S. Appl. No. 14/907,767. (15 pages).
Office Action dated Jul. 26, 2017 for U.S. Appl. No. 14/906,248. 8 pages.
Office Action dated Jul. 28, 2017 for U.S. Appl. No. 15/404,120. 19 pages.
Office Action dated Aug. 2, 2016 for NZ Application No. 715776. (3 pages).
Office Action dated Aug. 7, 2015 for U.S. Appl. No. 14/559,707. 13 pages.
Office Action dated Aug. 9, 2017 for U.S. Appl. No. 15/133,041. 18 pages.
Office Action dated Aug. 9, 2017 for U.S. Appl. No. 15/603,663. 13 pages.
Office Action dated Aug. 24, 2017 for U.S. Appl. No. 15/298,950. 31 pages.
Office Action dated Aug. 24, 2017 for U.S. Appl. No. 15/387,557. 10 pages.
Office Action dated Sep. 16, 2016 for U.S. Appl. No. 14/559,707. 12 pages.
Office Action dated Oct. 8, 2008 for U.S. Appl. No. 10/985,023. 16 pages.
Office Action dated Oct. 23, 2015 for U.S. Appl. No. 14/448,160. 25 pages.
Office Action dated Dec. 5, 2016 for JP Application No. 2016-531837. (11 pages).
Office Action dated Dec. 8, 2014 for U.S. Appl. No. 14/274,618. 9 pages.
Office Action dated Dec. 10, 2015 for U.S. Appl. No. 14/559,707. 11 pages.
Office Action dated Dec. 12, 2007 for U.S. Appl. No. 10/985,023. 17 pages.
Office Action dated Dec. 15, 2016 for U.S. Appl. No. 15/178,164. 34 pages.
Office Action Dated Dec. 15, 2014 for Japan Patent Application No. 2014-095907.
Office Action Dated Jan. 15, 2015 for Chilean Patent Application No. 1360-11.
Office Action Dated Jan. 30, 2015 for Vietnamese Patent Application No. 1-2011-01623.
Office Action Dated Feb. 18, 2015 for Eurasian Patent Application No. 201400197.
Office Action Dated Mar. 30, 2015 for European Patent Application No. 13 005 979.3.
Office Action for Chile Application No. 2016-00238 dated Nov. 14, 2017. (15 pages).
Office Action for Colombia Application No. 16-051.186 dated Mar. 22, 2016. (4 pages).
Office Action for Colombia Application No. 16-051.186 dated Oct. 7, 2017. (11 pages).
Office Action for Cuban Application No. 2016-0019 dated Sep. 29, 2017. (3 pages).
Office Action for Eurasian Application No. 201690172 dated May 25, 2016. (5 pages).
Office Action for Korean Application No. 10-2016-7005206 dated Jun. 16, 2017. (5 pages).
Office Action for U.S. Appl. No. 15/484,844 dated May 5, 2017. (22 pages).
Office Action for Ukraine Application No. a201601036 dated Jan. 8, 2018. (4 pages).
Office Action for Ukraine Patent Application No. a 2016 01036 dated Jul. 10, 2017. (4 pages).
Office Action dated Jul. 28, 2014, for U.S. Appl. No. 13/862,194, 7 pages.
Opposition for Chile Application No. 2016-00238 dated Feb. 9, 2017. (6 pages).
Oravcova, J. et al. (1996). "Drug-Protein Binding Studies New Trends in Analytical and Experimental Methodology," J Chromatogr B 677:1-28.
Owen, et al. Obinutuzumab for the treatment of lymphoproliferative disorders. Expert Opin Biol Ther. Mar. 2012;12(3):343-351. doi: 10.1517/14712598.2012.657622. Epub Jan. 28, 2012.
Paulekuhn et al., Trends in Active Pharmaceutical Ingredient Salt Selection Based on Analysis of the Orange Book Database. J Med Chem 2007, 50, pp. 6665-6672.
Report of the state of the art for Panamanian Application No. 91014-01 dated Jun. 16, 2017. (5 pages).
Resolution Dated Dec. 18, 2014 for Colombian Patent Application No. 14-049.611.
Restriction Requirement dated Jan. 25, 2017 for U.S. Appl. No. 15/133,041. 10 pages.
Restriction Requirement dated Feb. 15, 2017 for U.S. Appl. No. 15/404,120. 10 pages.
Restriction Requirement dated Mar. 27, 2015 for U.S. Appl. No. 13/806,094. 10 pages.
Restriction Requirement dated Jun. 30, 2015 for U.S. Appl. No. 14/629,390. 8 pages.
Restriction Requirement dated Aug. 16, 2007 for U.S. Appl. No. 10/985,023. 8 pages.
Restriction Requirement dated Nov. 7, 2016 for U.S. Appl. No. 15/150,038. 9 pages.
Restriction Requirement dated Dec. 8, 2010, for U.S. Appl. No. 12/632,140, 10 pages.
Restriction Requirement dated Jan. 27, 2006, for U.S. Appl. No. 10/776,631, 6 pages.
Restriction Requirement dated Jan. 30, 2006, for U.S. Appl. No. 10/658,121, 5 pages.
Restriction Requirement dated Jan. 4, 2006, for U.S. Appl. No. 10/776,002, 7 pages.
Restriction Requirement dated May 18, 2006, for U.S. Appl. No. 10/658,121, 5 pages.
Restriction Requirement dated Oct. 13, 2006, for U.S. Appl. No. 10/915,696, 5 pages.
Restriction Requirement dated Oct. 20, 2004, for U.S. Appl. No. 10/419,682, 9 pages.
Restriction Requirement dated Apr. 14, 2014, for U.S. Appl. No. 13/862,194, 5 pages.

(56) References Cited

OTHER PUBLICATIONS

Restriction Requirement dated Dec. 8, 2010, for U.S. Appl. No. 12/632,151, 10 pages.
Restriction Requirement dated Feb. 17, 2011, for U.S. Appl. No. 12/370,103, 10 pages.
Restriction Requirement dated Jan. 27, 2014, for U.S. Appl. No. 13/609,068, 8 pages.
Restriction Requirement dated Jul. 26, 2012, for U.S. Appl. No. 13/441,441, 9 pages.
Restriction Requirement dated Jul. 3, 2013, for U.S. Appl. No. 13/868,971, 5 pages.
Restriction Requirement dated Jun. 14, 2013, for U.S. Appl. No. 13/862,147, 10 pages.
Restriction Requirement dated Jun. 24, 2013, for U.S. Appl. No. 13/868,967, 10 pages.
Restriction Requirement dated Nov. 27, 2012, for U.S. Appl. No. 13/343,624, 10 pages.
Restriction Requirement dated Oct. 15, 2013, for U.S. Appl. No. 13/901,523, 5 pages.
Restriction Requirement dated Sep. 8, 2014, for U.S. Appl. No. 14/274,618, 6 pages.
Roberts, et al. Substantial susceptibility of chronic lymphocytic leukemia to BCL2 inhibition: results of a phase I study of navitoclax in patients with relapsed or refractory disease. J. Clin. Oncol., 2012, vol. 30, No. 5, pp. 488-496.
Second Written Opinion dated Apr. 13, 2004, for PCT Application No. PCT/US2003/12222, 7 pages.
Serajuddin, A.T.M., "Salt formation to improve drug solubility." Advanced Drug Delivery Reviews, 2007; 59:603-616.
Silverman, R.B. (1992), The Organic Chemistry of Drug Design and Drug Action, Academic Press, Inc. San Diego, CA, pp. 352-400.
Stenberg, K.A.E. et al., (2000). "KinMutBase, a Database of Human Disease-Causing Protein Kinase Mutations", *Nucleic Acids Research* 28(1):369-371.
Takada, N., "API form screening and selection in drug discovery stage", Pharm Stage, Jan. 15, 2007, vol. 6, No. 10, p. 20-25.
Taylor, et al., (1984). "Hydrogen-Bond Geometry in Organic Crystals", Acc. Chem Res. 17:320-326.
Vassilev, et al. Therapeutic Potential of Inhibiting Bruton's Tyrosine Kinase, (BTK). Current Pharmaceutical Design, vol. 10, No. 15, Jun. 2004, pp. 1757-1766(10).
Vippagunta, et al. Crystalline solids. Advanced Drug Delivery Reviews. vol. 48, Issue 1, May 16, 2001, pp. 3-26.
Vitse, O. et al. (1999). "New Imidazo [1,2-α]pyrazine Derivatives with Bronchodilatory and Cyclic Nucleotide Phosphodiesterase Inhibitory Activities," Bioorganic and Medicinal Chemistry 7:1059-1065.
Willander, et al. NOTCH1 Mutations Influence Survival in Chronic Lymphocytic Leukemia Patients. BMC Cancer. Jun. 2013; 13:274, pp. 1-6.
Written Opinion dated Apr. 26, 2011, for Application No. PCT/US2011/028194, 6 pages.
Written Opinion dated Dec. 5, 2003, for PCT Application No. PCT/US2003/12222, 6 pages.
Written Opinion dated Jul. 6, 2004, for PCT Application No. PCT/US2003/28329, 5 pages.
Written Opinion dated Feb. 12, 2010, for PCT Application No. PCT/US/2009/006446, 4 pages.
Written Opinion dated Feb. 12, 2010, for PCT Application No. PCT/US2009/006445, 4 pages.
Written Opinion dated May 12, 2009, for PCT Application No. PCT/US2009/000919, 7 pages.
Zaragoza, D.F. (2005). Side Reactions in Organic Synthesis: A Guide to Successful Synthesis Design, Weinheim;WILEY-VCH Verlag GmbH &Co. KGaA, Preface, 2 pages.
Examination Report for AU Appln. No. 2017225136 dated May 7, 2018, 3 pages.
Examination Report for IN Appln. No. 201617001841 dated Jul. 5, 2018, 5 pages.
Office Action for TW Appln. No. 103125870 dated Jun. 29, 2018, 4 pages.
Supplementary Examination Written Opinion for SG Appln. No. 11201600385T dated Mar. 5, 2018, 5 pages.

\* cited by examiner

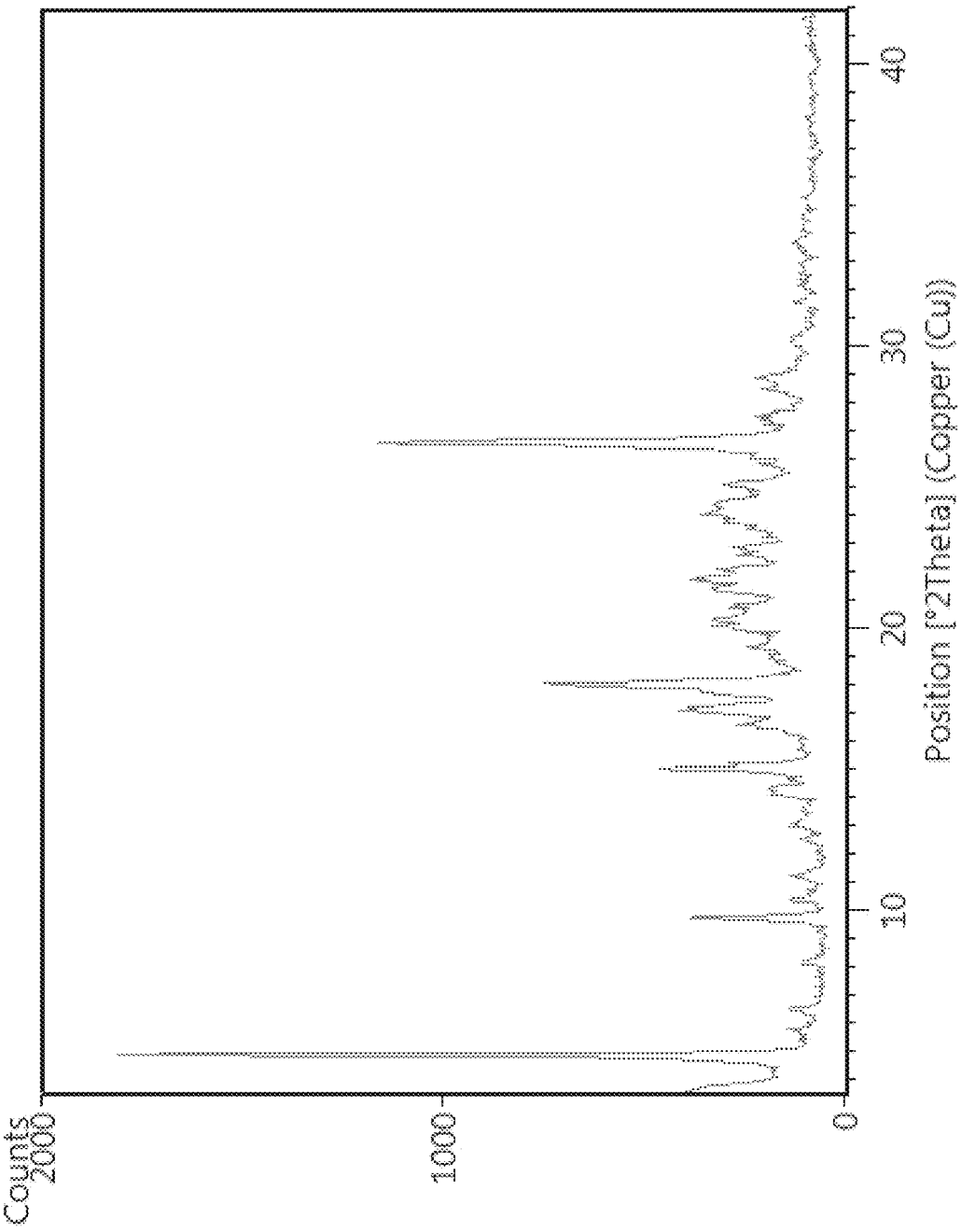

(A)

(B)

POLYMORPH OF SYK INHIBITORS

CROSS REFERENCE TO RELATED APPLICATIONS

This application is a continuation of U.S. application Ser. No. 15/484,844, filed Apr. 11, 2017, which is a divisional of U.S. application Ser. No. 14/446,011, filed Jul. 29, 2014, now U.S. Pat. No. 9,657,023, which claims the benefit of U.S. Provisional Application No. 61/860,197, filed Jul. 30, 2013, the disclosures of which are hereby incorporated herein by reference in their entirety.

FIELD

The present disclosure relates to polymorphs and polymorph pharmaceutical compositions of compounds that inhibit Spleen Tyrosine Kinase (Syk) activity. The disclosure also relates to methods of preparing such polymorphs and polymorph pharmaceutical compositions, and the use of such polymorphs and pharmaceutical compositions in treating subjects with various diseases, including cancer and inflammatory conditions.

BACKGROUND

The inhibition of Spleen Tyrosine Kinase (Syk) activity may be useful for treating certain types of cancer and autoimmune diseases. One such compound that has been found to inhibit Syk activity is represented by Formula I:

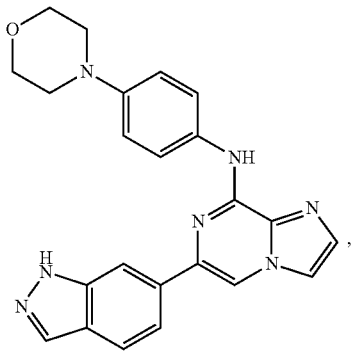

(I)

or a pharmaceutically acceptable salt thereof. This compound and its synthesis have been described in U.S. Pat. Nos. 8,450,321 and 8,455,493, which are hereby incorporated herein by reference in their entirety, and are hereby incorporated by reference specifically with reference to Examples 1 and 2.

Early clinical oral formulations have involved the use of a mono-mesylate salt of the compound of Formula I. Various challenges, however, have been observed in early clinical studies when this oral formulation was administered to human subjects. First, high inter-subject variability has been observed, which could lead to variable pharmacodynamic responses in subjects. Second, significant drug-drug-interaction and pH effect have been observed with acid suppressants, and it is desired to minimize such observed drug-drug-interaction. Third, a dose-dependent food effect has been observed, and it is also desired to minimize such effect. Fourth, it is desired to improve oral bioavailability.

What is desired in the art are physically stable forms of the compound of Formula I, or a pharmaceutically acceptable salt thereof, that address each of these challenges and facilitate manufacturing processes.

SUMMARY

To overcome the reduced oral bioavailability of the mono-mesylate salt of the compound of Formula I, a new compound was investigated. A bis-mesylate salt of the compound of Formula I has been chosen for further development. Such bis-mesylate salt may be depicted in various ways. For example, the bis-mesylate salt may be depicted as the compound of Formula IA, having the molecular structure:

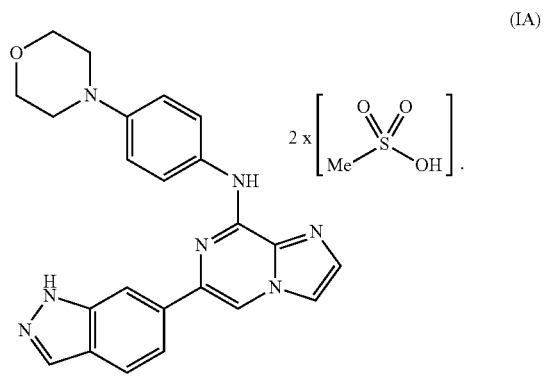

(IA)

One of skill in the art would understand that when the bis-mesylate salt of the compound of Formula I is depicted as Formula IA above, the ionic form (e.g., the cationic form of the compound of formula I and the anionic form of the methanesulfonic acid) is intended.

In some embodiments, a hydrate of the bis-mesylate salt of the compound of Formula I is provided by this disclosure. In cumin embodiments, a monohydrate of the bis-mesylate salt of the compound of Formula I is provided by this disclosure. In one embodiment, certain polymorphic forms of the bis-mesylate salt of the compound of Formula I, or a hydrate thereof, are provided by this disclosure.

In one aspect, provided herein are polymorphs of a bis-mesylate salt of the compound of Formula I (e.g., a compound of Formula IA), or a hydrate thereof. In certain aspects, polymorphic forms of a hydrate, bis-mesylate salt of the compound of Formula I are provided. Specifically, in one aspect, polymorphic Forms 3 and 7 of the bis-mesylate salt of the compound of Formula I (e.g., a compound of Formula IA) are provided. Methods of making and using these polymorphic forms are also provided. Also provided are polymorphic products obtained by the processes described herein (e.g., obtained by the described methods of making). Pharmaceutical compositions comprising one or more polymorphic forms of a bis-mesylate salt of the compound of Formula I (e.g., a compound of Formula IA), or a hydrate thereof, and a pharmaceutically acceptable carrier are provided. Articles of manufacture and unit dosage forms comprising one or more polymorphic forms of a bis-mesylate salt of the compound of Formula I (e.g., a compound of Formula IA), or a hydrate thereof, are provided. Kits comprising one or more polymorphic forms of a bis-mesylate salt of the compound of Formula I (e.g., a compound of Formula IA), or a hydrate thereof, and instructions for use (e.g., instructions for use in SYK-mediated disorder, such as cancer or an autoimmune disease) are also provided. In some embodiments of the foregoing methods of making and using the polymorphic forms, polymorphic products, pharmaceutical compositions, articles of manufacture and unit dosage forms, and kits provided herein, the bis-mesylate salt of the compound of Formula I is a hydrate thereof. In certain embodiments, the bis-mesylate salt of the compound of Formula I is a monohydrate thereof. In one embodiment, the bis-mesylate salt of the compound of Formula I or a hydrate thereof is polymorph Form 3 or polymorph Form 7, or a combination thereof.

In one aspect, provided is a bis-mesylate salt of a compound of Formula I:

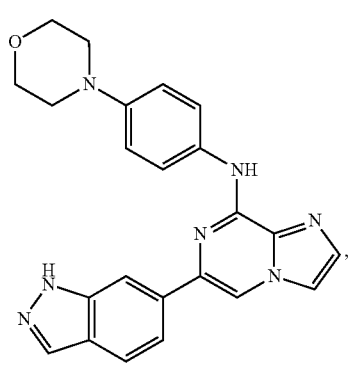

(I)

or a hydrate thereof. In some embodiments, provided is a hydrate of the bis-mesylate salt of the compound of Formula I. In certain embodiments, provided is a monohydrate of the bis-mesylate salt of the compound of Formula I. In some variations, the bis-mesylate salt or a hydrate thereof is crystalline.

Provided herein is also a polymorph of the bis-mesylate salt of the compound of Formula I, or a hydrate thereof. In some embodiments, provided is a polymorph of a hydrate of the bis-mesylate salt of the compound of Formula I. In certain embodiments, provided is a polymorph of a monohydrate of the bis-mesylate salt of the compound of Formula I. Polymorph Forms 3 and Form 7 are provided in this disclosure, as are methods of making and using polymorph Form 3 and Form 7, and pharmaceutical compositions, articles of manufacture, unit dosage forms and kits comprising polymorph Form 3 or Form 7, or both.

In some embodiments, a polymorph of a monohydrate, bis-mesylate salt of a compound of Formula I is polymorph Form 3, characterized by or having an X-ray diffraction pattern comprising 2θ-reflections (±0.2 degrees) at 13.8, 16.9, 22.9, and 26.1. In further embodiments, a polymorph of a monohydrate, bis-mesylate salt of a compound of Formula I is polymorph Form 3, characterized by or having an X-ray diffraction pattern comprising 2θ-reflections (±0.2 degrees) at 7.7, 12.9, 17.7, and 18.1. In yet other embodiments a polymorph of a monohydrate, bis-mesylate salt of a compound of Formula I is polymorph Form 3, characterized by or having an X-ray diffraction pattern comprising 2θ-reflections (±0.2 degrees) at 7.7, 12.9, 13.8, 16.9, 17.7, 18.1, 22.9, and 26.1. When describing the 2θ-reflections in the X-ray diffraction pattern (e.g., of polymorph Form 3, also referred to herein as "Form 3" or "Form III"), it should be understood that ±0.2 degrees can also be expressed as "plus or minus 0.2 degrees 2θ". In some embodiments, a polymorph of a monohydrate, bis-mesylate salt of a compound of Formula I is polymorph Form 3, characterized by or having an X-ray diffraction pattern substantially as shown in FIG. 1A. In other embodiments, a polymorph of a monohydrate, bis-mesylate salt of a compound of Formula I is polymorph Form 3, characterized by or having an X-ray diffraction pattern substantially as shown in FIG. 1B.

In other embodiments, a polymorph of a hydrate, bis-mesylate salt of a compound of Formula I is polymorph Form 7, characterized by or having an X-ray diffraction pattern comprising 2θ-reflections at 4.9 (±0.2 degrees), 9.8 (±0.2 degrees), and 26.7 (±0.4 degrees). In one variation, a polymorph of a hydrate, bis-mesylate salt of a compound of Formula I is polymorph Form 7, characterized by or having an X-ray diffraction pattern comprising 2θ-reflections at 4.9 (±0.2 degrees), 9.8 (±0.2 degrees), and 26.7 (±0.3 degrees). In certain embodiments, a polymorph of a hydrate, bis-mesylate salt of a compound of Formula I is polymorph Form 7, characterized by or having an X-ray diffraction pattern comprising 2θ-reflections (±0.2 degrees) at 4.9, 9.8, and 26.7. In further embodiments, a polymorph of a hydrate, bis-mesylate salt of a compound of Formula I is polymorph Form 7, characterized by or having an X-ray diffraction pattern comprising 2θ-reflections (±0.2 degrees) at 15.0 and 18.0.

In one variation, a polymorph of a hydrate, bis-mesylate salt of a compound of Formula I is polymorph Form 7, characterized by or having an X-ray diffraction pattern comprising 2θ-reflections (±0.2 degrees) at 4.9, 9.8, 15.0 and 18.0; and 2θ-reflections (±0.4 degrees) at 26.7. In one variation, a polymorph of a hydrate, bis-mesylate salt of a compound of Formula I is polymorph Form 7, characterized by or having an X-ray diffraction pattern comprising 2θ-reflections (±0.2 degrees) at 4.9, 9.8, 15.0 and 18.0; and 2θ-reflections (±0.3 degrees) at 26.7. In another variation, a polymorph of a hydrate, bis-mesylate salt of a compound of Formula I is polymorph Form 7, characterized by or having an X-ray diffraction pattern comprising 2θ-reflections (±0.2 degrees) at 4.9, 9.8, 15.0, 18.0, and 26.7. In some embodiments, a polymorph of a hydrate, bis-mesylate salt of a compound of Formula I is polymorph Form 7, characterized by or having an X-ray diffraction pattern substantially as shown in FIG. 2A. In other embodiments, a polymorph of a hydrate, bis-mesylate salt of a compound of Formula I is polymorph Form 7, characterized by or having an X-ray diffraction pattern substantially as shown in FIG. 2B. When describing the 2θ-reflections in the X-ray diffraction pattern e.g., of polymorph Form 7, also referred to herein as "Form 7" or "Form VII"), it should be understood that ±0.2 degrees, ±0.3 degrees, and ±0.4 degrees can also be expressed as "plus or minus 0.2 degrees 2θ", "plus or minus 0.3 degrees 2θ", and "plus or minus 0.4 degrees 2θ", respectively.

In another aspect, provided is a hydrate of a bis-mesylate salt of the compound of Formula I. In certain aspects, the hydrate, bis-mesylate salt of the compound of Formula I is a polymorph selected from the group consisting of Form 3 and Form 7; wherein Form 3 is characterized by or has a differential scanning calorimetry profile substantially as shown in FIG. 3A, 3B or 3C, and/or a thermogravametrical analysis profile substantially as shown in FIG. 3B or 3C; and Form 7 is characterized by or has a differential scanning calorimetry profile substantially as shown in FIG. 4A, 4B or 4C, and/or a thermogravametrical analysis profile substantially as shown in FIG. 4B or 4C. It is understood that "and/or", e.g., in reference to A and/or B intends and describes: (i) embodiments wherein A is present; (ii) embodiments wherein B is present; and (iii) embodiments wherein both A and B are present. In a further embodiment that may be combined with any of the foregoing embodiments related to Form 3, polymorph Form 3 is characterized by or has an X-ray diffraction pattern substantially as shown in FIG. 1A or 1B. In another further embodiment that may be combined with any of the foregoing embodiments related to Form 7, polymorph Form 7 is characterized by or has an X-ray diffraction pattern substantially as shown in FIG. 2A or 2B.

In one aspect, provided is a compound of Formula IA:

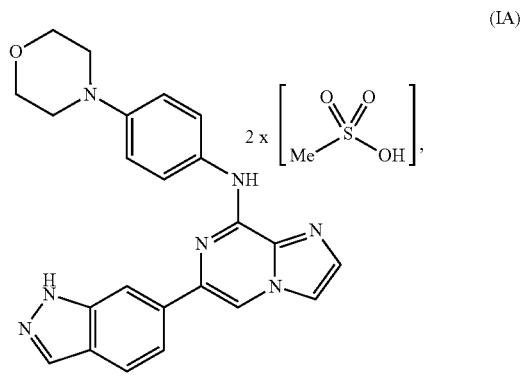

(IA)

or a hydrate thereof. In some embodiments, the compound of Formula (IA), or hydrate thereof, is crystalline.

In another aspect, provided is a polymorph of a monohydrate of a compound of Formula IA:

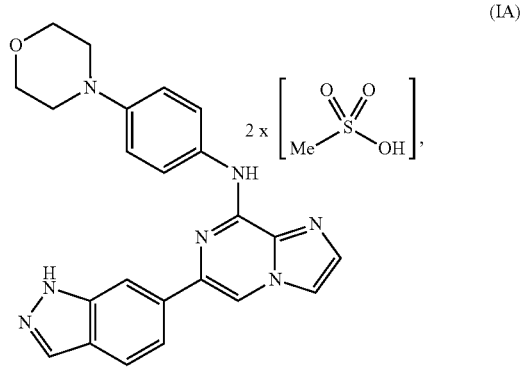

(IA)

having an X-ray diffraction pattern comprising 2θ-reflections (±0.2 degrees) selected from the group consisting of Form 3: 13.8, 16.9, 22.9, and 26.1; and Form 7: 4.9, 9.8, and 26.7.

In some embodiments, an X-ray diffraction pattern of a polymorph of a monohydrate of a compound of Formula IA comprises 2θ-reflections (±0.2 degrees) characteristic of Form 3. In some embodiments, an X-ray diffraction pattern of a polymorph of a monohydrate of a compound of Formula IA comprises 2θ-reflections (±0.2 degrees) characteristic of Form 7. In some embodiments, an X-ray diffraction pattern of polymorph Form 3 is represented in FIG. 1A or 1B. In some embodiments, an X-ray diffraction pattern of polymorph Form 7 is represented in FIG. 2A or 2B.

In some embodiments, a polymorph of the compound of Formula (IA) is a polymorph selected from the group consisting of Form 3 and Form 7; wherein Form 3 has a differential scanning calorimetry profile represented in FIG. 3A, 3B or 3C, and Form 7 has a differential scanning calorimetry profile represented in FIG. 4A, 4B or 4C. In some embodiments, a polymorph of the compound of Formula (IA) is polymorph Form 3 having a differential scanning calorimetry profile represented in FIG. 3A, 3B or 3C and/or an X-ray diffraction pattern represented in FIG. 1A or 1B. In some embodiments, a polymorph of the compound of Formula (IA) is polymorph Form 7 having a differential scanning profile represented in FIG. 4A, 4B or 4C and/or an X-ray diffraction pattern represented in FIG. 2A or 2B.

In another aspect, provided is a polymorph of a compound of Formula IA:

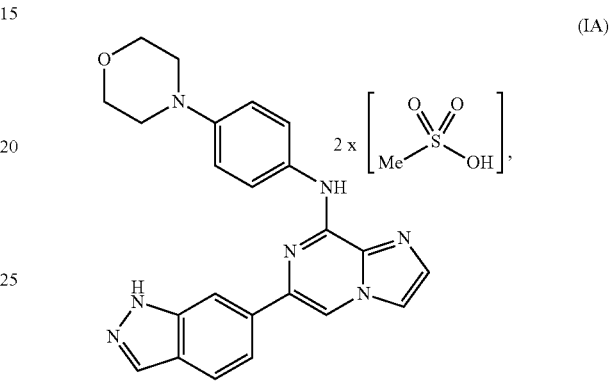

(IA)

or a hydrate thereof,
wherein the polymorph is bioequivalent to the polymorph of any of the foregoing embodiments.

In another aspect, provided is a method of preparing polymorph Form 3 (which is a polymorph of a monohydrate, bis-mesylate salt of the compound of Formula I), comprising adding an amount of polymorph Form 3 seeds and a solvent to polymorph Form 7 (which is a polymorph of a hydrate, bis-mesylate salt of the compound of Formula I) to form a mixture; wherein the method is capable of producing polymorph Form 3. In another aspect, provided is a method of preparing a production scale amount of polymorph Form 3 (which is a polymorph of a monohydrate, bis-mesylate salt of the compound of Formula I), comprising adding an amount of polymorph Form 3 seeds and a solvent to polymorph Form 7 (which is a polymorph of a hydrate, bis-mesylate salt of the compound of Formula I) to form a mixture; wherein the polymorph Form 3 has an X-ray diffraction pattern comprising 2θ-reflections (±0.2 degrees) selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1; and wherein the polymorph Form 7 has an X-ray diffraction pattern comprising 2θ-reflections (±0.2 degrees) selected from the group consisting of A: 4.9, 9.8, and 26.7; B: 15.0 and 18.0; and C: 4.9, 9.8, 15.0, 18.0, and 26.7, and wherein the method is capable of producing a production scale amount of polymorph Form 3. In one variation, the polymorph Form 3 has an X-ray diffraction pattern comprising 2θ-reflections (±0.2 degrees) selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1; and the polymorph Form 7 has an X-ray diffraction pattern comprising 2θ-reflections (±0.2 degrees) at 4.9, 9.8, and 26.7. In another variation, the polymorph Form 3 has an X-ray diffraction pattern comprising 2θ-reflections (±0.2 degrees) selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1; and the polymorph Form 7 has an X-ray diffraction pattern comprising 2θ-reflections (±0.2 degrees) at 4.9 and 9.8, and 2θ-reflections (±0.4 degrees) at 26.7. In yet another variation, the polymorph Form 3 has an X-ray diffraction pattern comprising 2θ-reflections (±0.2 degrees) selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1; and the polymorph Form 7 has an X-ray diffraction pattern comprising 2θ-reflections (±0.2 degrees) at 4.9 and 9.8, and 2θ-reflections (±0.3 degrees at 26.7. In some embodiments, the method further comprises isolating polymorph Form 3. In some embodiments, the solvent comprises acetone. In some embodiments, the solvent comprises acetone and water. In some embodiments, the ratio of water to acetone is about 1:15 to about 1:40; or about 1:18 to about 1:22. In some embodiments, the method further comprises agitating the mixture; heating the mixture; and cooling the mixture to provide polymorph Form 3. It is understood that the methods detailed herein may also be carried out on a non-production scale, such as a method of preparing a less than production scale amount of polymorph Form 3.

In yet another aspect, provided is a method of preparing a production scale amount of polymorph Form 3, which is a polymorph of a monohydrate of a compound of Formula IA:

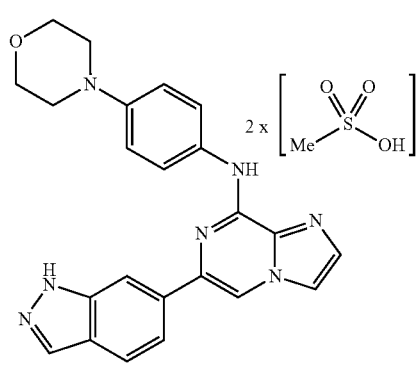

(IA)

comprising adding an amount of polymorph Form 3 seeds and at least one solvent to polymorph Form 7, which is a polymorph of a hydrate of a compound of Formula IA, to form a mixture; and isolating polymorph Form 3 produced. In some embodiments, the at least one solvent is acetone. In some embodiments, the at least one solvent further comprises water. In some embodiments, the at least one solvent is acetone and further comprises water. In some embodiments, the ratio of water to acetone is about 1:15 to about 1:40. In other embodiments, the ratio of water to acetone is about 1:18 to about 1:22. In some embodiments, the method further comprises agitating the mixture; heating the mixture; and cooling the mixture to provide polymorph Form 3.

In yet another aspect, provided is a method of preparing polymorph Form 3, which is polymorph of a monohydrate, bis-mesylate salt of a compound of Formula I, comprising: adding a solvent to a compound of Formula I to form a mixture; adding an amount of methanesulfonic acid to the mixture; heating the mixture; adding an amount of polymorph Form 3 seeds to the mixture; and cooling the mixture; wherein the method is capable of producing polymorph Form 3. In yet another aspect, provided is a method of preparing a production scale amount of polymorph Form 3, which is a polymorph of a monohydrate, bis-mesylate salt of a compound of Formula I, comprising: adding a solvent to a compound of Formula I to form a mixture; adding an amount of methanesulfonic acid to the mixture; heating the mixture; adding an amount of polymorph Form 3 seeds to the mixture; and cooling the mixture; wherein an X-ray diffraction pattern of the polymorph Form 3 comprises 2θ-reflections (±0.2 degrees) selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1. In some variations, the mixture formed from adding solvent to the compound of Formula I may be a heterogeneous mixture. In one embodiment, the method further comprises isolating the polymorph Form 3. In another embodiment, the amount of methanesulfonic acid is between 1.8 and 3.2 molar equivalents, between 1.8 and 3.0 molar equivalents, between 1.95 and 3.0 molar equivalents, or between 2.0 and 2.4 molar equivalents with respect to one molar equivalent of the compound of Formula I. It is understood that the methods detailed herein may also be carried out on a non-production scale, such as a method of preparing a less than production scale amount of polymorph Form 3.

In one aspect, provided is a method of preparing a production scale amount of polymorph Form 3, which is a polymorph of a monohydrate, bis-mesylate salt of a compound of Formula I:

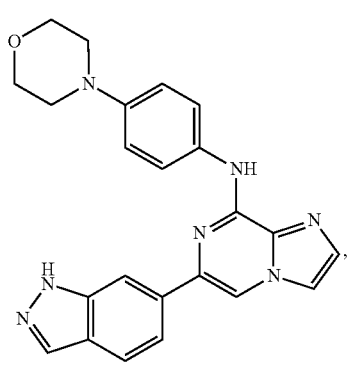

(I)

comprising adding at least one solvent to the compound of Formula I to form a mixture; adding an amount of methanesulfonic acid to the mixture; heating the mixture; adding an amount of polymorph Form 3 seeds to the mixture; cooling the mixture; and recovering the polymorph Form 3 produced. In some embodiments, the amount of methanesulfonic acid is between 2.0 and 2.4 molar equivalents with respect to one molar equivalent of the compound of Formula I. In yet another aspect, provided is polymorph Form 3, which is a polymorph of a monohydrate, bis-mesylate salt of a compound of Formula I, prepared by a method of any of the foregoing embodiments. In yet another aspect, provided is a production scale amount of polymorph Form 3, which is a polymorph of a monohydrate, bis-mesylate salt of a compound of Formula I, prepared by a production scale method of the foregoing embodiments.

In one aspect, provided is a method of preparing polymorph Form 7, which is a polymorph of a hydrate, bis-mesylate salt of a compound of Formula I:

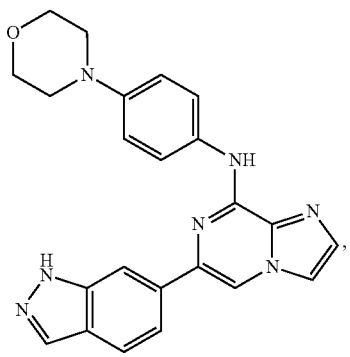

(I)

comprising adding at least one solvent to the compound of Formula I to form a mixture; adding an amount of methanesulfonic acid to the mixture; heating the mixture; and cooling the mixture to provide polymorph Form 7. In some embodiments, the method further comprises isolating polymorph Form 7. In yet another aspect, provided is polymorph Form 7, which is a polymorph of a hydrate, bis-mesylate salt of a compound of Formula I, prepared by a method of any of the foregoing embodiments.

In another aspect, provided is a polymorph of a hydrate, bis-mesylate salt of a compound of Formula I prepared by a method of any of the foregoing embodiments. In another aspect, provided is a polymorph of a monohydrate, bis-mesylate salt of a compound of Formula I prepared by a method of any of the foregoing embodiments.

In one aspect, provided is a polymorph of a bis-mesylate salt of a compound of Formula I, or a hydrate thereof, wherein the polymorph is bioequivalent to the bis-mesylate salt of a compound of Formula I, or a hydrate thereof, of any of the foregoing embodiments.

In another aspect, provided is polymorph Form 3, which is a polymorph of a monohydrate of a compound of Formula IA:

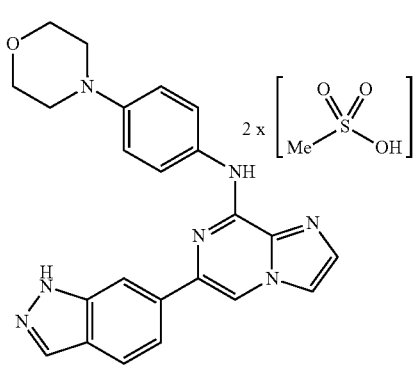

(IA)

prepared by any of the foregoing methods.

In another aspect, provided is a pharmaceutical composition comprising a bis-mesylate salt of a compound of Formula I, a hydrate thereof, or a polymorph according to any of the foregoing embodiments.

In yet another aspect, provided is an article of manufacture comprising a bis-mesylate salt of a compound of Formula I, or a hydrate thereof; or a polymorph or a pharmaceutical composition according to any of the foregoing embodiments.

In one aspect, provided is a method of treating a condition in a subject in need thereof, comprising administering to the subject a bis-mesylate salt of a compound of Formula I, or a hydrate thereof; or a polymorph of the bis-mesylate salt of a compound of Formula I, or a hydrate thereof, or a pharmaceutical composition comprising any of the foregoing embodiments, wherein the condition is selected from the group consisting of cancer and autoimmune disease. In some embodiments, the condition is selected from the group consisting of acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the condition is non-Hodgkin's lymphoma. In one variation, the NHL is indolent non-Hodgkin's lymphoma (iNHL). In another variation, the iNHL is refractory iNHL. In yet another variation, the iNHL is non-FL iNHL. In other embodiments, the condition is selected from the group consisting of asthma, rheumatoid arthritis, multiple sclerosis, and lupus. In some of the foregoing embodiments, the subject is human.

DESCRIPTION OF THE FIGURES

FIGS. 2A and 2B are exemplary XRPD patterns of polymorph Form 7. The XRPD pattern in FIG. 2B was obtained at 25° C. and 53% relative humidity (RH).

DETAILED DESCRIPTION

Figure 1A:
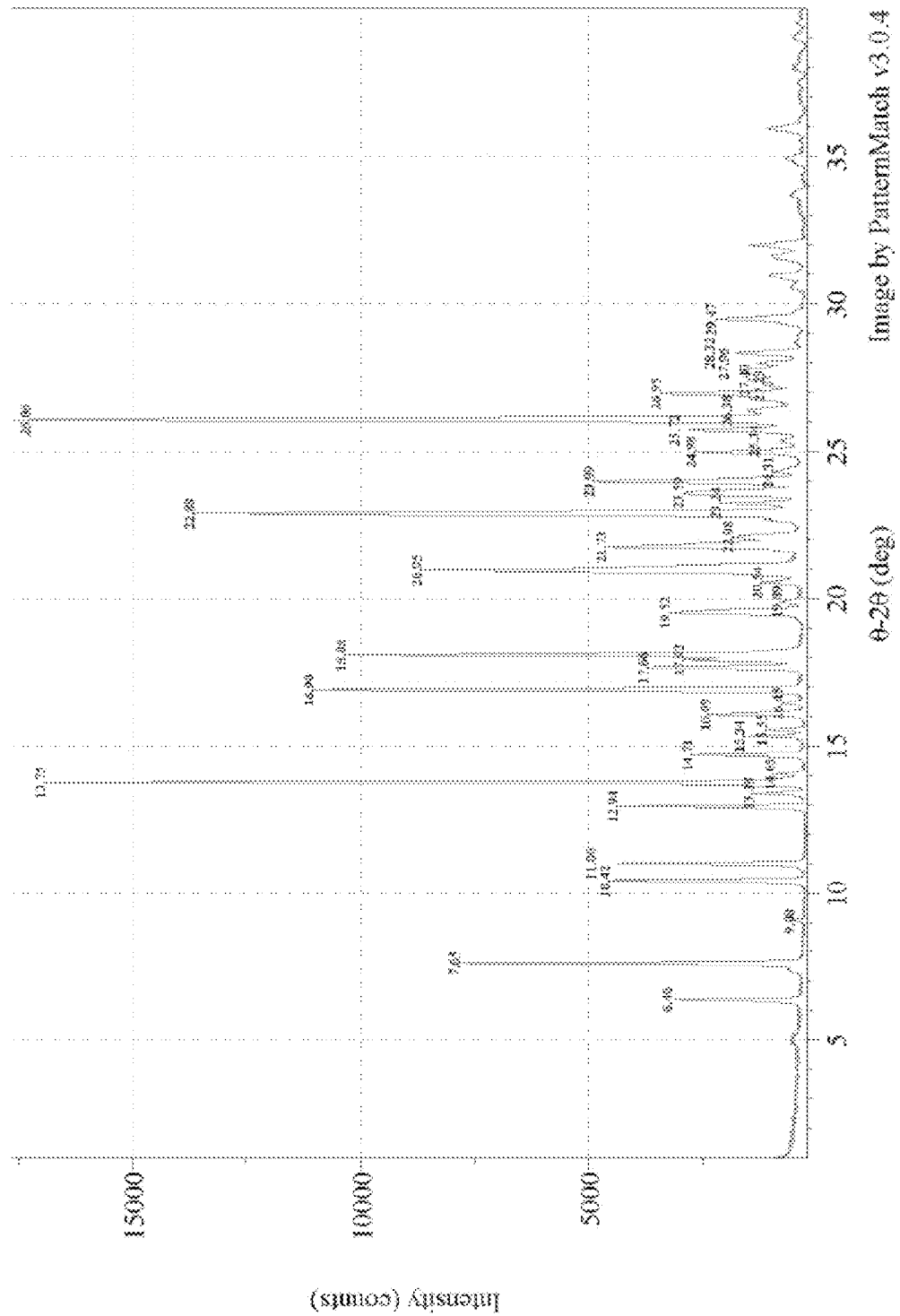
FIGS. 1A and 1B are exemplary X-ray powder diffraction pattern (XRPD) patterns of polymorph Form 3.

The following examples are included to illustrate embodiments of the disclosure, and are not intended to limit the scope of the disclosure. It should be appreciated by those of skill in the art that the techniques disclosed herein represent techniques that apply in the practice of the disclosure. Those of skill in the art would appreciate that, in light of the present disclosure, changes can be made in the examples herein without departing from the spirit and scope of the disclosure.

As used in the present specification, the following words and phrases are generally intended to have the meanings as set forth below, except to the extent that the context in which they are used indicates otherwise.

Terms used in the singular will also include the plural. For example, "a" means one or more unless indicated otherwise.

The use of the term "about" includes and describes the value or parameter per se. For example, "about x" includes and describes "x" per se. In some embodiments, the term "about" when used in association with a measurement, or used to modify a value, a unit, a constant, or a range of values, refers to variations of ±10%. For example, "about 2:8" in some embodiments includes 1.8-2.2:7.2-8.8.

The use of the term "adding" does not limit the order, method or how the materials being added are combined, unless indicated otherwise. For instance, "adding A to B" may also describe "adding B to A". Furthermore, "adding A and B to C" may also describe the various other combinations such as "adding A to B and C", "adding A and C to B", "adding B to A and C", "adding B and C to A", and "adding C to A and B".

Provided are pharmaceutically acceptable salts of the compound of Formula I:

(I)

or a hydrate thereof. In some aspects, the pharmaceutically acceptable salt of the compound of Formula I is a mesylate salt, or a hydrate thereof. In one variation, the pharmaceutically acceptable salt of the compound of Formula I is a bis-mesylate salt, or a hydrate thereof.

In some embodiments, a bis-mesylate salt, or a hydrate thereof, of a compound of Formula I is provided. It should be understood that "bis-mesylate salt" may also be referred to herein as "bis-MSA salt". In certain embodiments, a hydrate, bis-mesylate salt of a compound of Formula I is provided. In another embodiment, a monohydrate, bis-mesylate salt of a compound of Formula I is provided. In yet another embodiment, a polymorph of any of the foregoing is provided. In one variation, Form 3, which is a polymorph of a monohydrate, bis-mesylate salt of a compound of Formula I, is provided. In another variation, Form 7, which s a polymorph of a hydrate, bis-mesylate salt of a compound of Formula I, is provided.

The bis-mesylate salt of a compound of Formula I may be depicted herein in various ways. For example, in one variation, a bis-mesylate salt may be represented by Formula IA:

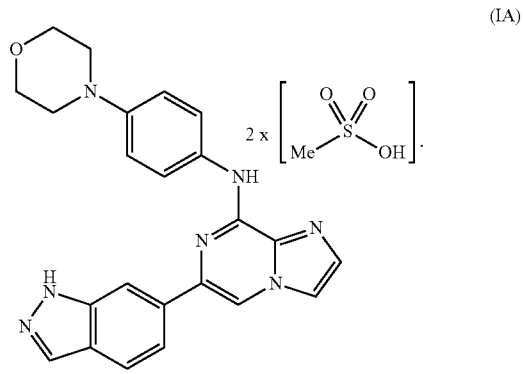

(IA)

One of skill in the art would understand that when a bis-mesylate salt of the compound of Formula I is depicted as Formula IA above, the ionic form (e.g., the cationic form of the compound of formula I and the anionic form of the methanesulfonic acid) is intended. Without wishing to be bound by any theory, in another variation, a bis-mesylate salt may be represented by Formula IB:

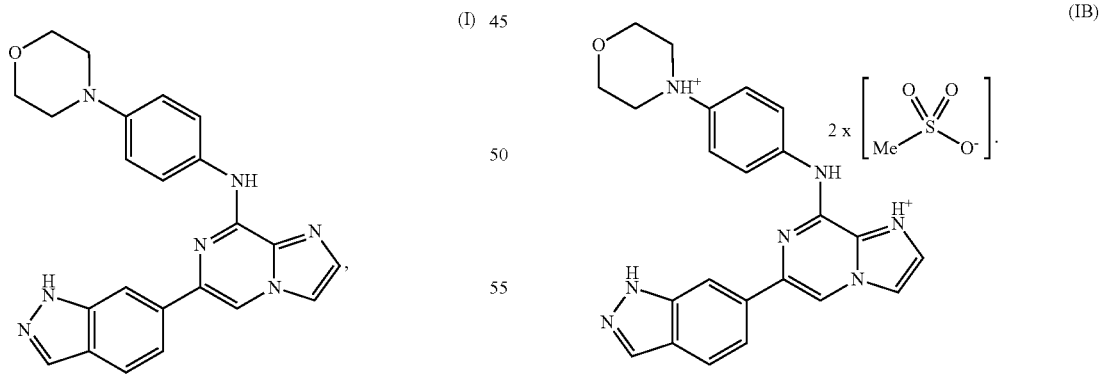

(IB)

In some embodiments, the bis-mesylate salt, as depicted by Formula IA or IB, may be a hydrate thereof. For example, in one embodiment, the bis-mesylate salt, as depicted by Formula IA or IB, may be a monohydrate, bis-mesylate salt. Without wishing to be bound by any theory, a monohydrate, bis-mesylate salt of a compound of Formula I may also be represented by Formula IC:

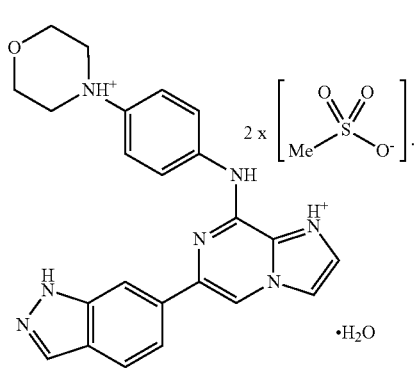

(IC)

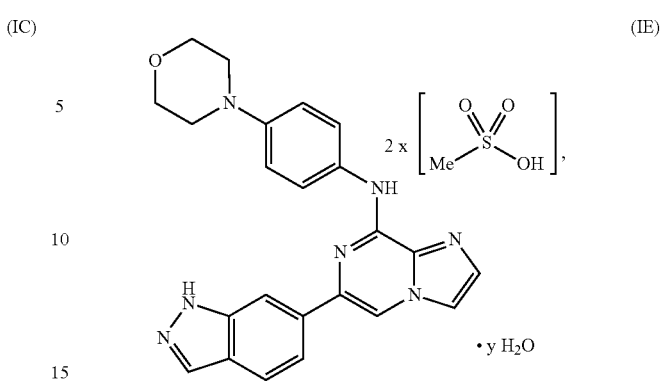

(IE)

The monohydrate, bis-mesylate salt of a compound of Formula I has increased solubility at higher pH compared to the mono-mesylate salt of a compound of Formula I. It should be understood that "mono-mesylate salt" may also be referred to herein as "mono-MSA salt". The bis-mesylate salt of a compound of Formula I in comparison to the mono-mesylate salt of a compound of Formula I provides increased bioavailability and the ability to offset the effect of acid reducing agents on the pharmacokinetic (PK) profile of the compound of Formula I.

Without wishing to be bound by any theory, in other embodiments, a hydrate of a bis-mesylate salt of a compound of Formula I may be represented by Formula ID:

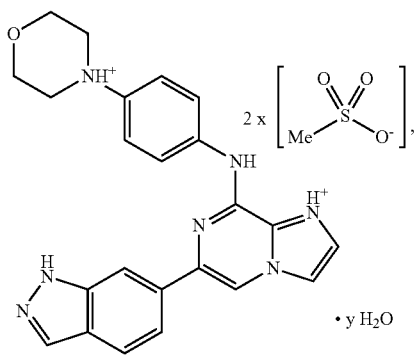

(ID)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 1, the compound of Formula is a monohydrate, bis-mesylate salt. When y is 2, the compound of Formula ID is a bis-hydrate, bis-mesylate salt. Thus, variable "y" in Formula ID represents the variability of the water content in the hydrate of the bis-mesylate salt.

Without wishing to be bound by any theory, in another variation, the hydrate, bis-mesylate salt may be represented by Formula IE:

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 2, the compound of Formula IE is a bis-hydrate, bis-mesylate salt. In other variations, y is a non-integer.

In yet other embodiments, a hydrate of a bis-mesylate salt of a compound of Formula I may have varying amounts of water.

Provided herein are polymorphs of a mesylate salt of a compound of Formula I, or a hydrate thereof. In certain aspects, provided are polymorphs of a bis-mesylate salt of a compound of Formula I, or a hydrate thereof. In certain variations, provided are polymorphs of a monohydrate, bis-mesylate salt of a compound of Formula I. In one aspect, a polymorph of a compound of Formula IA or IB, or a hydrate thereof, is provided. In another aspect, a polymorph of a compound of Formula IC, ID or IE is provided. The polymorphs described herein may be characterized by a variety of solid state analytical data, including for example, by X-ray powder diffraction pattern (XRPD), differential scanning calorimetry (DSC) and thermal gravimetric analysis (TGA).

Polymorph Form 3

The therapeutic use and commercialization of a bis-mesylate salt of a compound of Formula I, or a hydrate thereof (e.g., a compound of Formula IA or IB, or a hydrate thereof; or a compound of IC or ID) involves the development of a bioavailable and stable compound. As one of skill in the art would appreciate, variations in the crystal structure of a pharmaceutical drug substance may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product, particularly when formulated in a solid oral dosage form.

In one aspect, provided is polymorph Form 3, which is a polymorph of a monohydrate, bis-mesylate salt of a compound of Formula I. In certain variations, Form 3 is crystalline. Thus, in certain aspects, provided is polymorph Form 3, which is a polymorph of a monohydrate of a compound of Formula IA:

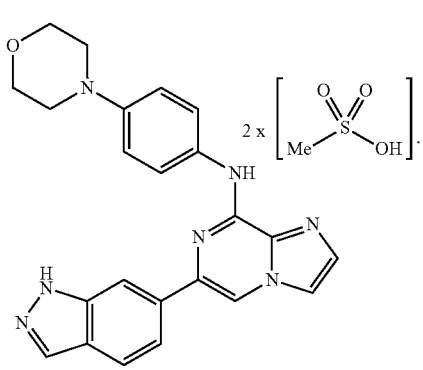

(IA)

In some embodiments, polymorph Form 3 is a crystalline form of a monohydrate, bis-mesylate salt of Formula IA. One of skill in the art would understand that when the bis-mesylate salt is depicted as Formula IA above, the ionic form (e.g., the cationic form of the compound of Formula I and the anionic form of the methanesulfonic acid) is intended.

In other aspects, provided is polymorph Form 3, which is a polymorph of a monohydrate of a compound of Formula IB:

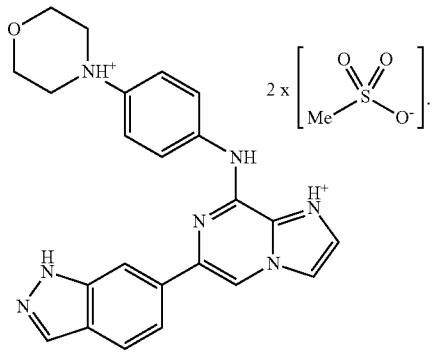

(IB)

In some embodiments, polymorph Form 3 is a crystalline form of a monohydrate, bis-mesylate salt of Formula IB.

In certain aspects, provided is polymorph Form 3, which is a polymorph of a compound of Formula IC:

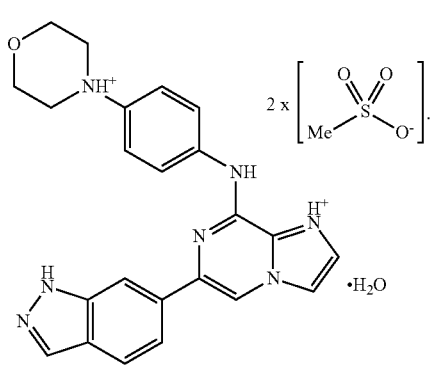

(IC)

In some embodiments, polymorph Form 3 is a crystalline form of a monohydrate, bis-mesylate salt of a compound of Formula I.

In yet other aspects, provided is polymorph Form 3, which is a polymorph of a compound of Formula ID:

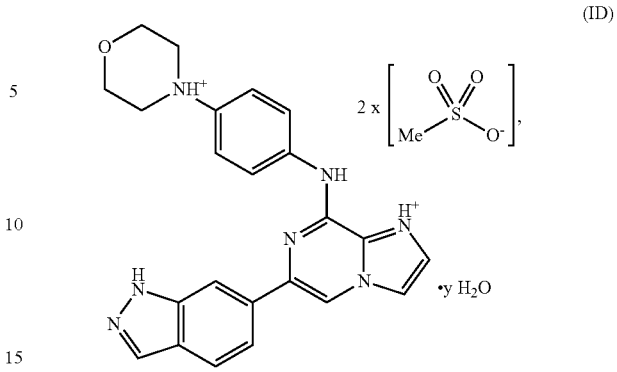

(ID)

wherein y is 1 for a monohydrate of the bis-mesylate salt. In some embodiments, polymorph Form 3 is a crystalline form of a monohydrate, bis-mesylate salt of Formula ID.

In yet other aspects, provided is polymorph Form 3, which is a polymorph of a compound of Formula IE:

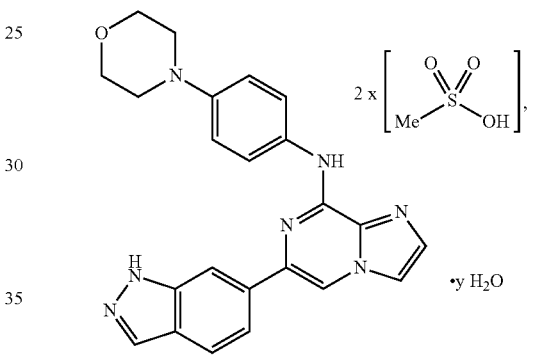

(IE)

wherein y is 1 for a monohydrate of the bis-mesylate salt. In some embodiments, polymorph Form 3 is a crystalline form of a monohydrate, bis-mesylate salt of Formula IE. Throughout the present disclosure, it is understood that reference to "polymorph Form 3", "Form 3", "Form III", "bis-MSA salt of polymorph Form 3", or "bis-MSA salt Form 3" refers to the polymorph Form 3, which is a polymorph of a monohydrate, bis-mesylate salt of the compound of Formula I. As discussed above, the bis-mesylate salt may be depicted in various ways, including as a compound of Formula IA or IB. Furthermore, the monohydrate, bis-mesylate salt may be depicted by Formula IC, ID (wherein y is 1) or IE (wherein y is 1).

Figure 1B:
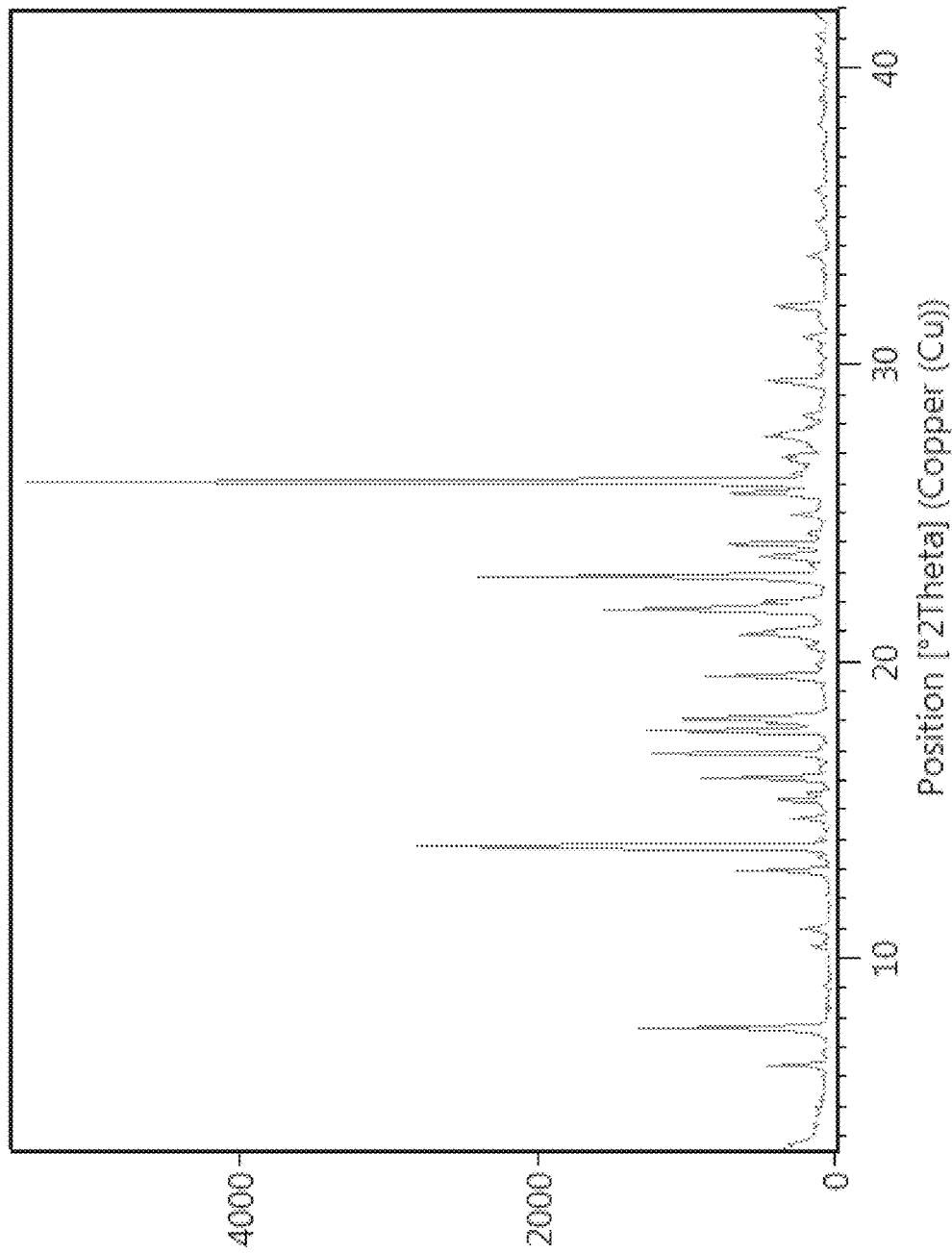

In some variations, polymorph Form 3 is characterized by or has an X-ray powder diffraction (XRPD) pattern substantially as shown in FIG. 1A or 1B. It should be understood, however, that relative intensities and assignments of the peaks of polymorphic forms depicted in the figures can vary depending on a number of factors, including sample preparation, mounting, and the instrument and analytical procedure and settings used to obtain the spectrum. As such, the peaks observed in the figures and assignments listed herein (including in FIGS. 1A and 1B for polymorph Form 3) are intended to encompass variations of plus or minus 0.2 degrees 2θ.

In other variations, polymorph Form 3 is characterized by or has an X-ray diffraction (XRPD) pattern comprising 2θ-reflections (±0.2 degrees): 13.8, 16.9, 22.9, and 26.1. In some embodiments, polymorph Form 3 is characterized by or has an X-ray diffraction (XRPD) pattern comprising at least one or more; at least two or more; or at least three or more of the 2θ-reflections (±0.2 degrees): 13.8, 16.9, 22.9, and 26.1. In some embodiments, polymorph Form 3 is characterized by or has an X-ray diffraction comprising 2θ-reflections (±0.2 degrees): 7.7, 12.9, 17.7, and 18.1. In some embodiments, polymorph Form 3 is characterized by or has an X-ray diffraction pattern comprising 2θ-reflections (±0.2 degrees) at 7.7, 12.9, 13.8, 16.9, 17.7, 18.1, 22.9, and 26.1. In some embodiments, polymorph Form 3 is characterized by or has an X-ray diffraction (XRPD) pattern comprising at least three or more; at least four or more; or at least five or more of the 2θ-reflections (±0.2 degrees): 7.7, 12.9, 13.8, 16.9, 17.7, 18.1, 22.9, and 26.1. When describing the 2θ-reflections in the X-ray diffraction pattern (e.g., of Form 3), it should be understood that ±0.2 degrees can also be expressed as "plus or minus 0.2 degrees 2θ".

Figure 3A:
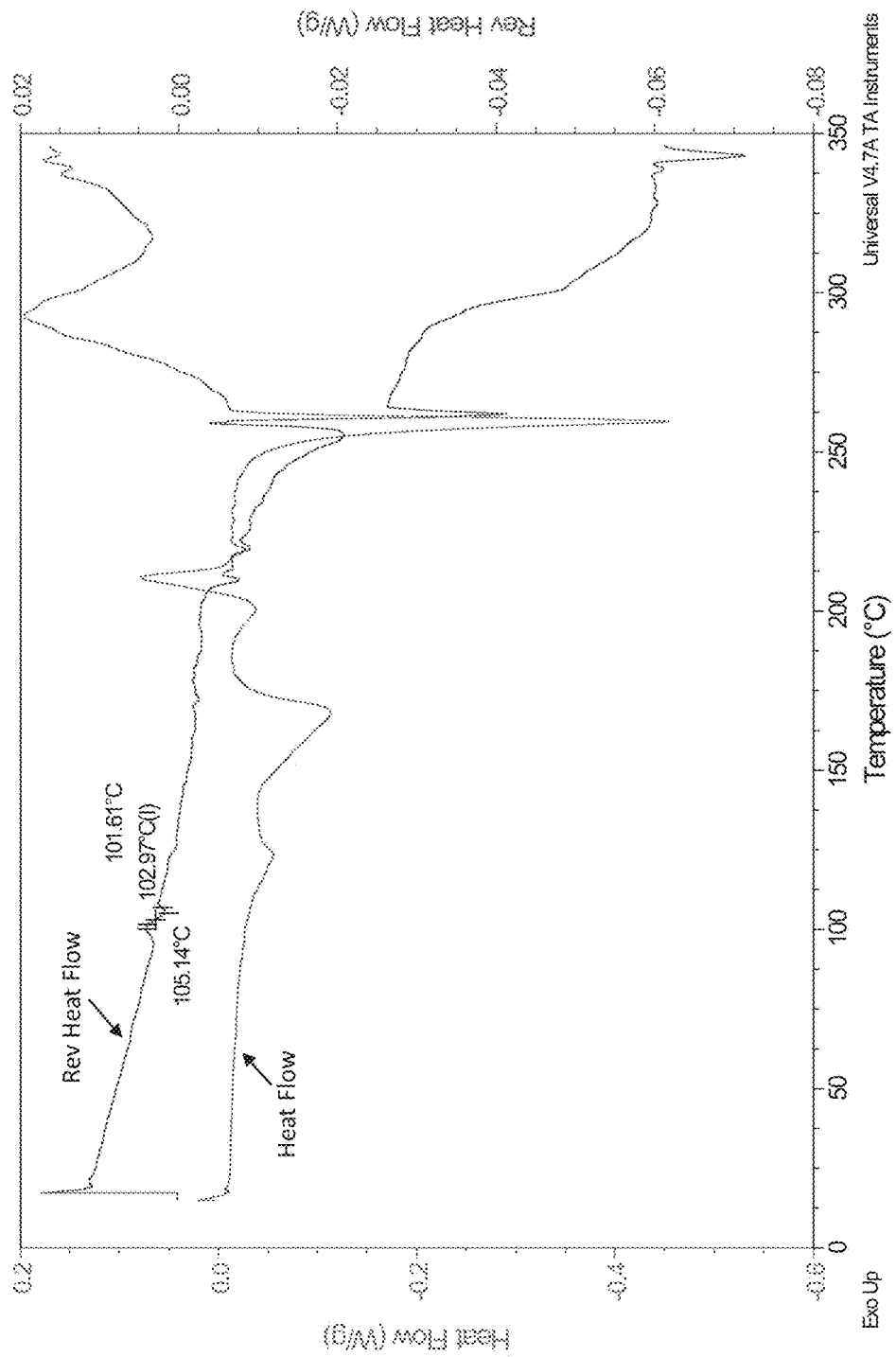
FIG. 3A is an exemplary differential scanning calorimetry (DSC) plot of polymorph Form 3.
Figure 3B:
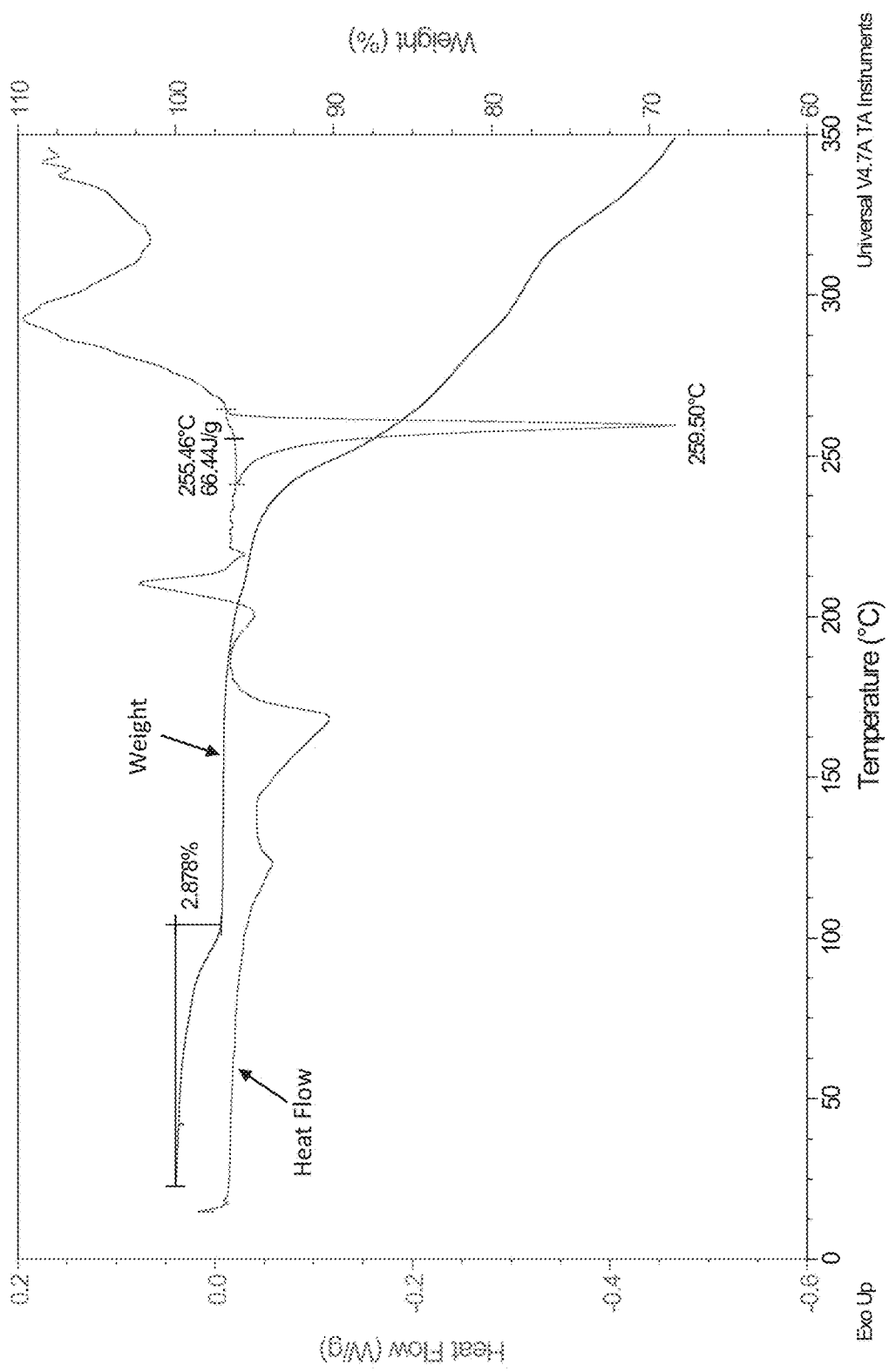
FIGS. 3B and 3C are exemplary DSC and thermal gravimetric analysis (TGA) plots of polymorph Form 3.
Figure 3C:
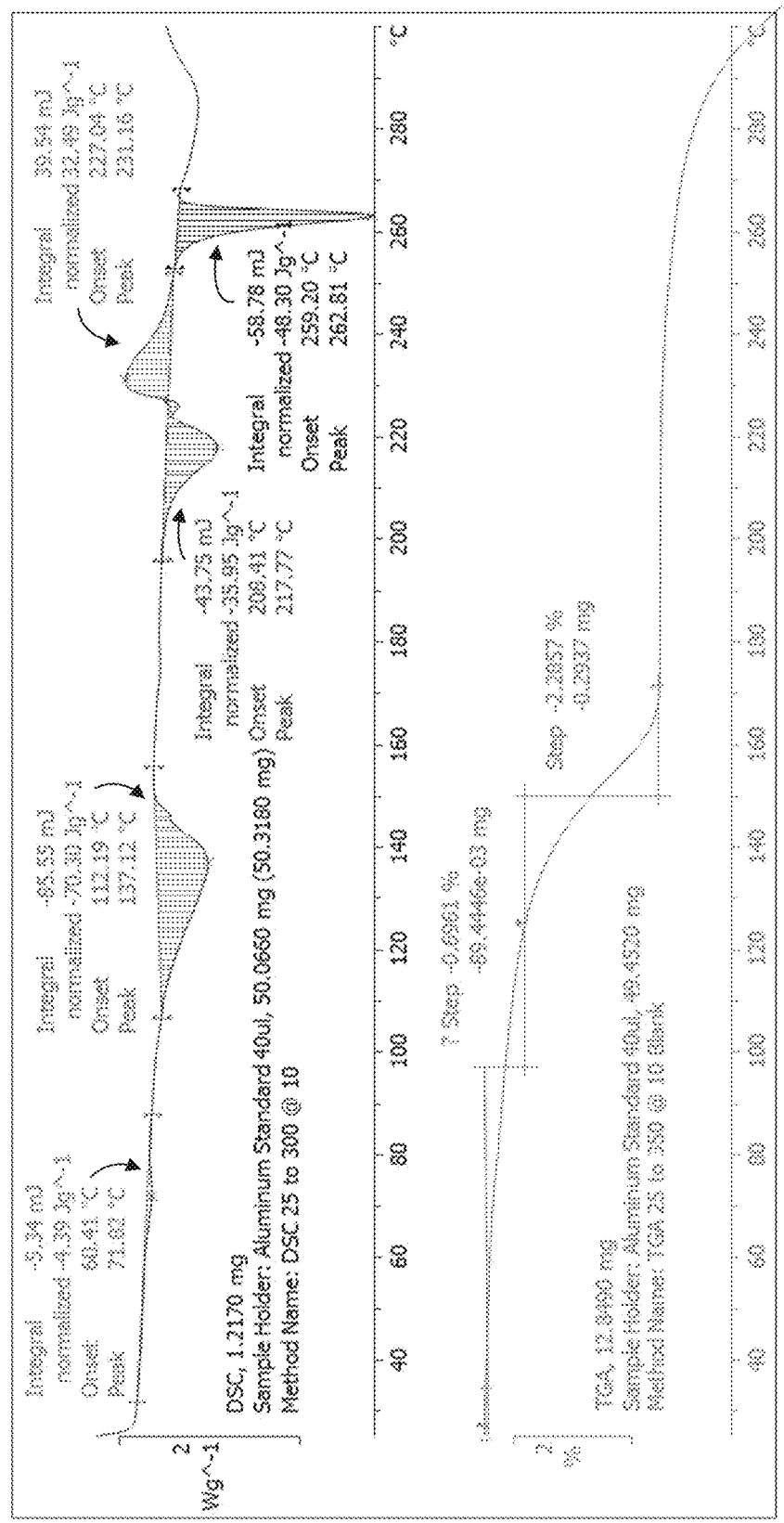

In some embodiments, polymorph Form 3 is characterized by or has a DSC plot substantially as shown in FIG. 3A, 3B or 3C.

In some embodiments, the term "substantially as shown in" when referring to an X-ray powder diffraction pattern or a differential scanning calorimetry profile means that a pattern or profile that is not necessarily identical to those depicted herein, but that falls within the limits of experimental error or deviations, when considered by one of ordinary skill in the art, would be encompassed.

In certain variations, polymorph Form 3 may also have one or more, two or more, three or more, four or more, five or more, or all of the following properties (i)-(vi):
(i) a unit cell as determined by crystal X-ray crystallography of the following dimensions: a=8.7831(6) Å; b=11.8484(8) Å; c=14.2485(10) Å; α=98.108(6)°; β=100.955(6)°; and γ=98.861(6)°;
(ii) a triclinic crystal system;
(iii) a P-1 space group;
(iv) a volume of 1416.05(17) Å³;
(v) a Z-value of 2; and
(vi) a density of 1.458 Mg/m³.

Polymorph Form 7

In another aspect, provided is polymorph Form 7, which is a polymorph of a hydrate, bis-mesylate salt a compound of Formula I. In some variations, provided is polymorph Form 7, which is a polymorph of a hydrate of a compound of Formula IA:

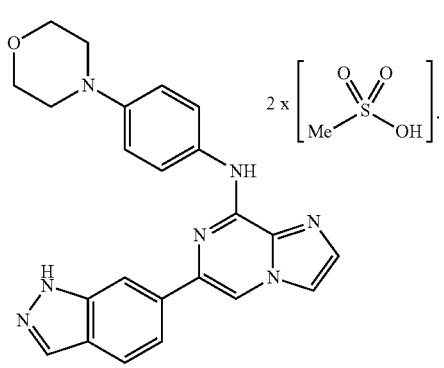

(IA)

One of skill in the art would understand that when the bis-mesylate salt is depicted as Formula IA above, the ionic form (e.g., the cationic form of the compound of Formula I and the anionic form of the methanesulfonic acid) is intended.

In other variations, provided is polymorph Form 7, which is a polymorph of a compound of Formula IB:

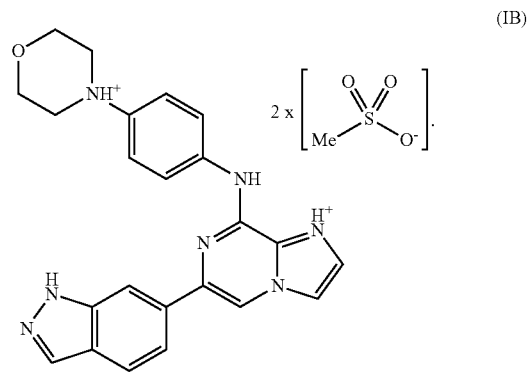

(IB)

In some embodiments, polymorph Form 7 is a variable hydrate of a bis-mesylate salt of a compound of Formula I. A variable hydrate may have varying water content. For example, in one embodiment, polymorph Form 7 is a polymorph of a bis-mesylate salt having between 1.8% to 10% water. Various factors may affect the water content of polymorph Form 7, including, for example, the relative humidity conditions at which polymorph Form 7 is characterized.

In some variations, polymorph Form 7 is a polymorph of a hydrate, bis-mesylate salt that comprises at least two molecules of water. In one variation, polymorph Form 7 may be depicted by Formula ID:

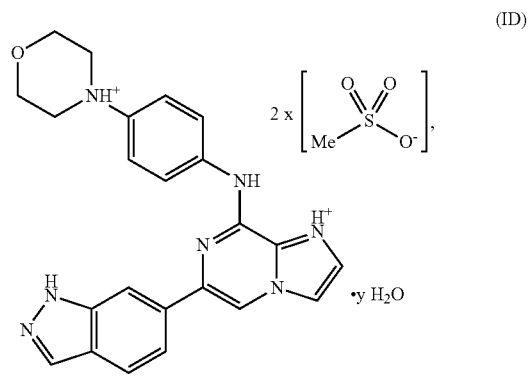

(ID)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 2, the compound of Formula ID is a bis-hydrate, bis-mesylate salt. In other variations, y is a non-integer.

In some variations, polymorph Form 7 is a polymorph of a hydrate, bis-mesylate salt that comprises at least two molecules of water. In one variation, polymorph Form 7 may be depicted by Formula IE:

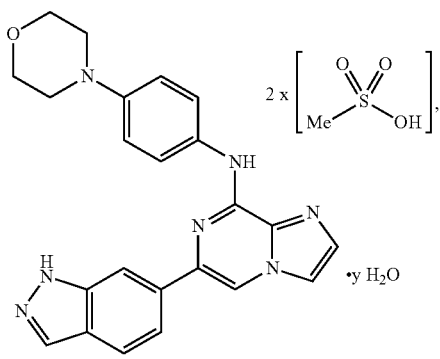

(IE)

wherein y is at least 0.5. In some variations, y is at least 1, at least 1.5, at least 2, at least 2.5, at least 3, or at least 4, or between 0.5 and 5, between 0.5 and 4, between 0.5 and 2, between 0.5 and 1.5, or about 0.5, about 1, about 1.5, about 2, about 3, or about 4. In certain variations, y is an integer. For example, when y is 2, the compound of Formula IE is a bis-hydrate, bis-mesylate salt. In other variations, y is a non-integer.

Throughout the application it is understood that reference to "polymorph Form 7", "Form 7", "Form VII", "bis-MSA salt of polymorph Form 7", or "bis-MSA salt Form 7" refers to the polymorph Form 7, which is a polymorph of a hydrate, bis-mesylate salt of a compound of Formula I. As discussed above, a bis-mesylate salt may be depicted in various ways, including as a compound of Formula IA or IB. Furthermore, a bis-mesylate salt having varying water content may be depicted by Formula ID.

In some variations, polymorph Form 7 is characterized by or has an X-ray diffraction (XRPD) pattern comprising 2θ-reflections (±0.2 degrees) at 4.9 and 9.8, and 2θ-reflections (±0.4 degrees) at 26.7. In certain variations, polymorph Form 7 is characterized by or has an X-ray diffraction (XRPD) pattern comprising 2θ-reflections (±0.2 degrees) at 4.9 and 9.8, and 2θ-reflections (±0.3 degrees) at 26.7. In certain variations, polymorph Form 7 is characterized by or has an X-ray diffraction (XRPD) pattern comprising 2θ-reflections (±0.2 degrees): 4.9, 9.8, and 26.7.

In some variations, polymorph Form 7 is characterized by or has an X-ray diffraction (XRPD) pattern comprising at least one or more; or at least two or more of 2θ-reflections at 4.9 (±0.2 degrees), 9.8 (±0.2 degrees), and 26.7 (±0.4 degrees). In some variations, polymorph Form 7 is characterized by or has an X-ray diffraction (XRPD) pattern comprising at least one or more; or at least two or more of 2θ-reflections at 4.9 (±0.2 degrees), 9.8 (±0.2 degrees), and 26.7 (±0.3 degrees). In certain variations, polymorph Form 7 is characterized by or has an X-ray diffraction (XRPD) pattern comprising at least one or more; or at least two or more of 2θ-reflections (±0.2 degrees): 4.9, 9.8, and 26.7.

In other embodiments, polymorph Form 7 is characterized by or has an X-ray diffraction pattern comprising 2θ-reflections (±0.2 degrees): 15.0 and 18.0. In some embodiments, polymorph Form 7 is characterized by or has an X-ray diffraction pattern comprising 2θ-reflections (±0.2 degrees) at 4.9, 9.8, 15.0 and 18.0, and 2θ-reflections (±0.4 degrees) at 26.7. In some embodiments, polymorph Form 7 is characterized by or has an X-ray diffraction pattern comprising 2θ-reflections (±0.2 degrees) at 4.9, 9.8, 15.0 and 18.0, and 2θ-reflections (±0.3 degrees) at 26.7. In some embodiments, polymorph Form 7 is characterized by or has an X-ray diffraction pattern comprising 2θ-reflections (±0.2 degrees) at 4.9, 9.8, 15.0, 18.0, and 26.7.

In other embodiments, polymorph Form 7 is characterized by or has an X-ray diffraction (XRPD) pattern comprising at least three or more; at least four or more; or each of the 2θ-reflections at 4.9 (±0.2 degrees), 9.8 (±0.2 degrees), 15.0 (±0.2 degrees), 18.0 (±0.2 degrees), and 26.7 (±0.4 degrees). In some embodiments, polymorph Form 7 is characterized by or has an X-ray diffraction (XRPD) pattern comprising at least three or more; at least four or more; or each of the 2θ-reflections at 4.9 (±0.2 degrees), 9.8 (±0.2 degrees), 15.0 (±0.2 degrees), 18.0 (±0.2 degrees), and 26.7 (±0.3 degrees). In some embodiments, polymorph Form 7 is characterized by or has an X-ray diffraction (XRPD) pattern comprising at least three or more; at least four or more; or each of the 2θ-reflections (±0.2 degrees) at 4.9, 9.8, 15.0, 18.0, and 26.7.

When describing the 2θ-reflections in the X-ray diffraction pattern (e.g., of Form 7), it should be understood that ±0.2 degrees, ±0.3 degrees, and ±0.4 degrees can also be expressed as "plus or minus 0.2 degrees 2θ", "plus or minus 0.3 degrees 2θ", and "plus or minus 0.4 degrees 2θ", respectively.

Figure 2A:
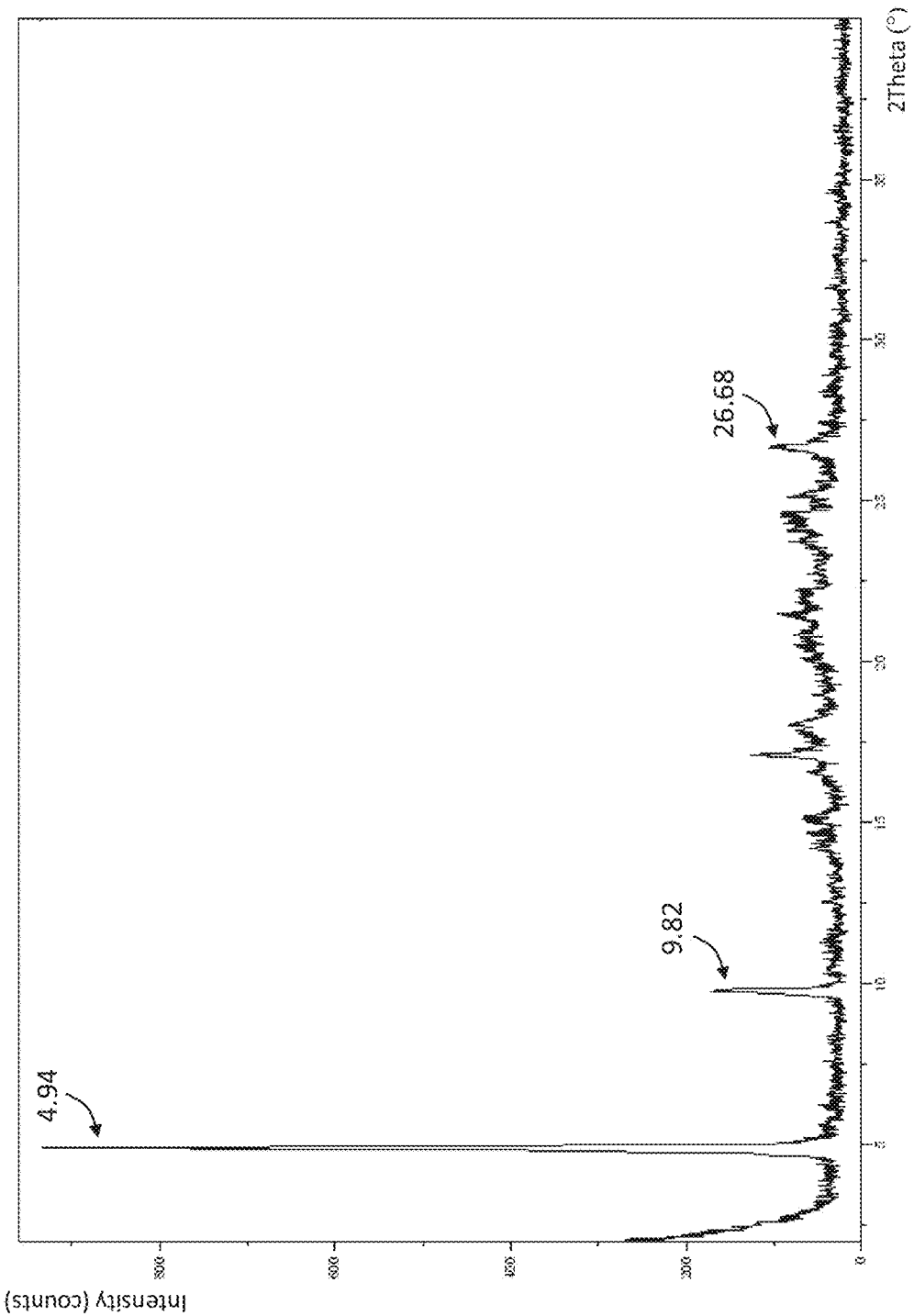

In some variations, polymorph Form 7 is also characterized by or has an XRPD pattern substantially as shown in FIG. 2A or 2B. It should be understood, however, that relative intensities and assignments of the peaks of polymorphic forms depicted in the figures can vary depending on a number of factors, including sample preparation, mounting, and the instrument and analytical procedure and settings used to obtain the spectrum. As such, the peak observed in the figures and assignments listed herein (including in FIGS. 2A and 2B for polymorph Form 7) are intended to encompass variations of plus or minus 0.2 degrees 2θ. Further, in certain instances, the XRPD pattern of polymorph Form 7 may be moisture-dependent or vary based on the relative humidity at which Form 7 is characterized. For example, the XRPD in FIG. 2B was obtained at 25° C. and 53% relative humidity (RH).

In some embodiments, polymorph Form 7 is provided as a compound intermediate in the preparation of polymorph Form 3. In some embodiments, polymorph Form 7 is provided in a reaction mixture comprising polymorph Form 3. In some methods of making Form 3 from a compound of Formula I (which may also be referred to as the free base of Formula I), Form 7 is an intermediate in the reaction pathway.

Crystalline

The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

For example, in one embodiment, polymorph Form 3 is substantially crystalline. In some embodiments, a compound that is substantially crystalline (e.g., polymorph Form 3) has greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition in crystalline form. In other embodiments, a compound that is substantially crystalline (e.g., polymorph Form 3) has no more than about 20%, or no more than about 10%, or no more than about 5%, or no more than about 2% in the amorphous form. In yet other embodiments, a compound that is substantially crystalline (e.g., polymorph Form 3) has no more than about 20%, or no more than about 10%, or no more than about 5%, or no more than about 2% in the non-crystalline form.

Bioequivalents of the Polymorphs

Also provided herein are polymorphs that are bioequivalent to polymorph Form 3. Also provided herein are polymorphs that are bioequivalent to polymorph Form 7. In certain embodiments, bioequivalence between two polymorphs refers to polymorphs having substantially similar bioavailability, substantially similar efficacy, substantially similar safety profiles, or a combination thereof. In yet other embodiments, bioequivalence refers to polymorphs that exhibit substantially similar pharmacokinetic (PK) profiles or therapeutic effects. Bioequivalence may be demonstrated through several in vivo and in vitro methods. These methods may include, for example, pharmacokinetic, pharmacodynamic, clinical and in vitro studies. In some embodiments, bioequivalence can be demonstrated using any suitable pharmacokinetic measures or combination of pharmacokinetic measures known in the art, including loading dose, steady-state dose, initial or steady-state concentration of drug, biological half-life, elimination rate, area under the curve (AUC), clearance, the peak blood or plasma concentration ($C_{max}$), time to peak concentration ($T_{max}$), bioavailability and potency. In some embodiments, bioequivalence is achieved with similar dosing amounts. In alternative embodiments, bioequivalence is achieved with different dosing amounts.

Methods of Preparing Polymorph Form 3

In some embodiments, polymorph Form 3 described herein is prepared by converting Form 7 into Form 3. Convening Form 7 into Form 3 may be facilitated by adding an amount of polymorph Form 3 "seeds" to Form 7. In some embodiments, the methods of preparing Form 3 require forming the polymorph Form 7 as a compound intermediate.

In some embodiments, provided is a method of producing polymorph Form 3, which is a polymorph of a monohydrate, bis-mesylate salt of a compound of Formula comprising:

adding polymorph Form 3 seeds and at least one solvent to polymorph Form 7 (which is a polymorph of a hydrate, bis-mesylate salt of a compound of Formula I) to form a mixture; and producing polymorph Form 3 in the mixture.

In certain embodiments, the method further comprises isolating the polymorph Form 3 from the mixture.

In some embodiments, provided is a method of preparing a production scale amount of polymorph Form 3, which is a polymorph of a monohydrate, bis-mesylate salt of a compound of Formula I, comprising adding an amount of polymorph Form 3 seeds and at least one solvent to polymorph Form 7 (which is a polymorph of a hydrate, bis-mesylate salt of a compound of Formula I) to form a mixture; and isolating polymorph Form 3.

In some embodiments of the methods provided above, the amount of seed is an amount sufficient to initiate nucleation. In some embodiments, the amount of seed is an amount that reduces the time it takes to convert Form 7 to Form 3 compared to conversion without the seed material. In some embodiments, adding an amount of Form 3 seeds reduces Form 7 to Form 3 conversion time by about 10% to about 20%; about 20% to about 50%; about 30% to about 60%; about 40% to about 75%; or about 50% to about 80%, compared to conversion time without the addition of Form 3 seed. In some embodiments, adding an amount of Form 3 seeds reduces Form 7 to Form 3 conversion time by at least about 10%; at least about 25%; at least about 40%; at least about 50%; at least about 60%; at least about 75%; or at least about 80%, compared to conversion time without the addition of Form 3 seeds.

In some embodiments, the methods provide adding an amount of polymorph Form 3 seeds to Form 7. The amount of Form 3 seeds is substantially smaller than the amount of Form 7 to be converted and is also substantially smaller than the amount of Form 3 obtained by the methods described herein. In some embodiments, the amount of Form 3 seeds added to polymorph Form 7 is between 0.01 molar % and 5 molar %. In some embodiments, the amount of Form 3 seeds added to polymorph Form 7 is between 0.01 molar % and 3 molar % of polymorph Form 7. In some embodiments, the amount of Form 3 seeds added to polymorph Form 7 is between 0.01 molar % and 2 molar % of polymorph Form 7. In some embodiments, the amount of Form 3 seeds added to polymorph Form 7 is between 0.01 molar % and 1 molar % of polymorph Form 7. In some embodiments, the amount of Form 3 seeds added to polymorph Form 7 is between 0.1 molar % and 2 molar % of polymorph Form 7. In some embodiments, the amount of Form 3 seeds added to polymorph Form 7 is between 0.1 molar % and 1 molar % of polymorph Form 7. In some embodiments, the amount of Form 3 seeds added to polymorph Form 7 is about 1 molar % of polymorph Form 7.

In some embodiments, the amount of Form 3 seeds added to polymorph Form 7 is between 0.001 and 0.1 weight percent of polymorph Form 7. In some embodiments, the amount of Form 3 seeds added to polymorph Form 7 is between 0.01 and 0.1 weight percent of polymorph Form 7. In some embodiments, the amount of Form 3 seeds added to polymorph Form 7 is between 0.01 and 0.08 weight percent of polymorph Form 7. In some embodiments, the amount of Form 3 seeds added to polymorph Form 7 is about 0.015 weight percent of polymorph Form 7.

In one embodiment, however, one or more of the steps of the method to prepare polymorph Form 3 from Form 7 may be omitted or the order of the steps may be varied. For instance, in alternative embodiments, the methods of making Form 3 do not require adding seeds of Form 3 to Form 7. In some embodiments, the method comprises the steps of heating and cooling the mixture. In some embodiments, polymorph Form 7 is not isolated from the reaction mixture but generated in situ and converted to Form 3.

In some embodiments, Form 3, including seeds thereof, is obtained through alternative methods, for instance, the method described in Example 11. In some embodiments, the method of preparing Form 3 does not comprise adding seeds of Form 3.

In some embodiments, a production scale amount of polymorph Form 3 is greater than 1 kg, 5 kg, 10 kg, 20 kg, 50 kg, 100 kg, 200 kg, or 500 kg. In some embodiments, a production scale amount of polymorph Form 3 is between 1 kg and 500 kg. In some embodiments, a production scale amount of polymorph Form 3 is between 10 kg and 300 kg. In some embodiments, a production scale amount of polymorph Form 3 is between 50 kg and 500 kg.

In some embodiments, the mixture is heated to reflux. In some embodiments, the mixture is heated to a temperature between about 40° C. and about 65° C. In some embodiments, the mixture is heated to a temperature between about 45° C. and about 65° C. In some embodiments, the mixture is heated to a temperature of about 55° C.

In some embodiments, the mixture may be agitated. In some embodiments, the mixture is agitated to facilitate the formation of the Form 3 product. In some embodiments, agitation increases dispersion of the components in a mixture. Well-dispersed components in a mixture prevent high concentrations of certain materials accumulating in a portion of the reaction mixture. For instance, without agitation, adding a solvent to a solution in order to precipitate a solid material, higher concentration of acetone may accumulate in a portion of the solution causing precipitation of solids in an uneven manner. A gummy form of the solid or a solid with other undesirable character may result. Agitation of the solution while adding the solvent, however, can help prevent uneven distribution of the added solvent and prevent undesirable forms of precipitated solid. Agitation speed can be described in terms of revolutions per minute (RPM). In some embodiments, agitation is greater than about 200 RPM, about 150 RPM, about 100 RPM, or about 50 RPM. In some embodiments, agitation is between about 150 to about 250 RPM, about 100 to 200 RPM, 50 to 150 RPM. Agitation is particularly important in heterogeneous mixtures (e.g., slurry). The agitation speed may vary depending on the scale of the reaction volume with smaller reaction volumes having higher RPM than larger reaction volumes. For instance, maximum agitation speed in a production plant may reach about 100 to about 150 RPM. Maximum agitation speed in the laboratory setting may reach over about 200 RPM. In some methods agitation is between about 30 to about 60 RPM.

In some embodiments of the methods, a mixture is formed. In some embodiments, the mixture is a homogeneous solution. In other embodiments, the mixture is heterogeneous, wherein the mixture comprises more than one phase, for instance a solid phase and a liquid phase. In some embodiments the mixture is a slurry. In some embodiments, a portion of the contents of a mixture may undergo phase change over time. For instance, a homogenous solution mixture may form solids over time and become a heterogeneous mixture, wherein the mixture comprises a solid and liquid phase. Alternatively, a heterogeneous mixture may become a homogenous solution mixture, for instance when a solid material dissolves into a solvent. In some embodiments the phase change occurs upon a reaction event. For instance, a homogenous solution mixture may, upon a reaction event, may become a heterogeneous mixture, and vice versa. The reaction event may be a change in the conditions of the reaction mixture, for instance, cooling or heating, addition of a particular solvent, addition of a solid, or evaporation.

In some embodiments, provided is a method of producing polymorph Form 3, which is a polymorph of a monohydrate, bis-mesylate salt of a compound of Formula I, comprising:
adding a compound of Formula I to methanesulfonic acid to produce a bis-mesylate salt of the compound of Formula I; and
adding polymorph Form 3 seeds to the bis-mesylate salt to convert the bis-mesylate salt into polymorph Form 3.
In certain embodiments, the method further comprises isolating the polymorph Form 3 produced.

In other embodiments, provided is a method of preparing polymorph Form 3 by adding the free base of a compound of Formula I to methanesulfonic acid to form the bis-mesylate salt. The bis-mesylate salt is added to an amount of polymorph Form 3 seeds to convert the bis-mesylate salt to Form 3.

In certain embodiments of the methods described above, the bis-mesylate salt is polymorph Form 7, which is isolated, then further used to make Form 3. In other embodiments, the his-mesylate salt is Form 7, and is not isolated from the reaction mixture. The amount of Form 3 seeds is substantially smaller than the amount of free base used in the method to obtain Form 3, and is also substantially smaller than the amount of Form 3 obtained by the methods described herein. In some embodiments, the amount of Form 3 seed added to the bis-mesylate salt is between 0.01 molar % and 5 molar %; between 0.01 molar % and 3 molar %; between 0.01 molar % and 2 molar %; between 0.01 molar % and 1 molar %; between 0.1 molar % and 2 molar %; or between 0.1 molar % and 1 molar %; about 1 molar % of the free base.

In some embodiments, the amount of Form 3 seeds added to the bis-mesylate salt is between 0.001 and 0.1 weight percent; between 0.01 and 0.1 weight percent; or between 0.01 and 0.08 weight percent; or about 0.015 weight percent of the free base.

In some embodiments, the amount of methanesulfonic acid is between about 2.0 and about 2.5 molar equivalents; between about 2.0 and about 2.4 molar equivalents; between about 2.0 and about 2.2 molar equivalents; between about 2.0 and about 2.1 molar equivalents; between about 2.0 and about 2.05 molar equivalents; or about 2.05 molar equivalents with respect to one molar equivalent of the compound of Formula I.

In practicing any of the methods disclosed herein, in some embodiments, at least one solvent is added to the mixture. Non-limiting examples of solvents include methanol, ethanol, isopropanol, ethyl acetate, isopropyl acetate, acetone, tetrahydrofuran, toluene, methyl-t-butyl ether, acetonitrile, heptanes, hexanes, water, methyl ethyl ketone, dichloromethane, 2-methyl-tetrahydrofuran, and methyl isobutyl ketone. In preferred embodiments, the solvent is acetone. In other embodiments, the solvents are acetone and water. In some embodiments, the at least one solvent is an organic solvent. In some embodiments, the at least one solvent is an organic solvent, further comprising water. Non-limiting examples of organic solvents include methanol, ethanol, isopropanol, ethyl acetate, isopropyl acetate, acetone, tetrahydrofuran, toluene, methyl-t-butyl ether, acetonitrile, heptanes, hexanes, methyl ethyl ketone, dichloromethane, 2-methyl-tetrahydrofuran, and methyl isobutyl ketone. In some embodiments, the at least one solvent further comprises a protic solvent. Non-limiting examples of a protic solvent include water, methanol, ethanol, isopropanol, propanol, and butanol. In some embodiments, the at least one solvent is acetone, further comprising water.

In some embodiments, the at least one solvent is an organic solvent and water. In some embodiments, the concentration of water in the water/organic solvent mixture is from about 1% to about 7.5%; from about 2% to about 5%; from about 4% to about 6%; or is about 5%.

In some embodiments, the at least one solvent is acetone and water, wherein the concentration of water in the acetone/water solvent mixture is about 1% to about 7.0%; about 2% to about 5%; about 4% to about 6%; or about 5%.

In some embodiments the ratio of water to acetone is about 1:15 to about 1:40; about 1:18 to about 1:22; about 1:19; or about 1:38.

In some of the foregoing embodiments, the method comprises heating the mixture. In some embodiments, lower temperatures require less water. For instance, while heating the mixture to 55° C. might require a water concentration of about 5%, heating the mixture to 35° C. might require a water concentration of about 4%.

In some embodiments, provided is a method of producing polymorph Form 3 (which is a polymorph of a monohydrate, bis-mesylate salt of a compound of Formula I), comprising:

adding polymorph Form 3 seeds, acetone and water to polymorph Form 7 (which is a polymorph of a hydrate, bis-mesylate salt of a compound of Formula I) to form a mixture; and producing polymorph Form 3 in the mixture.

In certain embodiments, the method further comprises isolating the polymorph Form 3 produced from the mixture.

In some embodiments, provided is a method of preparing a production scale amount of polymorph Form 3, which is a polymorph of a monohydrate, bis-mesylate salt of a compound of Formula I, such as a monohydrate of a compound of Formula IA

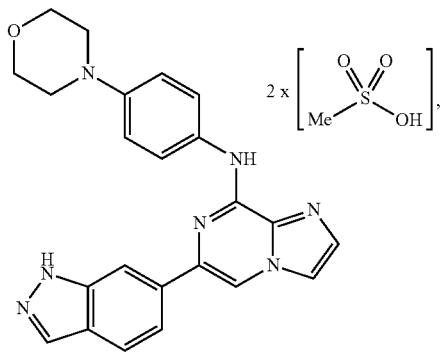

(IA)

comprising adding an amount of polymorph Form 3 seeds, acetone and water to polymorph Form 7 to form a mixture; and isolating polymorph Form 3 produced, wherein the ratio of water to acetone is about 1:18 to about 1:22; optionally further comprising agitating the mixture, and optionally further comprising heating and cooling the mixture before isolating polymorph Form 3 produced. In some embodiments, the mixture is heated to reflux and agitated. In some embodiments, heating the mixture results in a faster conversion of Form 7 to Form 3 compared to not heating the mixture. In some embodiments, isolating polymorph Form 3 comprises filtering the mixture to obtain solids. In some embodiments, the solids are rinsed with a solvent and then dried.

In some embodiments, provided is a method of preparing a production scale amount of polymorph Form 3, which is a polymorph of a monohydrate, bis-mesylate salt of a compound of Formula I, such as a monohydrate of a compound of Formula IA:

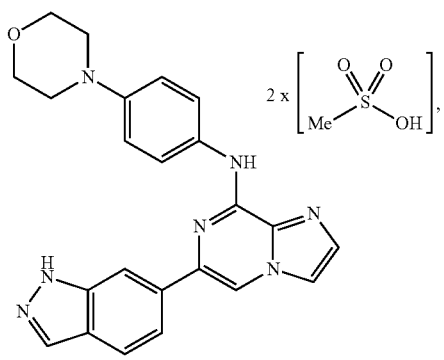

(IA)

comprising adding an amount of polymorph Form 3 seeds and at least one solvent to polymorph Form 7 to form a mixture; and isolating polymorph Form 3 produced, wherein polymorph Form 3 has an X-ray diffraction (XRPD) pattern comprising at least two or more of the 2θ-reflections (±0.2 degrees): 13.8, 16.9, 22.9, and 26.1; and polymorph Form 7 has an X-ray diffraction (XRPD) pattern comprising at least two or more 2θ-reflections (±0.2 degrees): 4.9, 9.8, and 26.7.

In some embodiments, provided is a method of preparing a production scale amount of polymorph Form 3, which is a polymorph of a monohydrate, bis-mesylate salt of a compound of Formula I:

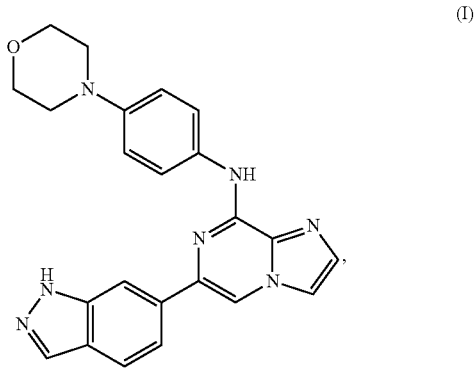 [SMILES: c1cn2cc(-c3ccc4cn[nH]c4c3)nc(Nc3ccc(N4CCOCC4)cc3)c2n1]

(I)

comprising adding acetone and water to the compound of Formula I to form a mixture, adding an amount of methanesulfonic acid to the mixture, heating the mixture, adding an amount of polymorph Form 3 seeds to the mixture; cooling the mixture; and recovering the compound of Formula I as polymorph Form 3, wherein the amount of methanesulfonic acid is about 2.05 molar equivalents with respect to one molar equivalent of the compound of Formula I. In certain embodiments, the compound of Formula I, acetone, and water mixture are under agitation, and methanesulfonic acid is added to the agitated mixture. In some embodiments, the mixture is heated to reflux and agitated.

Methods of Preparing Polymorph Form 7

In some embodiments, provided is a method of producing polymorph Form 7, which is a polymorph of a hydrate, bis-mesylate salt of a compound of Formula I, comprising:

adding a solvent to a compound of Formula I to form a mixture;

adding an amount of methanesulfonic acid to the mixture;

heating the mixture; and cooling the heated mixture to produce polymorph Form 7.

In some embodiments, the method further comprises isolating polymorph Form 7 produced.

In some variations, the solvent comprises methanol, ethanol, isopropanol, ethyl acetate, isopropyl acetate, acetone, tetrahydrofuran, toluene, methyl-t-butyl ether, acetonitrile, heptanes, hexanes, water, methyl ethyl ketone, dichloromethane, 2-methyl-tetrahydrofuran, and methyl isobutyl ketone. In one variation, the solvent comprises acetone. In other embodiments, the solvent comprises acetone and water. In some embodiments, the solvent is an organic solvent. In some embodiments, the solvent is an organic solvent, further comprising water. Non-limiting examples of organic solvents include methanol, ethanol, isopropanol, ethyl acetate, isopropyl acetate, acetone, tetrahydrofuran, toluene, methyl-t-butyl ether, acetonitrile, heptanes, hexanes, methyl ethyl ketone, dichloromethane, 2-methyl-tetrahydrofuran, and methyl isobutyl ketone. In some embodiments, the solvent further comprises a protic solvent.

Non-limiting examples of a protic solvent include water, methanol, ethanol, isopropanol, propanol, and butanol. In some embodiments, the at least one solvent is acetone, further comprising water.

In some embodiments, the mixture is heated to reflux. In some embodiments, the mixture is heated to a temperature between about 40° C. and about 65° C. In some embodiments, the mixture is heated to a temperature between about 45° C. and about 65° C. In some embodiments, the mixture is heated to a temperature of about 55° C.

In some embodiments, the heated mixture is cooled to room temperature. In some embodiments, the heated mixture is cooled to a temperature between about 0° C. and about 30° C., or between about 10° C. and about 30° C., or between about 10° C. and about 25° C., or between about 5° C. and about 30° C., or between about 10° C. and about 30° C., or about 10° C. and about 20° C.

Deuterated Compounds

Any formula or structure given herein, including a compound of Formula I and pharmaceutically acceptable salts thereof (including, for example, the mono-mesylate and the bis-mesylate salts), or a hydrate thereof, is also contemplated as an isotopically labeled form of the compounds, or salts, or hydrates thereof. Thus, although the unlabeled forms of compounds are provided, it is understood that the present disclosure also contemplates isotopically labeled compounds, even though such isotopes are not explicitly depicted. Isotopically labeled compounds, or salts, or hydrates thereof have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^{2}$H (deuterium, D), $^{3}$H (tritium), $^{11}$C, $^{13}$C, $^{14}$C, $^{15}$N, $^{18}$F, $^{31}$P, $^{32}$P, $^{35}$S, $^{36}$Cl and $^{125}$I. For instance, isotopes of hydrogen, carbon, nitrogen, oxygen, phosphorus, fluorine and chlorine, such as, but not limited to $^{2}$H (deuterium, D), $^{3}$H (tritium), $^{11}$C, $^{13}$C, $^{14}$C, $^{15}$N, and $^{35}$S may be incorporated into a compound of formula I, including a salt (e.g. a mesylate salt) of a compound of formula I, or a hydrate thereof. Various isotopically labeled compounds, or salts, or hydrates thereof of the present disclosure, for example those into which radioactive isotopes such as $^{3}$H, $^{13}$C and $^{14}$C are incorporated. Such isotopically labeled compounds or salts thereof may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects.

The disclosure also includes a compound of Formula I and pharmaceutically acceptable salts thereof (including, for example, the mono-mesylate and the bis-mesylate salts), or a hydrate thereof, in which from 1 to n hydrogens attached to a carbon atom is/are replaced by deuterium, in which n is the number of hydrogens in the molecule. Such compounds may exhibit increased resistance to metabolism and are thus useful for increasing the half life of a compound of Formula I, or pharmaceutically acceptable salts thereof, or hydrates thereof (including a bis-mesylate salt of Formula IA or IB, or a hydrate thereof; or a hydrate, bis-mesylate of Formula IC or ID) when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure (including salts or hydrates thereof) may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I and pharmaceutically acceptable salts thereof (including, for example, the mono-mesylate and the bis-mesylate salts), or hydrates thereof.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or salts thereof of this disclosure any atom specifically designated as a deuterium (D) is meant to represent deuterium.

Pharmaceutical Compositions

The mesylate salts described herein (including the mono-mesylate and bis-mesylate salts of a compound of Formula I, or a hydrate thereof), and any polymorphic forms thereof described herein (e.g., Form 3 and/or Form 7), can be administered as the neat chemical, but it is typical, and preferable, to administer the compound, or salt or hydrate thereof, in the form of a pharmaceutical composition or formulation. Provided are pharmaceutical compositions comprising: (i) a bis-mesylate salt of a compound of Formula I, or a hydrate thereof, or polymorph of the foregoing, and (ii) a pharmaceutical carrier, excipient, adjuvant, or vehicle. Pharmaceutical carrier, excipient, adjuvant, or vehicle may also be referred to herein as pharmaceutically acceptable carrier excipient, adjuvant or vehicle or as biocompatible pharmaceutical carrier, excipient, adjuvant, or vehicle. Accordingly, provided are pharmaceutical compositions that comprise polymorph Form 3 and/or Form 7 and a biocompatible pharmaceutical carrier, excipient, adjuvant, or vehicle. The composition can include the bis-mesylate salt of a compound of Formula I, or a hydrate thereof, or polymorphic forms described herein either as the sole active agent or in combination with other agents, such as oligo- or polynucleotides, oligo- or polypeptides, drugs, or hormones mixed with one or more pharmaceutically acceptable carriers or excipients. Carriers, excipients, and other ingredients can be deemed pharmaceutically acceptable insofar as they are compatible with other ingredients of the formulation and not deleterious to the recipient thereof.

In one aspect, provided is a pharmaceutical composition, comprising: a bis-mesylate salt of a compound of Formula I, or a hydrate thereof; and a pharmaceutical carrier, excipient, adjuvant, or vehicle. In certain aspects, provided is a pharmaceutical composition, comprising: a hydrate, bis-mesylate salt of a compound of Formula I, and a pharmaceutical carrier, excipient, adjuvant, or vehicle. In one aspect, provided is a pharmaceutical composition, comprising: a monohydrate, bis-mesylate salt of a compound of Formula I, and a pharmaceutical carrier, excipient, adjuvant, or vehicle. In certain aspects, provided is a pharmaceutical composition, comprising: a mesylate salt of Formula IA or IB, or a hydrate thereof; and a pharmaceutical carrier, excipient, adjuvant, or vehicle. In other aspects, provided is a pharmaceutical composition, comprising: a hydrate, mesylate salt of Formula IA or IB; and a pharmaceutical carrier, excipient, adjuvant, or vehicle.

For example, in some embodiments, provided herein is a pharmaceutical composition comprising polymorph Form 3, and a pharmaceutical acceptable carrier or other excipient. In one embodiment of the pharmaceutical composition, the polymorph Form 3 in the composition is present in excess of other polymorphic forms. For example, the weight ratio of polymorph Form 3 to other polymorph forms in the pharmaceutical composition may be between 85 to 15, 90 to 10, 95 to 5, or 99 to 1. In one embodiment, the weight ratio of polymorph Form 3 to other polymorph forms is between 90:1 and 99:1.

The term "carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E. W. Martin.

The pharmaceutical compositions can be formulated to contain suitable pharmaceutically acceptable carriers, and optionally can comprise excipients and auxiliaries that facilitate processing of the polymorphic forms described herein into preparations that can be used pharmaceutically. The mode of administration generally determines the nature of the carrier. For example, formulations for parenteral administration can include aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hanks's solution, Ringer's solution, or physiologically buffered saline. For tissue or cellular administration, penetrants appropriate to the particular barrier to be permeated are used in the formulation. Such penetrants are generally known in the art. For preparations including proteins, the formulation can include stabilizing materials, such as polyols (e.g., sucrose) and/or surfactants (e.g., nonionic surfactants), and the like.

Alternatively, formulations for parenteral use can include dispersions or suspensions of polymorphic forms described herein prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, dextran, and mixtures thereof. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT™ series available from Rohm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the polymorphic forms described herein also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines lecithins), both natural and synthetic. Methods of forming liposomes are known in the art. See, e.g., Prescott (Ed.), Methods in Cell Biology, Vol. XIV, p. 33, Academic Press, New York (1976).

In some embodiments, the polymorph, or composition thereof, disclosed herein is formulated for oral administration using pharmaceutically acceptable carriers well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or more excipients, which include, without limitation: a) diluents, such as microcrystalline cellulose and sugars, including lactose, dextrose, sucrose, mannitol, or sorbitol; b) binders, such as sodium starch glycolate, croscarmellose sodium, magnesium aluminum silicate, starch from corn, wheat, rice, potato, etc.; c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen; d) disintegrating or solubilizing agents such as cross-linked polyvinyl pyrrolidone, starches, agar, alginic acid or a salt thereof, such as sodium alginate, or effervescent compositions; e) lubricants, such as silica, talc, stearic acid or its magnesium or calcium salt, and polyethylene glycol; f) flavorants and sweeteners; g) colorants or pigments, e.g., to identify the product or to characterize the quantity (dosage) of active compound; and h) other ingredients, such as preservatives, stabilizers, swelling agents, emulsifying agents, solution promoters, salts for regulating osmotic pressure, and buffers.

Examples of preferred carriers include, but are not limited to, aluminum monostearate, aluminum stearate, carboxymethylcellulose, carboxymethylcellulose sodium, crospovidone, glyceryl isostearate, glyceryl monostearate, hydroxyethylcellulose, hydroxymethylcellulose, hydroxyoctacosanyl hydroxystearate, hydroxypropylcellulose, hydroxypropylmethylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions provided in the present disclosure, and the amounts of such carriers in the composition, may vary depending on the method of formulation (e.g., dry granulation formulation, solid dispersion formulation).

In certain variations, the pharmaceutical composition comprises Form 3, and at least one pharmaceutically acceptable carrier selected from the group consisting of hydroxypropylmethylcellulose, mannitol, crospovidone, poloxamer, colloidal silicon dioxide, microcrystalline cellulose, magnesium stearate, and any mixtures thereof. In another variation, the pharmaceutical composition comprises polymorph Form 3, hydroxypropylmethylcellulose, and at least one additionally pharmaceutically acceptable carrier selected from the group consisting of mannitol, crospovidone, poloxamer, colloidal silicon dioxide, microcrystalline cellulose, magnesium stearate, and any mixtures thereof.

It should also be understood that the pharmaceutically acceptable carriers described above may perform one or more different functions in a given formulation, and may fall within one or more functional classes of carriers (e.g., disintegrants, lubricants, diluents).

It should further be understood that, in other embodiments, the pharmaceutical composition may comprise one or more additional carriers to improve flow, compression, hardness, taste, and tablet performance.

In some embodiments, the pharmaceutical composition comprises a) about 34% w/w of a mesylate salt (including, for example, a mono-mesylate or bis-mesylate salt) of a compound of Formula I; b) about 15% w/w HPMC; c) about 22% w/w mannitol; d) about 10% w/w crospovidone; and e) about 1% w/w to about 3% w/w poloxamer. In one variation, the pharmaceutical composition comprises: a) about 34% w/w of a bis-mesylate salt of a compound of Formula I, or a hydrate thereof; b) about 15% w/w HIPMC; c) about 22% w/w mannitol; d) about 10% w/w crospovi done; and e) about 1% w/w to about 3% w/w poloxamer. In another variation, the pharmaceutical composition comprises: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another variation, the pharmaceutical composition comprises: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

Methods of Use

Provided is also the use of the pharmaceutical compositions described in the present disclosure to selectively or specifically inhibit Syk activity therapeutically or prophylactically. The method comprises administering the pharmaceutical composition to an individual in need thereof in an amount sufficient to inhibit Syk activity. The method can be employed to treat subjects (e.g., humans) suffering from, or subject to, a condition whose symptoms or pathology is mediated by Syk expression or activity.

In one aspect, provided is a method of treating a human in need thereof, comprising administering a bis-mesylate salt of a compound of Formula I, or a hydrate thereof, to the human. In certain aspects, provided is a method of treating a human in need thereof, comprising administering a hydrate, bis-mesylate salt of a compound of Formula I to the human. In one aspect, provided is a method of treating a human in need thereof, comprising administering a monohydrate, bis-mesylate salt of a compound of Formula I to the human. In certain aspects, provided is a method of treating a human in need thereof, comprising administering a mesylate salt of Formula IA or IB, or a hydrate thereof, to the human. In other aspects, provided is a method of treating a human in need thereof, comprising administering a hydrate, mesylate salt of Formula IA or IB to the human. In one aspect, provided is a method of treating a human in need thereof, comprising administering polymorph Form 3 to the human. In one aspect, provided is a method of treating a human in need thereof, comprising administering polymorph Form 7 to the human.

"Treatment" or "treating" is an approach for obtaining beneficial or desired results including clinical results. Beneficial or desired clinical results may include one or more of the following:

a) inhibiting the disease or condition (e.g., decreasing one or more symptoms resulting from the disease or condition, and/or diminishing the extent of the disease or condition);

b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" of the pharmaceutical composition means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Syk activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Syk activity" refers to a decrease in activity of Syk as a direct or indirect response to the presence of the pharmaceutical composition, relative to the activity of Syk in the absence of such pharmaceutical composition. In some embodiments, the inhibition of Syk activity may be compared in the same subject prior to treatment, or other subjects not receiving the treatment.

In certain aspects, a bis-mesylate salt of a compound of Formula I (including polymorphs of such bis-mesylate salt, such as Form 3 and/or Form 7), or a hydrate thereof, and compositions thereof described herein are used for treating a subject having cancer, an allergic disorder and/or an autoimmune and/or inflammatory disease, and/or an acute inflammatory reaction.

In one aspect, the pharmaceutical compositions provided in the present disclosure may be used in the treatment of cancer. In some embodiments, the polymorphs and compositions thereof described herein can be employed in methods of inhibiting the growth or proliferation of cancer cells of hematopoietic origin, such as cancer cells. In some embodiments, the cancer cells are of lymphoid origin, and in specific embodiments, the cancer cells are related to or derived from B lymphocytes or B lymphocyte progenitors.

Cancers amenable to treatment using the method disclosed in the present disclosure include, without limitation, lymphomas (e.g., malignant neoplasms of lymphoid and reticuloendothelial tissues, such as Burkitt's lymphoma, Hodgkins' lymphoma, non-Hodgkins' lymphomas, lymphocytic lymphomas); multiple myelomas; leukemias (e.g., lymphocytic leukemias, chronic myeloid (myelogenous) leukemias). Other cancer cells, of hematopoietic origin or otherwise, that express spleen tyrosine kinase (Syk) also can be treated by administration of the polymorphs and compositions thereof described herein.

In particular embodiments of the methods provided herein, the cancer is leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain variations, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In yet another embodiment, the cancer is non-FL iNHL.

In particular embodiments of the methods provided herein, the cancer is a hematologic malignancy. In certain embodiments, the hematologic malignancy is leukemia (e.g., chronic lymphocytic leukemia) or lymphoma (e.g., non-Hodgkin's lymphoma). In some variations, the cancer is MCL, DLBCL, iNHL, FL, MZL, LPL, SLL, or WM. In other variations, the cancer is CLL, MCL, DLBCL, iNHL (including, for example, non-FL iNHL), or FL.

In other embodiments, the cancer is a solid tumor cancer (or solid cancer tumor). In certain embodiments the cancer is a solid tumor and expresses spleen tyrosine kinase (Syk) activity. In other embodiments, the solid tumor cancer is selected from the group consisting of pancreatic cancer, lung cancer, colon cancer, colo-rectal cancer, breast cancer, esophageal cancer, adenocarcinoma, hepatocellular cancer. In one embodiment, the solid tumor cancer is selected from the group consisting of pancreatic cancer, lung cancer, colorectal cancer, ovarian cancer, and hepatocellular cancer.

Any of the methods of treatment provided herein may be used to treat cancer at an advanced stage. Any of the methods of treatment provided herein may be used to treat cancer at locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

In some embodiments, the conditions and diseases that can be affected using the compounds and the compositions described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, ulcerative colitis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic obstructive pulmonary disease (COPD), adult respiratory distress syndrome (ARDS), chronic Idiopathic thrombocytopenic purpura (ITP), Addison's disease, Parkinson's disease, Alzheimer's disease, diabetes, septic shock, and myasthenia gravis; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis gastritis, enteritis, dermatitis, gingivitis, appendicitis, pancreatitis, and cholocystitis; polycystic kidney disease.

In some embodiments, provided are also the use of the compounds and compositions described herein in the treatment of an autoimmune disease. Certain embodiments of an autoimmune disease include asthma, rheumatoid arthritis, multiple sclerosis, and lupus.

In yet another aspect, provided are methods of treating an individual having a Syk-mediated disorder by administering any of the pharmaceutical compositions provided in the present disclosure to the individual. Provided are also methods of modulating Syk in an individual by administering any of the pharmaceutical compositions provided in the present disclosure to the individual.

In some of the foregoing methods, the pharmaceutical compositions provided in the present disclosure may be administered to the individual as unit dosage, for example in the form of a tablet. In some variations, a mesylate salt (including, for example, a mono-mesylate or bis-mesylate salt), or a hydrate thereof, is administered in the form a tablet. In another variation, polymorph Form 3, which is a polymorph of a monohydrate, bis-mesylate salt of a compound of Formula I (e.g., polymorph of a monohydrate of the bis-mesylate salt of Formula IA) is used in the spray dry preparation of the unit dosage, wherein the final unit dosage does not substantially contain the polymorph Form 3.

Subjects

Any of the methods of treatment provided may be used to treat a subject who has been diagnosed with or is suspected of having a cancer, an allergic disorder and/or an autoimmune and/or inflammatory disease, and/or an acute inflammatory reaction.

In some of the embodiments of any of the methods provided herein, the subject is a human who is at risk of developing a cancer (e.g., a human who is genetically or otherwise predisposed to developing a cancer) and who has or has not been diagnosed with the cancer. As used herein, an "at risk" subject is a subject who is at risk of developing cancer (e.g., a hematologic malignancy). The subject may or may not have detectable disease, and may or may not have displayed detectable disease prior to the treatment methods described herein. An at risk subject may have one or more so-called risk factors, which are measurable parameters that correlate with development of cancer, such as described herein. A subject having one or more of these risk factors has a higher probability of developing cancer than an individual without these risk factor(s).

These risk factors may include, for example, age, sex, race, diet, history of previous disease, presence of precursor disease, genetic (e.g., hereditary) considerations, and environmental exposure. In some embodiments, a subject at risk for cancer includes, for example, a subject whose relatives have experienced this disease, and those whose risk is determined by analysis of genetic or biochemical markers. Prior history of having cancer may also be a risk factor for instances of cancer recurrence.

Provided herein are also methods for treating a subject (e.g., a human) who exhibits one or more symptoms associated with cancer (e.g., a hematologic malignancy). In some embodiments, the subject is at an early stage of cancer. In other embodiments, the subject is at an advanced stage of cancer.

In some embodiments, the subject (e.g., a human) has a cancer responsive to Syk activity. In another embodiment, the human has a solid cancer tumor which expresses Syk. In some embodiments, the human has a 17p deletion, a TP53 mutation, NOTCH1, a SF3B1 mutation, a 11q deletion, or any combination thereof. In one embodiment, the human has a 17p deletion, a TP53 mutation, or a combination thereof. In another embodiment, the human has NOTCH1, a SF3B1 mutation, a 11q deletion, or any combination thereof.

Provided herein are also methods for treating a subject (e.g., a human) who is undergoing one or more standard therapies for treating cancer (e.g., a hematologic malignancy), such as chemotherapy, radiotherapy, immunotherapy, and/or surgery. Thus, in some foregoing embodiments, a bis-mesylate salt of a compound of Formula I (including polymorphs of such bis-mesylate salt, such as Form 3 and/or Form 7), or a hydrate thereof, and compositions described herein is administered before, during, or after administration of chemotherapy, radiotherapy, immunotherapy, and/or surgery.

In another aspect, provided herein are methods for treating a subject (e.g., a human) who is "refractory" to a cancer treatment or who is in "relapse" after treatment for cancer (e.g., a hematologic malignancy). A subject "refractory" to an anti-cancer therapy means they do not respond to the particular treatment, also referred to as resistant. The cancer may be resistant to treatment from the beginning of treatment, or may become resistant during the course of treatment, for example after the treatment has shown some effect on the cancer, but not enough to be considered a remission or partial remission. A subject in "relapse" means that the cancer has returned or the signs and symptoms of cancer have returned after a period of improvement, e.g. after a treatment has shown effective reduction in the cancer, such as after a subject is in remission or partial remission.

In some embodiments, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies).

In certain embodiments, the subject is a human who is (i) refractory to, and/or (ii) in relapse after treatment with at least one therapy for chronic lymphocytic leukemia (CLL), mantle cell lymphoma (MCL), diffuse large B-cell lymphoma (DLBCL), follicular lymphoma (FL), or non-FL indolent non-Hodgkin's lymphoma (including, for example, lymphoplasmacytic lymphoma/Waldestrom's macroglobulinemia (LPL/WM), small lymphocytic lymphoma (SLL), and marginal zone lymphoma (MZL)).

In some variations, the subject is a human who (i) is refractory to, and/or (ii) is in relapse after treatment with, and/or (iii) has prior exposure to at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the subject is a human who (i) is refractory to, and/or (ii) is in relapse after treatment with, and/or (iii) has prior exposure to at least one therapy for follicular lymphoma (FL). In another variation, the subject is a human who (i) is refractory to, and/or (ii) is in relapse after treatment with, and/or (iii) has prior exposure to at least one therapy for diffuse large B-cell lymphoma (DLBCL). In another variation, the subject is a human who (i) is refractory to, and/or (ii) is in relapse after treatment with, and/or (iii) has prior exposure to at least one therapy for mantle cell lymphoma (MCL). In yet another variation, the subject is a human who (i) is refractory to, and/or (ii) is in relapse after treatment with, and/or (iii) has prior exposure to at least one therapy for chronic lymphocytic leukemia (CLL). In yet another variation, the subject is a human who (i) is refractory to, and/or (ii) is in relapse after treatment with, and/or (iii) has prior exposure to a phosphatidylinositol 3-kinase (PI3K) inhibitor, a bruton tyrosine kinase (BTK) inhibitor, or a B-cell receptor (BCR) treatment for chronic lymphocytic leukemia (CLL).

In some embodiments, the subject is refractory to at least one, at least two, at least three, or at least four anti-cancer therapy (including, for example, standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD), FCM (fludarabine, cyclophosphamide, mitoxantrone); R-FCM (rituximab, fludarabine, cyclophosphamide, mitoxantrone); bortezomib and rituximab, temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

For example, treatment of non-Hodgkin's lymphomas (NHL), especially of B-cell origin, include the use of monoclonal antibodies, standard chemotherapy approaches (e.g., CHOP, CVP, FCM, MCP, and the like), radioimmunotherapy, and combinations thereof, especially integration of an antibody therapy with chemotherapy. Examples of unconjugated monoclonal antibodies for Non-Hodgkin's lymphoma/B-cell cancers include rituximab, alemtuzumab, human or humanized anti-CD20 antibodies, lumiliximab, anti-TRAIL, bevacizumab, galiximab, epratuzumab, SGN-40, and anti-CD74. Examples of experimental antibody agents used in treatment of Non-Hodgkin's lymphoma/B-cell cancers include ofatumumab, ha20, PRO131921, alemtuzumab, galiximab, SGN-40, CHIR-12.12, epratuzumab, lumiliximab, apolizumab, milatuzumab, and bevacizumab. Examples of standard regimens of chemotherapy for Non-Hodgkin's lymphoma/B-cell cancers include CHOP (cyclophosphamide, doxorubicin, vincristine, prednisone), FCM (fludarabine, cyclophosphamide, mitoxantrone), CVP (cyclophosphamide, vincristine and prednisone), MCP (mitoxantrone, chlorambucil, and prednisolone), R-CHOP (rituximab plus CHOP), R-FCM (rituximab plus FCM), R-CVP (rituximab plus CVP), and R-MCP (R-MCP). Examples of radioimmunotherapy for Non-Hodgkin's lymphoma/B-cell cancers include yttrium-90-labeled ibritumomab tiuxetan, and iodine-131-labeled tositumomab.

In another example, therapeutic treatments for mantle cell lymphoma (MCL) include combination chemotherapies such as CHOP (cyclophosphamide, doxorubicin, vincristine, prednisone), hyperCVAD (hyperfractionated cyclophosphamide, vincristine, doxorubicin, dexamethasone, methotrexate, cytarabine) and FCM (fludarabine, cyclophosphamide, mitoxantrone). In addition, these regimens can be supplemented with the monoclonal antibody rituximab (Rituxan) to form combination therapies R-CHOP, hyperCVAD-R, and R-FCM. Other approaches include combining any of the abovementioned therapies with stem cell transplantation or treatment with ICE (iphosphamide, carboplatin and etoposide). Other approaches to treating mantle cell lymphoma includes immunotherapy such as using monoclonal antibodies like Rituximab (Rituxan). Rituximab can be used for treating indolent B-cell cancers, including marginal-zone lymphoma, WM, CLL and small lymphocytic lymphoma. A modified approach is radioimmunotherapy, wherein a monoclonal antibody is combined with a radioisotope particle, such as Iodine-131 tositumomab (Bexxar®) and Yttrium-90 ibritumomab tiuxetan (Zevalin®). In another example, Bexxar® is used in sequential treatment with CHOP.

Another immunotherapy example includes using cancer vaccines, which is based upon the genetic makeup of an individual subject's tumor. A lymphoma vaccine example is GTOP-99 (MyVax®). Yet other approaches to treating mantle cell lymphoma includes autologous stem cell transplantation coupled with high-dose chemotherapy, or treating mantle cell lymphoma includes administering proteasome inhibitors, such as Velcade® (bortezomib or PS-341), or antiangiogenesis agents, such as thalidomide, especially in combination with Rituxan. Another treatment approach is administering drugs that lead to the degradation of Bcl-2 protein and increase cancer cell sensitivity to chemotherapy, such as oblimersen (Genasense) in combination with other chemotherapeutic agents. Another treatment approach includes administering mTOR inhibitors, which can lead to inhibition of cell growth and even cell death; a non-limiting example is Temsirolimus (CCI-779), and Temsirolimus in combination with Rituxan®, Velcade® or other chemotherapeutic agents.

Other recent therapies for MCL have been disclosed (*Nature Reviews*; Jares, P. 2007). Such examples include Flavopiridol, PD0332991, R-roscovitine (Selicilib, CYC202), Styryl sulphones, Obatoclax (GX15-070), TRAIL, Anti-TRAIL DR4 and DR5 antibodies, Temsirolimus (CCI-779), Everolimus (RAD001), BMS-345541, Curcumin, Vorinostat (SAHA), Thalidomide, lenalidomide (Revlimid®, CC-5013), and Geldanamycin (17-AAG).

Examples of other therapeutic agents used to treat Waldenstrom's Macroglobulinemia (WM) include perifosine, bortezomib (Velcade®), rituximab, sildenafil citrate (Viagra®), CC-5103, thalidomide, epratuzumab (hLL2-anti-CD22 humanized antibody), simvastatin, enzastaurin, campath-1H, dexamethasone, DT PACE, oblimersen, antineoplaston A10, antineoplaston AS2-1, alemtuzumab, beta alethine, cyclophosphamide, doxorubicin hydrochloride, prednisone, vincristine sulfate, fludarabine, filgrastim, melphalan, recombinant interferon alfa, carmustine, cisplatin, cyclophosphamide, cytarabine, etoposide, melphalan, dolastatin 10, indium In 111 monoclonal antibody MN-14, yttrium Y 90 humanized epratuzumab, anti-thymocyte globulin, busulfan, cyclosporine, methotrexate, mycophenolate mofetil, therapeutic allogeneic lymphocytes, Yttrium Y 90 ibritumomab tiuxetan, sirolimus, tacrolimus, carboplatin, thiotepa, paclitaxel, aldesleukin, recombinant interferon alfa, docetaxel, ifosfamide, mesna, recombinant interleukin-12, recombinant interleukin-11, Bcl-2 family protein inhibitor ABT-263, denileukin diftitox, tanespimycin, everolimus, pegfilgrastim, vorinostat, alvocidib, recombinant flt3 ligand, recombinant human thrombopoietin, lymphokine-activated killer cells, amifostine trihydrate, aminocamptothecin, irinotecan hydrochloride, caspofungin acetate, clofarabine, epoetin alfa, nelarabine, pentostatin, sargramostim, vinorelbine ditartrate, WT-1 analog peptide vaccine, WT1 126-134 peptide vaccine, fenretinide, ixabepilone, oxaliplatin, monoclonal antibody CD19, monoclonal antibody CD20, omega-3 fatty acids, mitoxantrone hydrochloride, octreotide acetate, tositumomab and iodine I-131 tositumomab, motexafin gadolinium, arsenic trioxide, tipifarnib, autologous human tumor-derived HSPPC-96, veltuzumab, bryostatin 1, and PEGylated liposomal doxorubicin hydrochloride, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

Examples of other therapeutic agents used to treat diffuse large B-cell lymphoma (DLBCL) drug therapies (*Blood* 2005 Abramson, J.) include cyclophosphamide, doxorubicin, vincristine, prednisone, anti-CD20 monoclonal antibodies, etoposide, bleomycin, many of the agents listed for Waldenstrom's, and any combination thereof, such as ICE and R-ICE.

Examples of other therapeutic agents used to treat chronic lymphocytic leukemia (CLL) (Spectrum, 2006, Fernandes, D.) include Chlorambucil (Leukeran), Cyclophosphamide (Cyloxan, Endoxan, Endoxana, Cyclostin), Fludarabine (Fludara), Pentstatin (Nipent), Cladribine (Leustarin), Doxorubicin (Adriamycin®, Adriblastine), Vincristine (Oncovin), Prednisone, Prednisolone, Alemtuzumab (Campath, MabCampath), many of the agents listed for Waldenstrom's, and combination chemotherapy and chemoimmunotherapy, including the common combination regimen: CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); and FR (fludarabine, rituximab).

In another aspect, provided is a method of sensitizing a subject (e.g., a human) who is (i) refractory to at least one chemotherapy treatment, or (ii) in relapse after treatment with chemotherapy, or both (i) and (ii), wherein the method comprises administering a bis-mesylate salt of a compound of Formula I (including polymorphs of such bis-mesylate salt, such as Form 3 and/or Form 7), or a hydrate thereof, or a pharmaceutical composition thereof, to the subject. A subject who is sensitized is a subject who is responsive to the treatment involving administration of a bis-mesylate salt of a compound of Formula I (including polymorphs of such bis-mesylate salt, such as Form 3 and/or Form 7), or a hydrate thereof, and compositions thereof described herein, or who has not developed resistance to such treatment.

In another aspect, provided herein are methods for treating a subject (e.g., a human) for a cancer, with comorbidity, wherein the treatment is also effective in treating the comorbidity. A "comorbidity" to cancer is a disease that occurs at the same time as the cancer.

In some embodiments, provided herein are methods for treating a subject (e.g., a human) for chronic lymphocytic leukemia (CLL), with comorbidity, wherein the treatment is also effective in treating the comorbidity. Many subjects with CLL will have one or more other diseases, for example diseases affecting the blood pressure system, vascular and heart systems, endocrine and metabolic systems, genitourinary system, musculoskeletal system, respiratory system, neurological system, upper and lower gastrointestinal systems, psychiatric system, ear, nose and throat systems, renal system, or liver system. Specific morbidities of CLL include, but are not limited to, one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis (Satram-Hoang et al., *Journal of Cancer Therapy*, 2013; 4:1321-1329; Thurmes et al., *Leukemia & Lymphoma*, 2008; 49(1):49-56).

In some embodiments, a method of treating a comorbidity of CLL in a subject (e.g., a human), wherein the method comprises administering a compound of Formula I, or a pharmaceutically acceptable salt thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Monotherapy and Combination Therapies

Provided are methods of treatment in which the pharmaceutical composition provided in the present disclosure is administered to a subject (e.g., a human), such that the mesylate salt (including, for example, a bis-mesylate salt) of a compound of Formula I, or a hydrate thereof, is the only therapeutic agent administered to the subject. Provided are also methods of treatment in which the pharmaceutical composition provided in the present disclosure administered to a subject (e.g., a human) is given to a subject (e.g., a human) in combination with one or more additional therapeutic agents or other therapies. Both monotherapy and combination therapies are intended and described for use in the methods detailed herein, such as in a method of treating any of the diseases or conditions detailed herein and for use with any subject detailed herein.

Monotherapy

In some embodiments, a method of treating cancer, an allergic disorder and/or an autoimmune and/or inflammatory disease, and/or an acute inflammatory reaction comprises administering to a subject in need thereof an effective amount of a bis-mesylate salt of a compound of Formula I (including polymorphs of such bis-mesylate salt, such as Form 3 and/or Form 7), or a hydrate thereof, wherein the subject is not undergoing therapy for the same disease or condition with another agent or procedure.

In some embodiments where the bis-mesylate salt of a compound of Formula I, (including polymorphs of such bis-mesylate salt, such as Form 3 and/or Form 7), or a hydrate thereof, is administered as a monotherapy to the subject who has been diagnosed with or is suspected of having a cancer, the subject may be a human who is (i) refractory to at least one anti-cancer therapy, or (ii) in relapse after treatment with at least one anti-cancer therapy, or both (i) and (ii). In some of embodiments, the subject is refractory to at least two, at least three, or at least four anti-cancer therapy (including, for example, standard or experimental chemotherapies). For example, in some embodiments, the subject may be a human who is (i) refractory to a therapy using an anti-CD20 antibody, an alkylating agent (e.g., bendamustine), a purine analog (e.g., fludarabine), an anthracycline, or any combination thereof, (ii) in relapse after treatment with an anti-CD20 antibody, an alkylating agent (e.g., bendamustine), a purine analog (e.g., fludarabine), an anthracycline, or any combination thereof, or both (i) and (ii).

A human subject who is refractory to at least one anti-cancer therapy and/or is in relapse after treatment with at least one anti-cancer therapy, as described above, may have undergone one or more prior therapies. In some embodiments, such subjects have undergone one, two, three, or four, or at least one, at least two, at least three, at least four, or at least five, or between one and ten, between one and nine, between one and eight, between one and seven, between one and six, between one and five, or between one and four, anti-cancer therapies prior to treatment using the methods described herein (e.g., prior to the administration of the compound of Formula I, or a pharmaceutically acceptable salt thereof, as a monotherapy).

It should be understood that when a subject (e.g. a human) is treated with the compound of Formula I, or a pharmaceutically acceptable salt thereof, as a monotherapy, the subject may also undergo one or more other therapies that are not anti-cancer therapies.

In some embodiments, a method of treating a comorbidity of a cancer, including but not limited to CLL, in a subject (e.g., a human) who has been diagnosed with cancer, e.g. CLL, wherein the method comprises administering a therapy to treat the comorbidity in combination with of a bis-mesylate salt of a compound of Formula I (including polymorphs of such bis-mesylate salt, such as Form 3 and/or Form 7), or a hydrate thereof, or a pharmaceutical composition thereof, to the subject. In some embodiments, the comorbidity is selected from the group consisting of one or more other cancers (e.g. breast, head and neck, lung, melanoma, non-Hodgkin's T-cell lymphoma, prostate, colon, small intestine, gynecologic and urinary tract), hypertension, hyperlipidemia, coronary artery disease, peripheral vascular diseases, cardiomyopathy, vulvular heart disease, atrial fibrillation, cerebrovascular disease (e.g. transient ischemic attack, stroke), chronic obstructive pulmonary disease, joint disease, peptic ulcer, inflammatory bowel disease, psychiatric illness, thyroid disease, benign prostate hyperplasia, diabetes mellitus, and osteoarthritis.

Combination Therapies

In some embodiments, a method of treating cancer, an allergic disorder and/or an autoimmune and/or inflammatory disease, and/or an acute inflammatory reaction comprises administering to a subject (e.g., a human) in need thereof an effective amount of the pharmaceutical composition described herein, together with one or more additional therapies (e.g., one or more additional therapeutic agents), which can be useful for treating a cancer, an allergic disorder and/or an autoimmune and/or inflammatory disease, and/or an acute inflammatory reaction.

In some embodiments, a method of treating cancer, an allergic disorder and/or an autoimmune and/or inflammatory disease, and/or an acute inflammatory reaction comprises administering to a subject in need thereof an effective amount of a bis-mesylate salt of a compound of Formula I (including polymorphs of such bis-mesylate salt, such as Form 3 and/or Form 7), or a hydrate thereof, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a bis-mesylate salt of a compound of Formula I (including polymorphs of such bis-mesylate salt, such as Form 3 and/or Form 7), or a hydrate thereof. In some embodiments, a bis-mesylate salt of a compound of Formula I (including polymorphs of such bis-mesylate salt, such as Form 3 and/or Form 7), or a hydrate thereof, is combined with another active agent in a single dosage form.

Provided herein are also methods of treatment in which a bis-mesylate salt of a compound of Formula I (including polymorphs of such bis-mesylate salt, such as Form 3 and/or Form 7), or a hydrate thereof, is administered to a subject (e.g., a human) who has been diagnosed with or is suspected of having a cancer is given to the subject in combination with one or more additional therapies, including one or more of the anti-cancer therapies described above. Thus, in some embodiments, the method for treating cancer in a subject (e.g., a human) in need thereof, comprises administering to the subject a therapeutically effective amount of a bis-mesylate salt of a compound of Formula I (including polymorphs of such bis-mesylate salt, such as Form 3 and/or Form 7), or a hydrate thereof, or a pharmaceutical composition thereof, together with one or more additional therapies, which can be useful for treating the cancer. The one or more additional therapies may involve the administration of one or more therapeutic agents.

In one aspect, provided is a method of treating cancer in a human in need thereof, comprising administering a bis-mesylate salt of a compound of Formula I (including polymorphs of such bis-mesylate salt, such as Form 3 and/or Form 7), or a hydrate thereof, and an additional therapeutic agent to the human. In certain aspects, provided is a method of treating cancer in a human in need thereof, comprising administering a hydrate, bis-mesylate salt of a compound of Formula I to the human, and an additional therapeutic agent to the human. In one aspect, provided is a method of treating cancer in a human in need thereof, comprising administering a monohydrate, bis-mesylate salt of a compound of Formula I to the human, and an additional therapeutic agent to the human. In certain aspects, provided is a method of treating cancer in a human in need thereof, comprising administering a mesylate salt of Formula IA or IB, or a hydrate thereof to the human, and an additional therapeutic agent to the human. In other aspects, provided is a method of treating cancer in a human in need thereof, comprising administering a hydrate, mesylate salt of Formula IA or IB to the human, and an additional therapeutic agent to the human. In one aspect, provided is a method of treating cancer in a human in need thereof, comprising administering polymorph Form 3 to the human, and an additional therapeutic agent to the human. In another aspect, provided is a method of treating cancer in a human in need thereof, comprising administering polymorph Form 7 to the human, and an additional therapeutic agent to the human. In any of the foregoing embodiments, the treatment of cancer may include, for example, leukemia, lymphoma and solid-cell tumors.

The additional therapeutic agent may be one or more agents. In some embodiments, the one or more additional therapeutic agent may be a phosphatidylinositol 3-kinase (PI3K) inhibitor, including for example, Compounds A, B, C and D, whose structures are provided below.

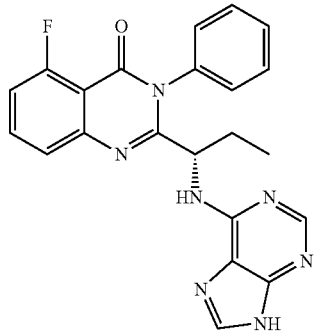

Compound A

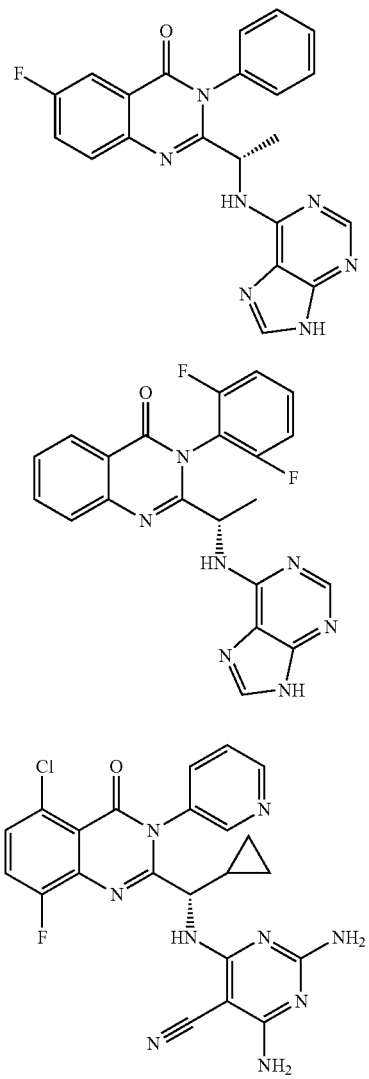

Compound B

Compound C

Compound D

In other embodiments, the one or more additional therapeutic agent may be an inhibitors of lysyl oxidase-like 2 (LOXL2) or a substance that binds to LOXL2, including for example, a humanized monoclonal antibody (mAb) with an immunoglobulin IgG4 isotype directed against human LOXL2. In yet other embodiments, the one or more additional therapeutic agent may be an inhibitor of apoptosis signal-regulating kinase (ASK-1) or a substance that binds to ASK-1. In yet other embodiments, the one or more additional therapeutic agent may be an inhibitor of a Janus kinase, such as JAK1 or JAK2, or a substance that binds to a Janus kinase, such as JAK1 or JAK2. In one embodiment, the one or more additional therapeutic agent is momelotinib. In other embodiments, the one or more additional therapeutic agent may be a Bruton's tyrosine kinase (BTK) inhibitor. In yet other embodiments, the one or more additional therapeutic agent may be a B-cell lymphoma (BCL) inhibitor. In some variations, the BCL inhibitor is a BCL-2 inhibitor. In one variation, the BCL inhibitor is ABT-199.

In yet other embodiments, the one or more additional therapeutic agent may be fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

In other embodiments, the one or more additional therapeutic agent may be a vinca-alkaloid. In one variation, the vinca-alkaloid is selected from the group consisting of vincristine, vinblastine, vindesine, vinorelbine, desoxyvincaminol, vincaminol, vinburnine, vincamajine, and vineridine, and pharmaceutically acceptable salts thereof. In certain variations, at least one vinca-alkaloid is selected from the group consisting of vincristine, vinblastine, vindesine, vinorelbine, desoxyvincaminol, vincaminol, vinburnine, vincamajine, and vineridine and pharmaceutically acceptable salts thereof. In some variations, the vinca-alkaloid is selected from the group consisting of vincristine, vinblastine, vindesine, and vinorelbine, and pharmaceutically acceptable salts thereof. In other variations, the vinca-alkaloid is selected from the group consisting of vincristine and vinblastine, and pharmaceutically acceptable salts thereof. In one variation, the vinca-alkaloid is vincristine and pharmaceutically acceptable salts thereof. In another variation, the vinca-alkaloid is vinblastine and pharmaceutically acceptable salts thereof. Thus, in one aspect, provided is a method for treating cancer in a human in need thereof, comprising administering to the human a bis-mesylate salt of a compound of Formula I, or a hydrate thereof; and a vinca-alkaloid, or a pharmaceutically acceptable salt thereof. In certain aspects, provided is a method for treating cancer in a human in need thereof, comprising administering to the human a hydrate, bis-mesylate salt of a compound of Formula I; and a vinca-alkaloid, or a pharmaceutically acceptable salt thereof. In one aspect, provided is a method of treating cancer in a human in need thereof, comprising administering a monohydrate, bis-mesylate salt of a compound of Formula I; and a vinca-alkaloid, or a pharmaceutically acceptable salt thereof. In certain aspects, provided is a method of treating cancer in a human in need thereof, comprising administering a mesylate salt of Formula IA or IB, or a hydrate thereof; and a vinca-alkaloid, or a pharmaceutically acceptable salt thereof. In other aspects, provided is a method of treating cancer in a human in need thereof, comprising administering a hydrate, mesylate salt of Formula IA or IB; and a vinca-alkaloid, or a pharmaceutically acceptable salt thereof.

In other embodiments, the one or more additional therapies may be any monotherapy or combination therapy suitable for treating leukemia, including, for example, chronic lymphocytic leukemia (CLL), acute lymphocytic leukemia (ALL), and/or acute myeloid leukemia (AML).

In other embodiments, the one or more additional therapeutic agent may be an anti-inflammatory agent. Treatment with the one or more additional therapeutic agent may be prior to, concomitant with, or following treatment with the pharmaceutical composition described herein. In some embodiments, the pharmaceutical composition described herein is combined with another therapeutic agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

The pharmaceutical composition described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a subject (e.g., human) undergoing chemotherapy a chemotherapeutic agent together with the pharmaceutical composition described herein in an amount sufficient to increase the sensitivity of cancer cells to the chemotherapeutic agent is also provided herein. Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the pharmaceutical composition described herein are used in combination with Rituxan® (Rituximab) or other agents that work by selectively depleting CD20+ B-cells.

Included herein are methods of treatment in which the pharmaceutical composition described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNT) receptors antagonists, immunosuppressants and methotrexate. Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an IC50 that is at least 50-fold lower than the IC50 for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates. The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody are used.

In some embodiments, combinations in which at least one therapeutic agent is an immunosuppressant compound such as methotrexate, leflunomide, cyclosporine, tacrolimus, azathioprine, or mycophenolate mofetil are used.

It should be understood that any combinations of the additional therapeutic agents described above may be used, as if each and every combination was individually listed. For example, in certain embodiments, the additional therapeutic agents include a PI3K inhibitor and a LOXL2 inhibitor.

Kits

Kits comprising a pharmaceutical composition comprising a mesylate salt (including, for example, a bis-mesylate salt) of the compound of Formula I, or a hydrate thereof, and at least one pharmaceutical carrier, excipient, adjuvant, or vehicle (e.g., at least one pharmaceutically acceptable polymer) are also provided.

In one aspect, provided is a kit comprising a pharmaceutical composition, comprising: a bis-mesylate salt of a compound of Formula I, or a hydrate thereof; and a pharmaceutical carrier, excipient, adjuvant, or vehicle. In certain aspects, provided is a kit comprising a pharmaceutical composition, comprising: a hydrate, bis-mesylate salt of a compound of Formula I, and a pharmaceutical carrier, excipient, adjuvant, or vehicle. In one aspect, provided is a kit comprising a pharmaceutical composition, comprising: a monohydrate, bis-mesylate salt of a compound of Formula I, and a pharmaceutical carrier, excipient, adjuvant, or vehicle. In certain aspects, provided is a kit comprising a pharmaceutical composition, comprising: a mesylate salt of Formula IA or IB, or a hydrate thereof; and a pharmaceutical carrier, excipient, adjuvant, or vehicle. In other aspects, provided is a kit comprising a pharmaceutical composition, comprising: a hydrate, mesylate salt of Formula IA or IB; and a pharmaceutical carrier, excipient, adjuvant, or vehicle. In one aspect, provided is a kit comprising a pharmaceutical composition, comprising: polymorph Form 3; and a pharmaceutical carrier, excipient, adjuvant, or vehicle. In another aspect, provided is a kit comprising a pharmaceutical composition, comprising: polymorph Form 7; and a pharmaceutical carrier, excipient, adjuvant, or vehicle.

In one variation, the mesylate salt is bis-mesylate salt of Formula IA. In a particular variation, the mesylate salt is Form 3 of bis-mesylate salt of Formula IA, Form 7 of bis-mesylate salt of Formula IA, or a mixture thereof. As described herein, Form 3 and Form 7 are polymorphic forms of a bis-mesylate salt of a compound of Formula I. For example, Form 3 is a polymorph of a monohydrate, bis-mesylate salt of a compound of Formula I.

In one aspect, the kit comprises instructions for use in the treatment of cancer or inflammatory conditions. In a particular variation, the instructions are directed to use of the pharmaceutical composition for the treatment of cancer, including for example, leukemia or lymphoma. In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), and marginal zone lymphoma (MZL). In certain embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). In some embodiments, the cancer is MCL, DLBCL, iNHL, FL, MZL, LPL, SLL, or WM. In other embodiments, the cancer is CLL, MCL, DLBCL, iNHL (including, for example, non-FL iNHL), or FL.

The non-Hodgkin lymphoma encompasses the indolent B-cell diseases that include for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL). In another embodiment, the cancer is non-FL iNHL.

In a particular variation, the instructions are directed to use of the pharmaceutical composition for the treatment of an autoimmune disease. Certain embodiments of an autoimmune disease include asthma, rheumatoid arthritis, multiple sclerosis, and lupus.

Any pharmaceutical composition provided in the present disclosure may be used in the kits, the same as if each and every composition were specifically and individually listed for use a kit. For example, in one embodiment a kit may comprise: a) about 34% w/w of a mesylate salt (including, for example, a mono-mesylate or bis-mesylate salt) of a compound of Formula I; b) about 15% w/w HPMC; c) about 22% w/w mannitol; d) about 10% w/w crospovidone; and e) about 1% w/w to about 3% w/w poloxamer. In another embodiment, a kit may comprise: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of a monohydrate, bis-mesylate salt of a compound of Formula I; b) about 15% w/w HPMC; c) about 22% w/w mannitol; d) about 10% w/w crospovidone; and e) about 1% w/w to about 3% w/w poloxamer. In yet another embodiment, a kit may comprise: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

Articles of Manufacture

Articles of manufacture comprising a container in which a pharmaceutical composition comprising a mesylate salt (including, for example, a bis-mesylate salt) of a compound of Formula I and at least one pharmaceutically acceptable polymer are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

In one aspect, provided is an article of manufacture comprising a bis-mesylate salt of a compound of Formula I, or a hydrate thereof. In certain aspects, provided is an article of manufacture comprising a hydrate, bis-mesylate salt of a compound of Formula I. In one aspect, provided is an article of manufacture comprising a monohydrate, bis-mesylate salt of a compound of Formula I. In certain aspects, provided is an article of manufacture comprising a mesylate salt of Formula IA or IB, or a hydrate thereof. In other aspects, provided is an article of manufacture comprising a hydrate, mesylate salt of Formula IA or IB. In one aspect, provided is an article of manufacture comprising polymorph Form 3. In one aspect, provided is an article of manufacture comprising polymorph Form 7. In any of the foregoing embodiments, the article of manufacture may further comprise a label containing instructions for use of the mesylate salt.

Unit dosage forms of the pharmaceutical composition comprising a mesylate salt (including, for example, a mono-mesylate or bis-mesylate salt) of a compound of Formula I and at least one pharmaceutically acceptable polymer are also provided.

In one aspect, provided is a unit dosage comprising a bis-mesylate salt of a compound of Formula I, or a hydrate thereof. In certain aspects, provided is a unit dosage comprising a hydrate, bis-mesylate salt of a compound of Formula I. In one aspect, provided is a unit dosage comprising a monohydrate, bis-mesylate salt of a compound of Formula I. In certain aspects, provided is a unit dosage comprising a mesylate salt of Formula IA or IB, or a hydrate thereof. In other aspects, provided is a unit dosage comprising a hydrate, mesylate salt of Formula IA or IB. In one aspect, provided is a unit dosage comprising polymorph Form 3. In one aspect, provided is a unit dosage comprising polymorph Form 7. In any of the foregoing embodiments, the unit dosage is a tablet.

In some embodiments, the unit dosage form comprises from about 10 mg to about 1800 mg, or about 10 mg to about 1500 mg, or about 10 mg to about 1300 mg, or about 10 mg to about 1000 mg, or about 10 mg to about 800 mg, or about 10 mg to about 600 mg, or about 10 mg to about 300 mg, or about 10 mg to about 200 mg, or about 10 mg to about 100 mg, or about 100 mg to about 800 mg, or about 100 mg to about 600 mg, or about 100 mg to about 300 mg, or about 100 mg to about 200 mg, or about 200 mg to about 350 mg, or about 250 mg to about 300 mg, or about 200 mg to about 400 mg, or about 400 mg to about 600 mg, or about 400 mg to about 800 mg, or about 600 mg or about 800 mg, or about 800 mg to about 1200 mg, or about 1200 mg to about 1600 of a mesylate salt of a compound of Formula I, or a hydrate thereof; or in certain embodiments, of a mono-mesylate or bis-mesylate salt of a compound of Formula I, a hydrate thereof; or in one embodiment, of a monohydrate, bis-mesylate salt of a compound of Formula I; or in another embodiment, polymorph Form 3, polymorph Form 7, or a combination thereof. In certain embodiments, the unit dosage form comprises about 25 mg, about 50 mg, about 75 mg, about 100 mg, about 200 mg, about 250 mg, about 300 mg, about 350 mg, about 400 mg, about 450 mg, about 500 mg, about 550 mg, about 600 mg, about 700 mg, about 800 mg, about 900 mg, about 1000 mg, about 1100 mg, about 1200 mg, or about 1300 mg of a mesylate salt of a compound of Formula I, or a hydrate thereof; or in certain embodiments, of a mono-mesylate or bis-mesylate salt of a compound of Formula I, a hydrate thereof; or in one embodiment, of a monohydrate, bis-mesylate salt of a compound of Formula I; or in another embodiment, polymorph Form 3, polymorph Form 7, or a combination thereof.

In some of the foregoing embodiments, the unit dosage form further comprises at least one pharmaceutically acceptable carrier.

The dosages for oral administration described above may be administered once daily (QD) or twice daily (BID). In some embodiments, a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof, or a pharmaceutical composition of any of the foregoing, is administered orally at a unit dosage of about 1 mg QD, about 2 mg QD, about 5 mg QD, about 10 mg QD, about 15 mg QD, about 20 mg QD, about 25 mg QD, about 30 mg QD, about 35 mg QD, about 40 mg QD, about 45 mg QD, about 50 mg QD, about 75 mg QD, about 100 mg QD, about 125 mg QD, about 150 mg QD, about 175 mg QD, about 200 mg QD, about 225 mg QD, about 250 mg QD, about 300 mg QD, about 350 mg QD, about 400 mg QD, about 450 mg QD, about 500 mg QD, about 550 mg QD, about 600 mg QD, about 650 mg QD, about 700 mg QD, about 750 mg QD, about 800 mg QD, about 850 mg QD, about 900 mg QD, about 950 mg QD, or about 1000 mg QD. In some embodiments, a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof, or a pharmaceutical composition of any of the foregoing, is administered orally at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID.

For example, in certain variations, provided is a tablet comprising a mesylate salt of a compound of Formula I, or a hydrate thereof; or in certain embodiments, a mono-mesylate or bis-mesylate salt of a compound of Formula I, a hydrate thereof; or in one embodiment, a monohydrate, bis-mesylate salt of a compound of Formula I; or in another embodiment, polymorph Form 3, polymorph Form 7, or a combination thereof, wherein the tablet is administered orally to a human in need thereof at a unit dosage of about 1 mg BID, about 2 mg BID, about 5 mg BID, about 10 mg BID, about 15 mg BID, about 20 mg BID, about 25 mg BID, about 30 mg BID, about 35 mg BID, about 40 mg BID, about 45 mg BID, about 50 mg BID, about 75 mg BID, about 100 mg BID, about 125 mg BID, about 150 mg BID, about 175 mg BID, about 200 mg BID, about 225 mg BID, about 250 mg BID, about 300 mg BID, about 350 mg BID, about 400 mg BID, about 450 mg BID, about 500 mg BID, about 550 mg BID, about 600 mg BID, about 650 mg BID, about 700 mg BID, about 750 mg BID, about 800 mg BID, about 850 mg BID, about 900 mg BID, about 950 mg BID, or about 1000 mg BID. In one variation of the foregoing, the human has a condition selected from the group consisting of lymphoplasmacytic lymphoma/Waldestrom's macroglobulinemia (LPL/WM), small lymphocytic lymphoma (SLL), marginal zone lymphoma (MZL), follicular lymphoma (FL), diffuse large B-cell lymphoma (DLBCL), mantle cell lymphoma (MCL), and chronic lymphocytic leukemia (CLL), or any combination thereof. In another variation of any of the foregoing, the human is (i) refractory to, and/or (ii) in relapse after treatment with at least one therapy for a non-FL indolent non-Hodgkin's lymphoma. In certain embodiments, the non-FL indolent non-Hodgkin's lymphoma is lymphoplasmacytic lymphoma/Waldestrom's macroglobulinemia (LPL/WM), small lymphocytic lymphoma (SLL), or marginal zone lymphoma (MZL)). In another variation, the human is (i) refractory to, and/or (ii) in relapse after treatment with at least one therapy for follicular lymphoma (FL). In another variation, the human is (i) refractory to, and/or (ii) in relapse after treatment with at least one therapy for diffuse large B-cell lymphoma (DLBCL). In another variation, the human is (i) refractory to, and/or (ii) in relapse after treatment with at least one therapy for mantle cell lymphoma (MCL). In yet another variation, the human is (i) refractory to, and/or (ii) in relapse after treatment with at least one therapy for chronic lymphocytic leukemia (CLL). In yet another variation, the human is (i) refractory to, and/or (ii) in relapse after treatment with a phosphatidylinositol 3-kinase (PI3K) inhibitor, a bruton tyrosine kinase (BTK) inhibitor, or a B-cell receptor (BCR) treatment for chronic lymphocytic leukemia (CLL).

Any pharmaceutical composition provided in the present disclosure may be used in the articles of manufacture, the same as if each and every composition were specifically and individually listed for use an article of manufacture. For example, in one embodiment, an article of manufacture may comprise: a) about 34% w/w of a mesylate salt (including, for example, a mono-mesylate or bis-mesylate salt) of a compound of Formula b) about 15% w/w HPMC; c) about 22% w/w mannitol; d) about 10% w/w crospovidone; and e) about 1% w/w to about 3% w/w poloxamer. In another embodiment, an article of manufacture may comprise: a) about 34% w/w of a bis-mesylate salt of a compound of Formula I, or a hydrate thereof; b) about 15% w/w HPMC; c) about 22% w/w mannitol; d) about 10% w/w crospovidone; and e) about 1% w/w to about 3% w/w poloxamer. In yet another embodiment, an article of manufacture may comprise: a) about 34% w/w of a monohydrate, bis-mesylate salt of a compound of Formula I; b) about 15% w/w HPMC, c) about 22% w/w mannitol; d) about 10% w/w crospovidone; and e) about 1% w/w to about 3% w/w poloxamer. In yet another embodiment, an article of manufacture may comprise: a) about 34% w/w of polymorph Form 3, polymorph Form 7, or a combination thereof; b) about 15% w/w HPMC; c) about 22% w/w mannitol; d) about 10% w/w crospovidone; and e) about 1% w/w to about 3% w/w poloxamer.

EXAMPLES

The following examples are included to illustrate preferred embodiments of the disclosure. It should be appreciated by those of skill in the art that the techniques disclosed herein represent techniques that apply in the practice of the disclosure. Those of skill in the art should, in light of the present disclosure, appreciate that changes can be made in the and still obtain a like or similar result without departing from the spirit and scope of the disclosure.

The polymorphs described herein may be characterized by various methods known in the art, such as X-ray powder diffraction pattern (XRPD), differential scanning calorimetry (DSC), thermal gravimetric analysis (TGA), dynamic vapor sorption (DVS), single crystal X-ray diffraction, nuclear magnetic resonance (NMR, e.g., $^1$H NMR), including, for example, the methods described in Examples 4A, 4B, 4C, 5A, 5B, 6A, 6B and 11. With respect to polymorph Form 3, exemplary XRPD patterns are provided in FIGS. 1A and 1B; exemplary DSC and TGA profiles are provided in FIGS. 3A, 3B and 3C; exemplary DVS plots are provided in FIGS. 5A and 5C; and an exemplary $^1$H NMR spectrum is provided in FIG. 13. With respect to polymorph Form 7, representative XRPD patterns are provided in FIGS. 2A and 2B; exemplary DSC and TGA data are provided in FIGS. 4A, 4B and 4C; exemplary DVS plots are provided in FIGS. 5B and 5D; and an exemplary $^1$H NMR spectrum is provided in FIG. 14.

In the following Examples, the term "X" refers to weight equivalents, and "V" refers to volume equivalents. "RH" refers to relative humidity.

Example 1: Synthesis of Polymorph Form 3

Methods for generally making various forms of the compound of Formula I may be found in U.S. Pat. Nos. 8,450,321 and 8,455,493. The following is a method for producing polymorph Form 3, which is a polymorph of a monohydrate, bis-mesylate salt of a compound of Formula I (and may also be described as a polymorph of a monohydrate of the compound of Formula IA shown in the reaction scheme below).

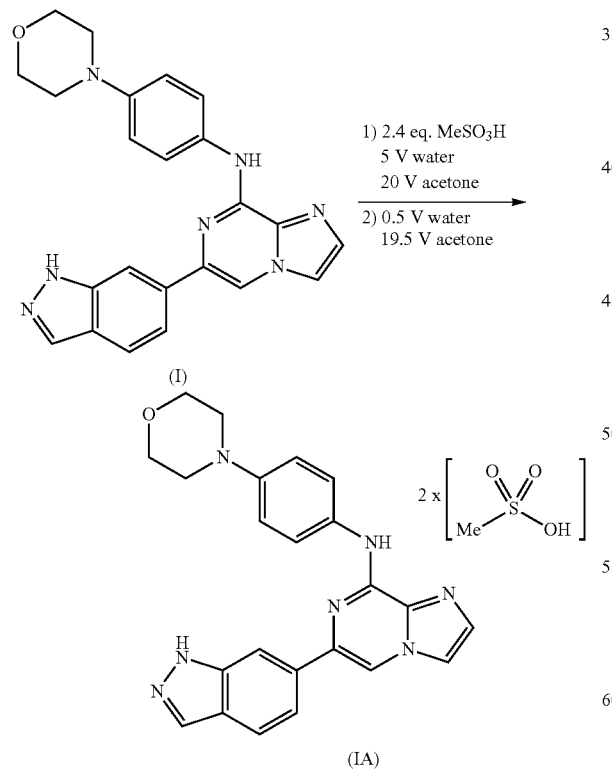

Figure 4A:
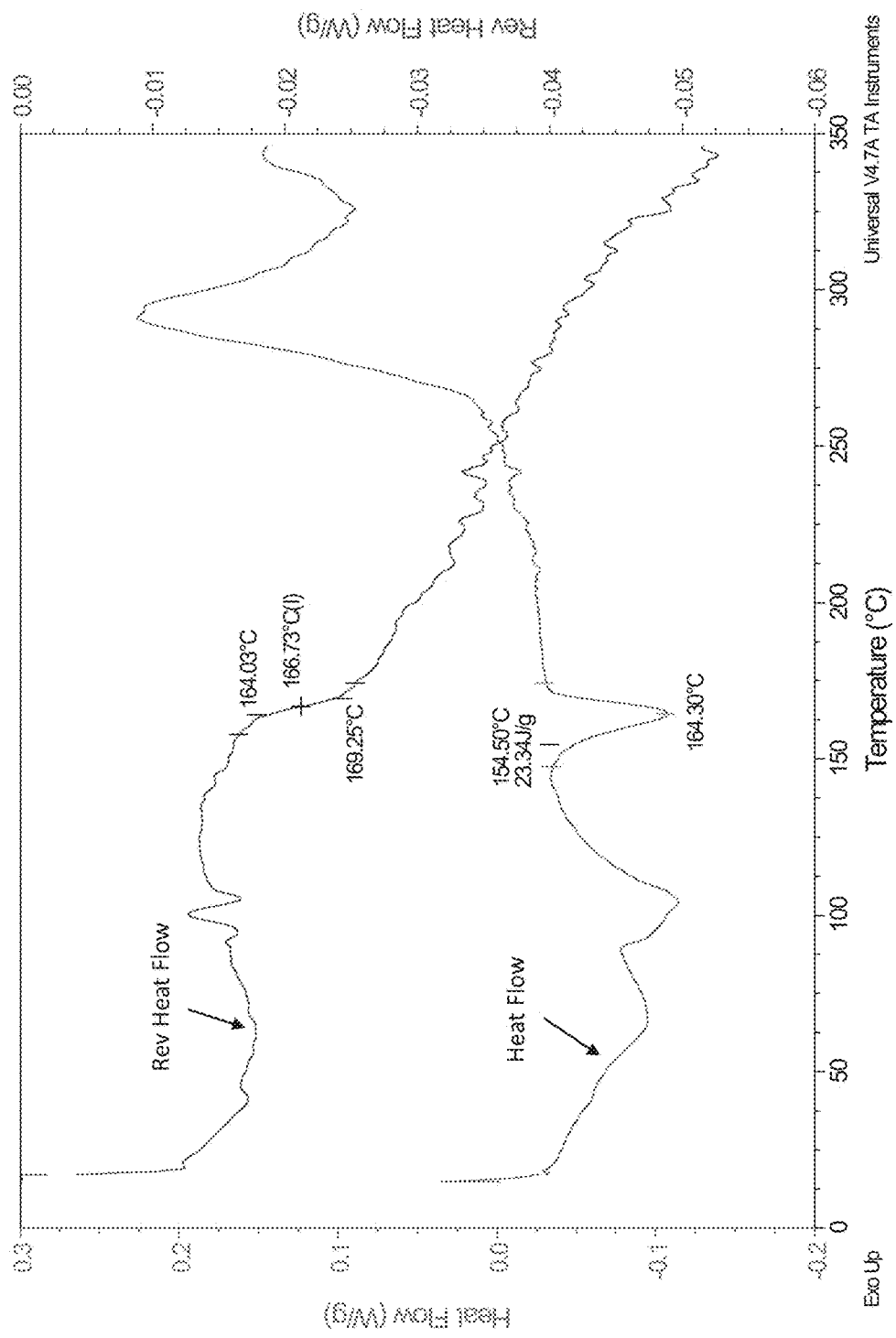
FIG. 4A is an exemplary DSC plot of polymorph Form 7.
Figure 5:
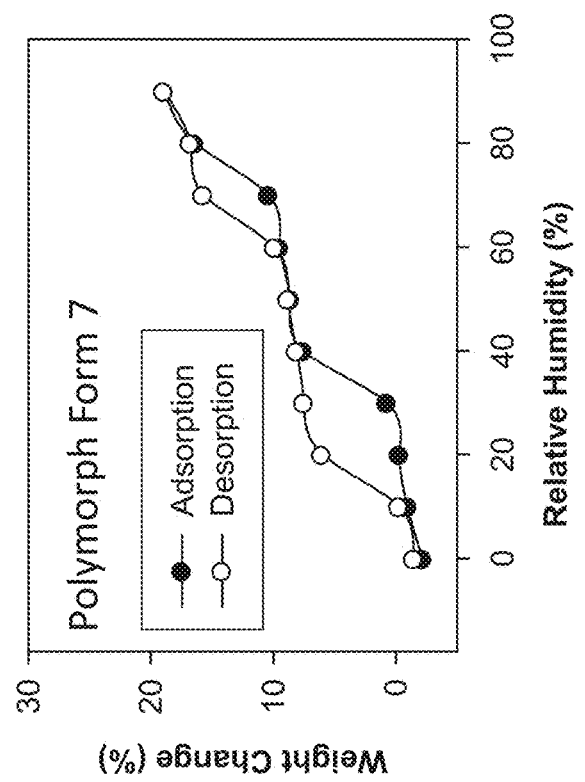
FIG. 5 shows the results of dynamic vapor sorption (DVS) plot of polymorph Form 3 (panel (A)), and DVS plot of polymorph Form 7 (panel (B)).
Figure 5:
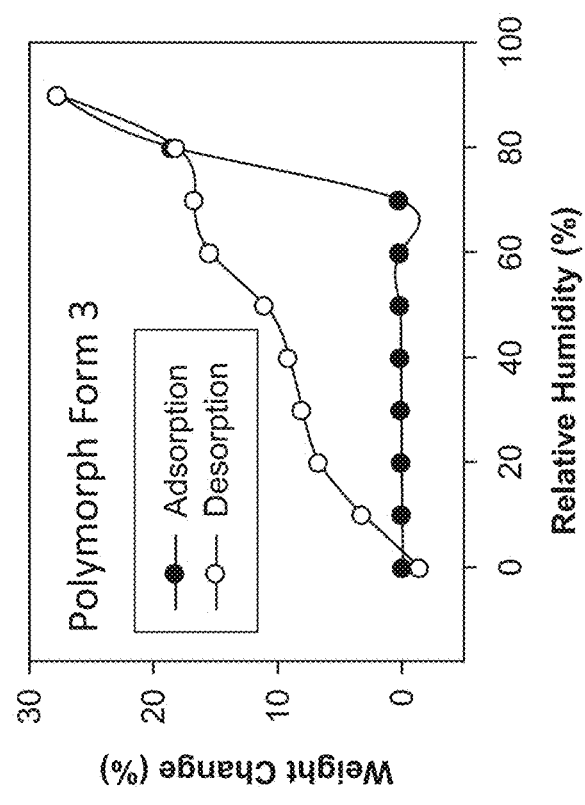

A compound of Formula I (1.0x) was added to Reactor A. Methanesulfonic acid (0.56x, 2.40 eq), water (4x, 4 V) and acetone (3.2x, 4 V) were added to Reactor B. The contents of Reactor B were added to Reactor A while maintaining the temperature in Reactor A below 35° C. After the solids dissolved, the contents of Reactor A were transferred to Reactor B. Reactor A was rinsed with water (1x, 1 V) and acetone (0.8x, 1 V), and transferred to Reactor B. The temperature of Reactor B was adjusted to 19-25° C. Under high agitation, acetone (11.9x, 15 V) was added to Reactor B. The temperature of Reactor B was adjusted to 0-6° C. and the contents of Reactor B were mixed for 5 h, then filtered, and rinsed with acetone (4.0x, 5 V) to provide polymorph Form 7. Form 7 was dried under vacuum at 60° C. until constant weight was achieved. Representative patterns of XRPD and DSC of polymorph Form 7 are shown in FIGS. 2A and 4A, respectively.

The isolated polymorph Form 7 was added to polymorph Form 3 seeds of a compound of Formula IA (0.01x, 1 mol %) in Reactor B. Acetone (15.4x, 19.5 V), and water (0.5x, 0.5 V) were added to Reactor B and mixed at 19-25° C.' until polymorph Form 7 was converted to Form 3. The conversion was monitored by XRPD or DSC. The contents of Reactor B was filtered, rinsed with acetone (2.4x, 3 V) and dried under vacuum at 60° C. until constant weight was achieved. Representative patterns of XRPD and DSC of polymorph Form 3 of a compound of Formula IA are shown in FIGS. 1A and 3A, respectively. Other representative patterns of XRPD and DSC of polymorph Form 3 of a compound of Formula IA are shown in FIGS. 1B and 3C, respectively.

Example 2: Alternative Synthesis of Polymorph Form 3

The following is a method for producing polymorph Form 3, a monohydrate, bis-mesylate salt of a compound of Formula I (which may also be described as a polymorph of a monohydrate of the compound of Formula IA shown in the reaction scheme below).

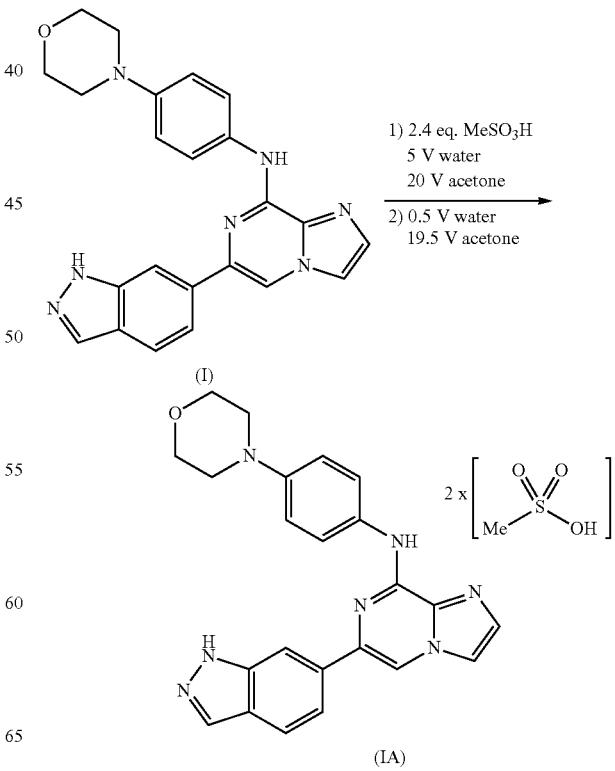

Polymorph Form 7 was obtained as described in Example 1.

The isolated polymorph Form 7 was added to polymorph Form 3 seeds of a compound of Formula IA (0.01×, 1 mol %) in Reactor B. Acetone (15.0×, 19.0 V), and water (1.0×, 1.0 V) were added to Reactor B. The contents of the Reactor B were heated to reflux (about 55° C.) until polymorph Form 7 was converted to Form 3. The conversion was monitored by XRPD or DSC. The contents of Reactor B was a slurry and was cooled to 19-25° C., then filtered, rinsed with acetone (2.4×, 3 V) and dried under vacuum at 60° C. until constant weight is achieved to provide the polymorph Form 3. Representative patterns of XRPD and DSC of polymorph Form 3 of a compound of Formula IA are shown in FIGS. 1A and 3A, respectively. Other representative patterns of XRPD and DSC of polymorph Form 3 of a compound of Formula IA are shown in FIGS. 1B and 3C, respectively.

Example 3: One-Pot Synthesis of Polymorph Form 3

The following is a method for producing polymorph Form 3, a monohydrate, bis-mesylate salt of a compound of Formula I (which may also be described as a polymorph of a monohydrate of the compound of Formula IA shown in the reaction scheme below) from a compound of Formula I (as a the free base). The described method uses a single reactor in the conversion of a compound of Formula I to polymorph Form 3, and does not require isolation of a compound intermediate.

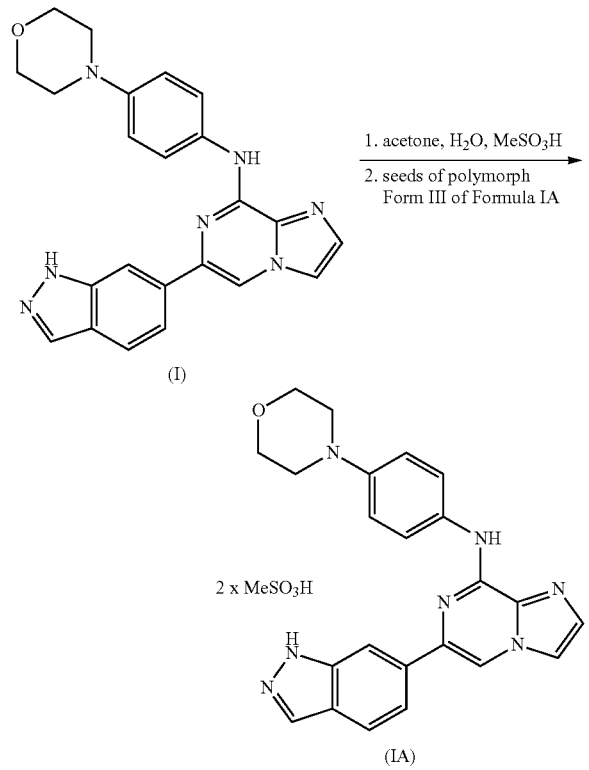

A compound of Formula I (1.0×) was added to acetone (14.2×, 18V) in Reactor A and mixed. Water (0.8×, 0.8V) was added to Reactor A, followed by methanesulfonic acid, (0.48×, 2.05 eq). Acetone (0.9×, 1.2 V) was pumped through to rinse the lines forward to Reactor A with acetone. The contents of Reactor A were heated to reflux (about 55° C.) for about 2 hours. Polymorph Form 3 seeds (0.015×, 1 mol %) were added to Reactor A and the contents mixed at reflux to convert a compound of Formula IA to polymorph Form 3. The conversion was monitored by XRPD. The contents of the reactor were cooled to 19-25° C., filtered, rinsed with acetone (4.0×, 5 V), and dried under vacuum at 60° C. Representative patterns of XRPD and DSC of polymorph Form 3 of a compound of Formula IA are shown in FIGS. 1A and 3A, respectively. Other representative patterns of XRPD and DSC of polymorph Form 3 of a compound of Formula IA are shown in FIGS. 1B and 3C, respectively.

Example 4A: Polymorph Form 3 and Polymorph Form 7 XRPD Measurements

This example describes the experimental conditions and data for XRPD measurements of polymorph Form 3 and polymorph Form 7.

Polymorph Form 3

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror. Prominent peaks are selected from observed peaks by identifying preferably non-overlapping, low-angle peaks, with strong intensity.

An exemplary XRPD pattern of polymorph Form 3 is shown in FIG. 1A. With reference to FIG. 1A, characteristic XRPD 2θ-reflections (±0.2 degrees) for Form 3 are 13.75, 16.90, 22.88, and 26.06.

Polymorph Form 7

XRPD patterns were collected using a PANalytical X'Pert MPD Pro Powder X-Ray Diffractometer configured with reflectance stage with spinning, data acquisition range: 2-40 degrees 2θ, Copper (Cu) anode; Kα1/Kα2 radiation; tube current 40 mA; tube tension 45 kV; automatic divergence and anti-scatter slits. Samples were prepared for analysis by distributing solid material as a thin layer on a silicon holder. Each holder was mounted on a reflectance/transmittance stage and rotated during data acquisition.

An exemplary XRPD pattern of polymorph Form 7 is shown in FIG. 2A. With reference to FIG. 2A, characteristic XRPD 2θ-reflections (±0.2 degrees) for Form 7 are 4.94, 9.82, and 26.68.

Example 4B: Polymorph Form 3 and Polymorph Form 7 XRPD Measurements

This example describes experimental conditions and data for XRPD measurements of polymorph Form 3 and polymorph Form 7.

X-Ray Powder Diffraction (XRPD) patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multi layer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v15.0.0.0.

Ambient conditions: Samples run under ambient conditions were prepared as flat plate specimens using powder as received without grinding. Approximately 1-2 mg of the sample was lightly pressed on a glass slide to obtain a flat surface.

Non-ambient conditions: Samples run under non-ambient conditions were mounted on a silicon wafer with heat-conducting compound. The sample was then heated to the appropriate temperature at 20° C./min and subsequently held isothermally for 1 minute before data collection was initiated.

Example 4C: Polymorph Form 3 and Polymorph Form 7 XRPD Measurements

This example describes experimental conditions and data for XRPD measurements of polymorph Form 3 and polymorph Form 7.

X-Ray Powder Diffraction (XRPD) patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42° 2θ
Step size: 0.05° 2θ
Collection time: 0.5 s/step Samples run under non-ambient conditions: Approximately 40 mg of the sample was placed in a Ni-coated sample holder under ambient conditions. The sample was loaded at 25° C. The sample was then heated to the appropriate temperature. The details of the data collection are:
Angular range: 3 to 30° 2θ
Step size: 0.05° 2θ
Collection time: 0.5 s/step

Example 5A: Polymorph Form 3 and Polymorph Form 7 DSC Measurements

This example describes the experimental conditions and data for Modulated Differential Scanning calorimetry (mDSC) and Thermal Gravimetric Analysis (TGA) measurements of polymorph Form 3 and polymorph Form 7.

DSC was performed with approximately 2 to 5 mg of solid in an aluminum pan with a pinhole, heated at 2° C./min with a modulation of ±0.8° C. every 60 seconds under dried nitrogen purge using TA instruments (New Castle, Del., USA) model 1000. TGA was performed with approximately 2 to 5 mg of solid heated at a rate of 2 or 10° C./min using TA Instruments (New Castle, Del., USA) model 500.

Polymorph Form 3

The DSC thermogram and the overlay of the DSC and TGA thermograms of polymorph Form 3 are shown in FIGS. 3A and 3B, respectively. The characteristic DSC pattern of Form 3 was observed to have three endotherms that onset at 109° C., 206° C., and 255° C. The major event in the DSC thermogram observed was melting at 260° C. with concurrent decomposition. A minor endotherm was observed at ~170° C. and a minor exotherm at ~210° C. the origins of which were unknown. The TGA thermogram of Form 3 in this example shows a step change of ~3% between the temperature of 75° C. and 100° C. which could be due to loss of residual solvent. Another step change around 200° C. was observed, which coincides with the small exotherm on the DSC thermogram. The major decomposition was observed to start around 230° C.

Polymorph Form 7

Figure 4B:
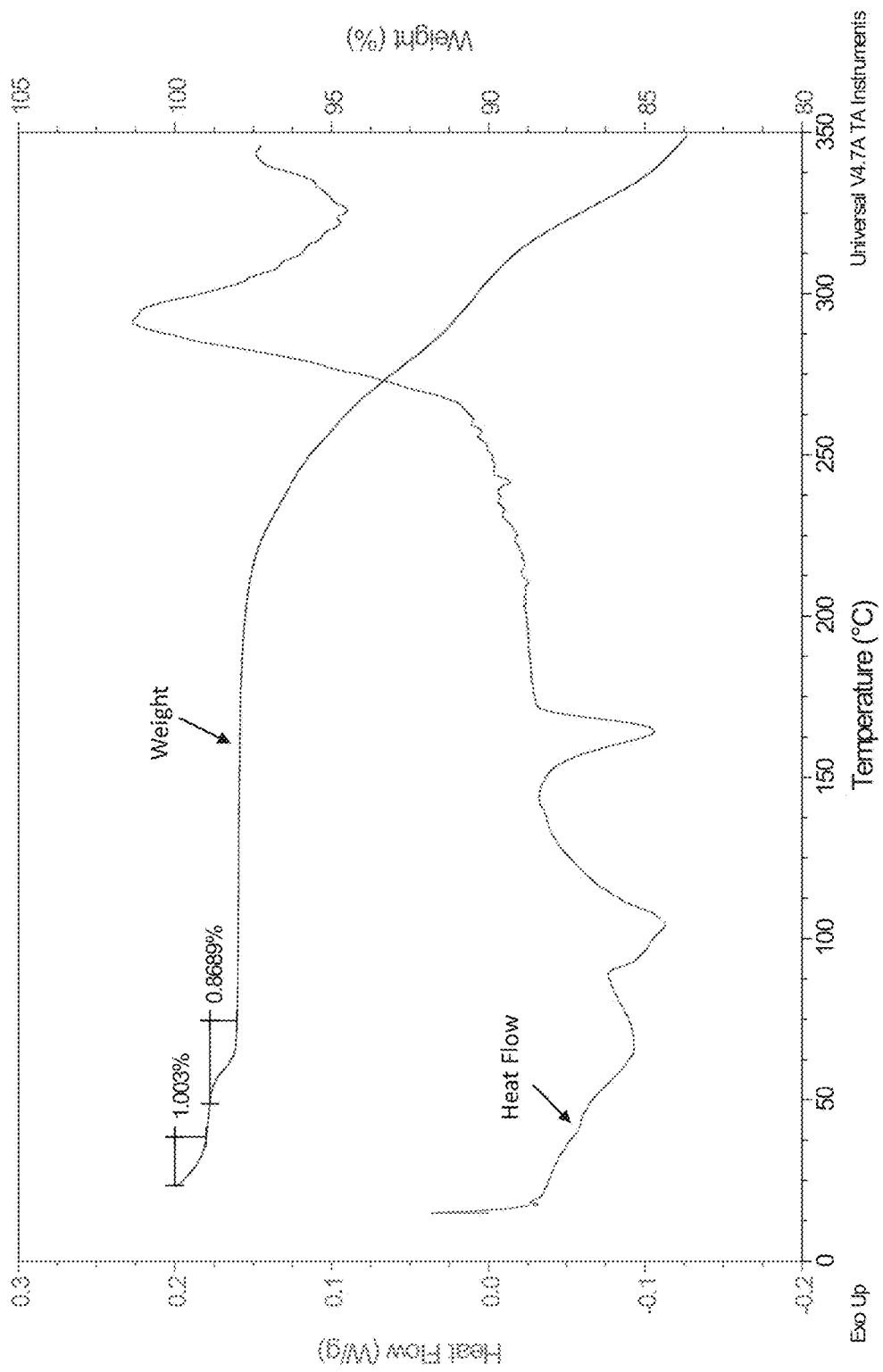
FIGS. 4B and 4C are exemplary DSC and TGA plots of polymorph Form 7.

The DSC thermogram and the overlay of the DSC and TGA thermograms of Form 7 are shown in FIGS. 4A and 4B, respectively. Two small endothermy were observed at ~110° C. and 170° C. prior to the onset of decomposition at ~280° C. The reversing heat flow show a typical tg at 170° C. which may indicate that the endotherm shown on the total heat flow at the same temperature is not a melting event. These thermal properties may be consistent with a liquid crystal state. The TGA thermogram of Form 7 shows two step changes of ~1% each below 80° C. which could be due to loss of residual solvent. The onsite of decomposition was observed at ~220° C. which is similar to the DSC thermogram.

Example 5B: Polymorph Form 3 and Polymorph Form 7 DSC Measurements

This example describes the experimental conditions and data for Differential Scanning calorimetry (DSC) and Thermal Gravimetric Analysis (TGA) measurements of polymorphs Form 3 and Form 7.

DSC data were collected on a Mettler DSC 823E equipped with a 34 position auto-sampler. The instrument was calibrated for energy and temperature using certified indium. Typically 0.5-3 mg of each sample, in a pin-holed aluminum pan, was heated at 10° C./min from 25° C. to 300° C. A nitrogen purge at 50 ml/ruin was maintained over the sample. The instrument control and data analysis software was STARe v12.1. TGA data were collected on a Mettler TGA/SDTA 851e equipped with a 34 position auto-sampler. The instrument was temperature calibrated using certified indium. Typically 5-30 mg of each sample was loaded onto a pre-weighed aluminum crucible and was heated at 10° C./min from ambient temperature to 350° C. A nitrogen purge at 50 ml/min was maintained over the sample. The instrument control and data analysis software was STARe v12.1.

Figure 4C:
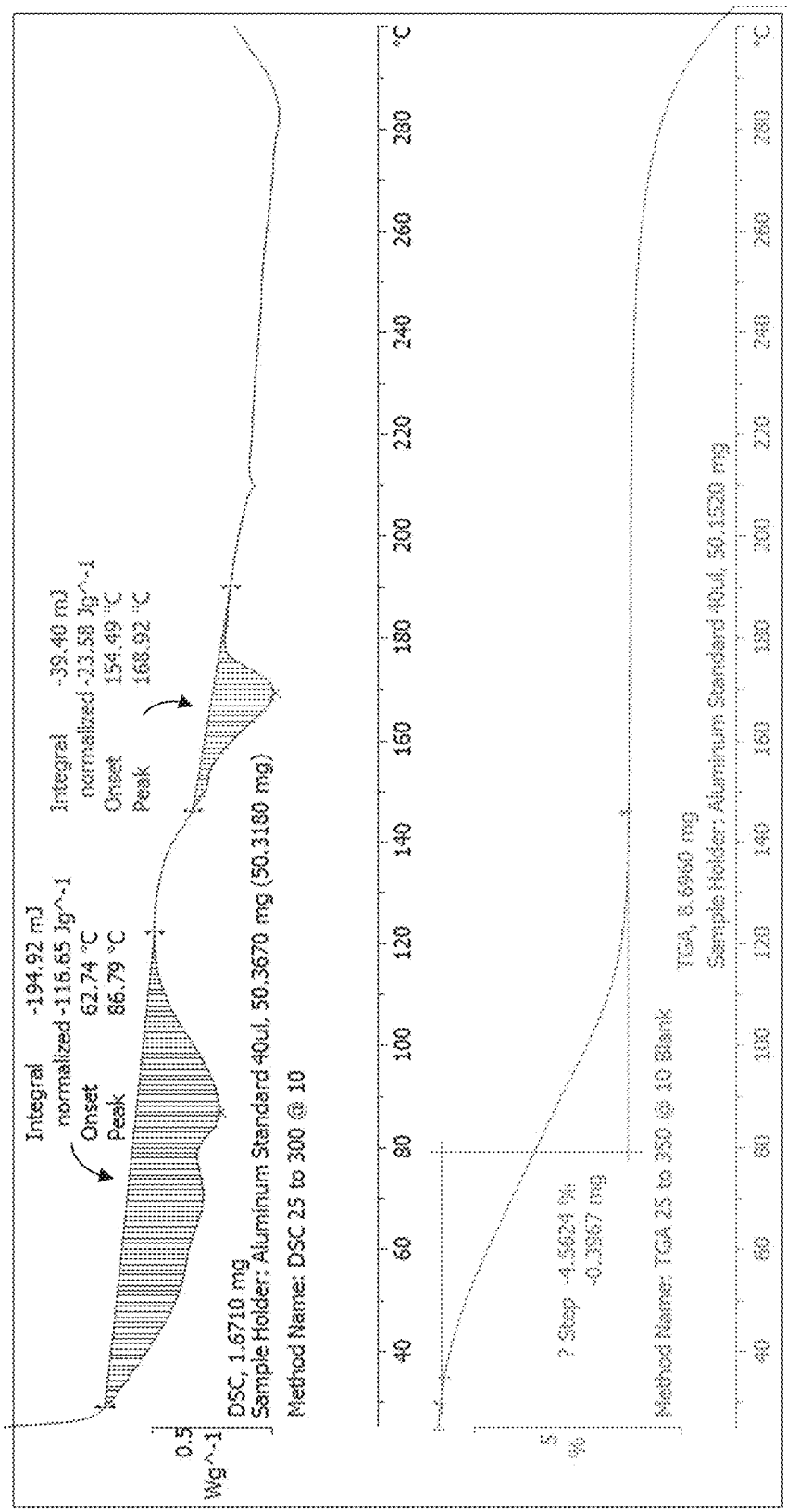

Exemplary DSC and TGA thermograms of polymorph Form 3 and polymorph Form 7 are shown in FIGS. 3C and 4C, respectively.

Example 6A: Hygroscopicity Studies of Polymorph Form 3 and Polymorph Form 7

This example demonstrates the superior physical stability of polymorph Form 3 compared to polymorph Form 7.

Hygroscopicity of polymorph Form 3 and polymorph Form 7 at 25° C. was determined by dynamic vapor sorption (DVS) using an automated vapor sorption balance (Q5000SA; TA instruments, New Castle, Del.). Hygroscopicity was studied as a function of relative humidity (RH) over the range of 0 to 90%. Approximately 10 mg of solid sample was placed directly onto the 13 mm quartz DVS sample cup and equilibrated at 0% relative humidity (RH) until a constant weight was achieved. After equilibration, the RH was increased in increments of 10% to reach 90%, and the water sorption was monitored. For desorption, the relative humidity was deceased in a similar manner to accomplish a full sorption/desorption cycle.

For all experiments, the instrument was operated in dm/dt mode (mass variation over time) to determine when equilibrium was reached. A fixed dm/dt value of 0.0010% min$^{-1}$ was selected for all RH segments. A maximum stage of 360 minutes and a minimum stage of 60 minutes were selected for these experiments.

Figure 6:
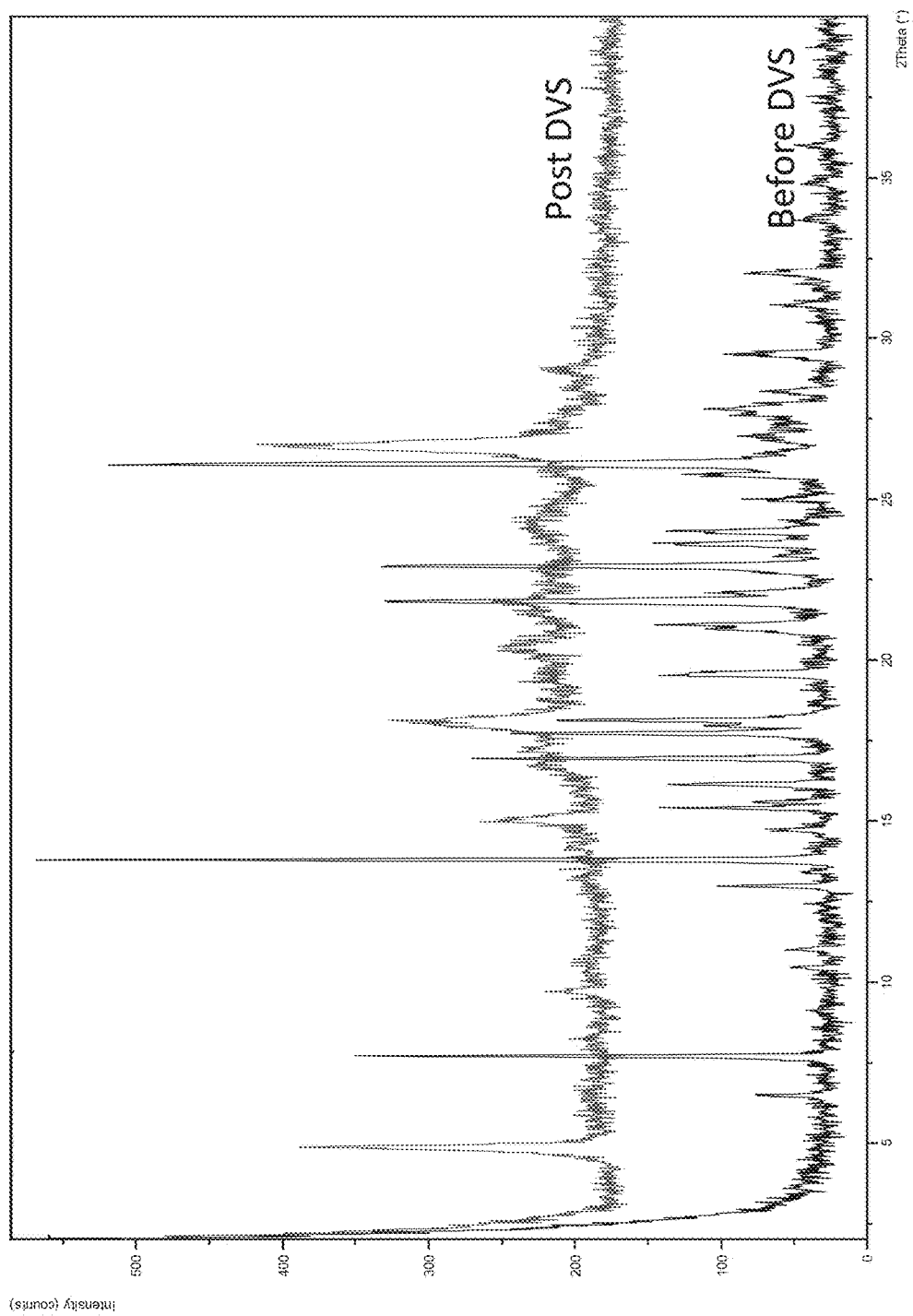
FIG. 6 is an XRPD pattern of polymorph Form 3 before and after DVS measurements.

Polymorph Form 3 was not observed to be hygroscopic at 70% RH and below. Above 70% RH, it was observed to absorb a large amount of moisture. At 90%, the water adsorption was observed to reach ~28%. The water adsorption was observed to be irreversible as indicated by the existence of a big hysteresis. At the end of the DVS experiment, sample was collected and analyzed by XRPD which showed the sample had converted to Form 7. See FIG. 6.

Polymorph Form 7 was observed to be highly hygroscopic. It was observed to continuously adsorb water at all tested RH's. At 40% RH, the weight gain was observed to be nearly 10%. However, the weight gain at 90% RH was observed to be ~22% which is lower than that of Form 3. As RH decreases, the sample loses weight and the weight gain were observed to return to near zero at 0% RH.

In summary, at up to 70% RH, polymorph Form 3 was not observed to be hygroscopic and exhibits increased stability compared to Form 7 which adsorbs water below 70% RH.

Example 6B: Hygroscopicity Studies of Polymorphs Form 3 and Form 7

This example demonstrates the physical stabilities of polymorph Form 3 and polymorph Form 7.

Sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 ml/min. The relative humidity (RH) was measured by a calibrated Vaisala RH probe (dynamic range of 0-95% RH), located near the sample. The weight change, (mass relaxation) of the sample as a function of % RH was constantly monitored by the microbalance (accuracy±0.001 mg).

10-20 mg of sample was placed in a tared mesh stainless steel basket under ambient conditions. The sample was loaded and unloaded at 40% RH and 25° C. (typical room conditions).

A moisture sorption isotherm was performed as outlined in Table 1 below (2 scans giving 1 complete cycle). The standard isotherm was performed at 25° C. at 10% RH intervals over a 0-90% RH range.

TABLE 1

Method Parameters for Hiden IGA Sorp Experiments

| Parameters | Values |
| --- | --- |
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (ml/min) | 250 |
| Temperature (° C.) | 25 |
| Stability (° C./min) | 0.05 |
| Minimum Sorption Time (hours) | 1 |
| Maximum Sorption Time (hours) | 4 |
| Mode | AF2 |
| Accuracy (%) | 98 |

The software uses a least squares minimization procedure together with a model of the mass relaxation, to predict an asymptotic value. The measured mass relaxation value must be within 5% of that predicted by the software, before the next % RH value is selected. The minimum equilibration time was set to 1 hour and the maximum to 4 hours. Data analysis was carried out using IGASorp Systems Software v 6.50.55. The sample was recovered after completion of the isotherm and re-analyzed by XRPD.

In other cases, sorption isotherms were also obtained using a SMS DVS Intrinsic moisture sorption analyser, controlled by DVS Intrinsic Control software v1.0.1.2 (or v 1.0.1.3). The sample temperature was maintained at 25° C. by the instrument controls. The humidity was controlled by mixing streams of dry and wet nitrogen, with a total flow rate of 200 ml/min The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg).

5-20 mg of sample was placed in a tared mesh stainless steel basket under ambient conditions. The sample was loaded and unloaded at 40% RH and 25° C. (typical room conditions). A moisture sorption isotherm was performed as outlined in Table 2 below (2 scans giving 1 complete cycle). The standard isotherm was performed at 25° C. at 10% RH intervals over a 0-90% RH range. Data analysis was carried out using Microsoft Excel using DVS Analysis Suite v6.2 (or 6.1 or 6.0). The sample was recovered after completion of the isotherm and re-analyzed by XRPD.

TABLE 2

Method Parameters for SMS DVS Intrinsic Experiments

| Parameter | Value |
| --- | --- |
| Adsorption - Scan 1 | 40-90 |
| Desorption/Adsorption - Scan 2 | 90-0, 0-40 |
| Intervals (% RH) | 10 |
| Number of Scans | 2 |
| Flow rate (ml/min) | 200 |
| Temperature (° C.) | 25 |
| Stability (° C./min) | 0.2 |
| Sorption Time (hours) | 6 hour time out |

Figure 5C:
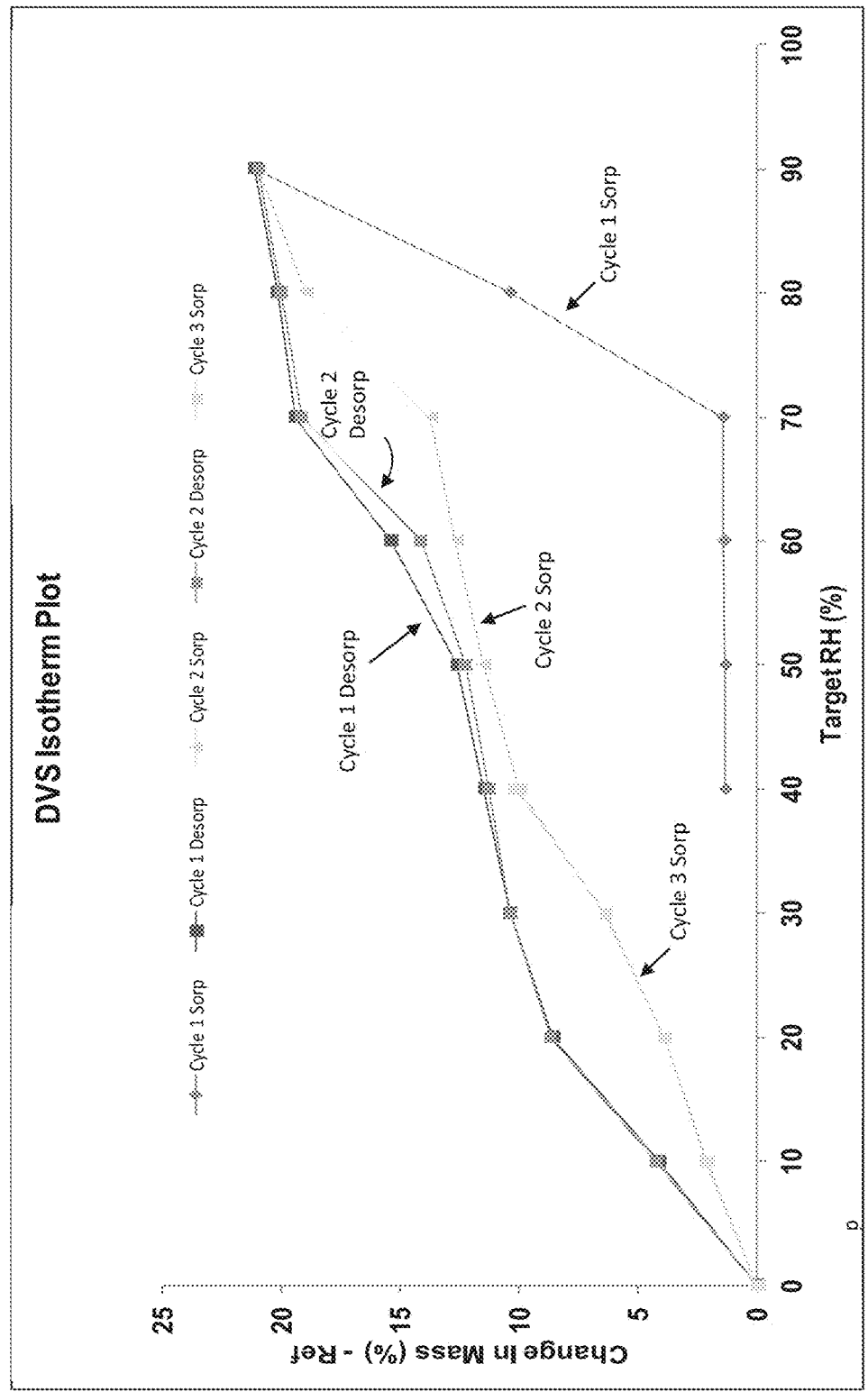
FIGS. 5C and 5D show the results of a DVS plot of polymorph Form 3 and polymorph Form 7, respectively.
Figure 5D:
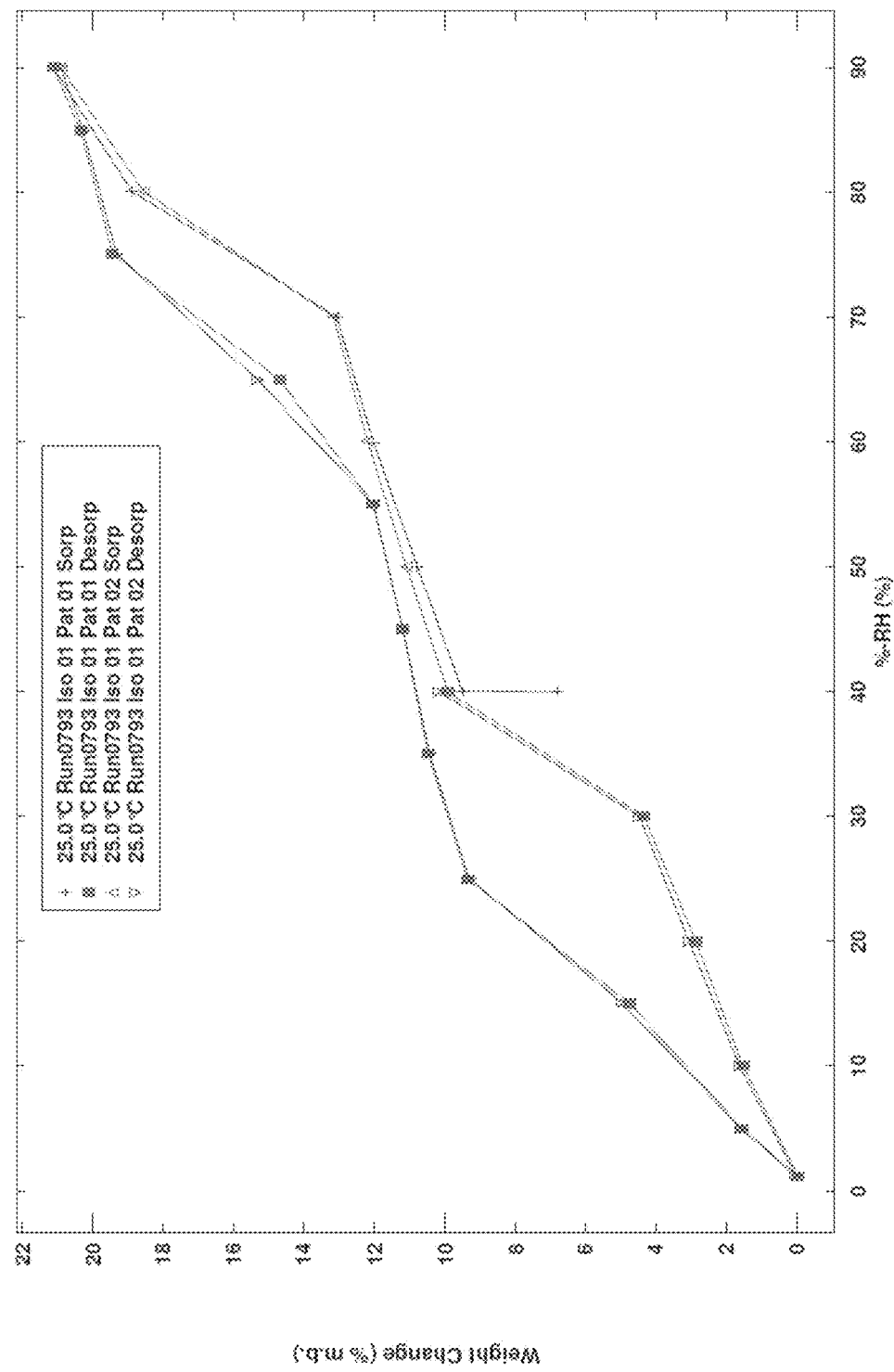

Polymorph Form 3 was not observed to be hygroscopic at 70% RH and below (FIG. 5C). However, Form 3 absorbs up to ~20 wt. % of water up to 90% RH at 25° C. XRPD analysis of the sample after DVS analysis shows that the material had converted to Form 7.

Polymorph Form 7 was observed to be highly hygroscopic (FIG. 5D) picking up ~21 wt. % of water up to 90% RH at 25° C. The form was found to be stable at room temperature between 30-60% RH. However, below this interval the material becomes amorphous. In summary, up to 70% RH, polymorph Form 3 is not hygroscopic and exhibits better stability compared to Form 7.

$^1$H Nuclear Magnetic Resonance (NMR)

NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone.

Figure 13:
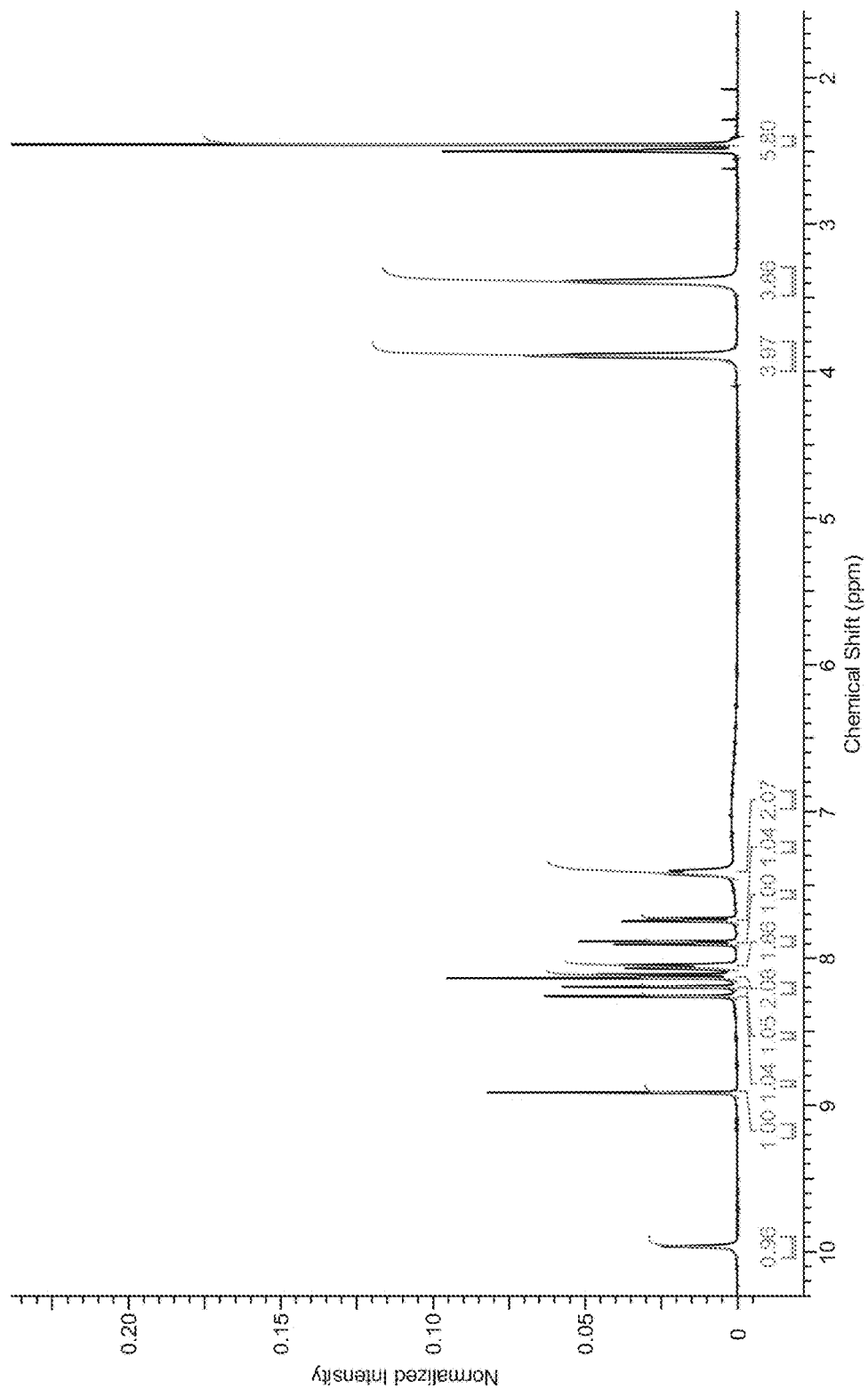
FIG. 13 shows an exemplary proton NMR spectrum of polymorph Form 3.
Figure 14:
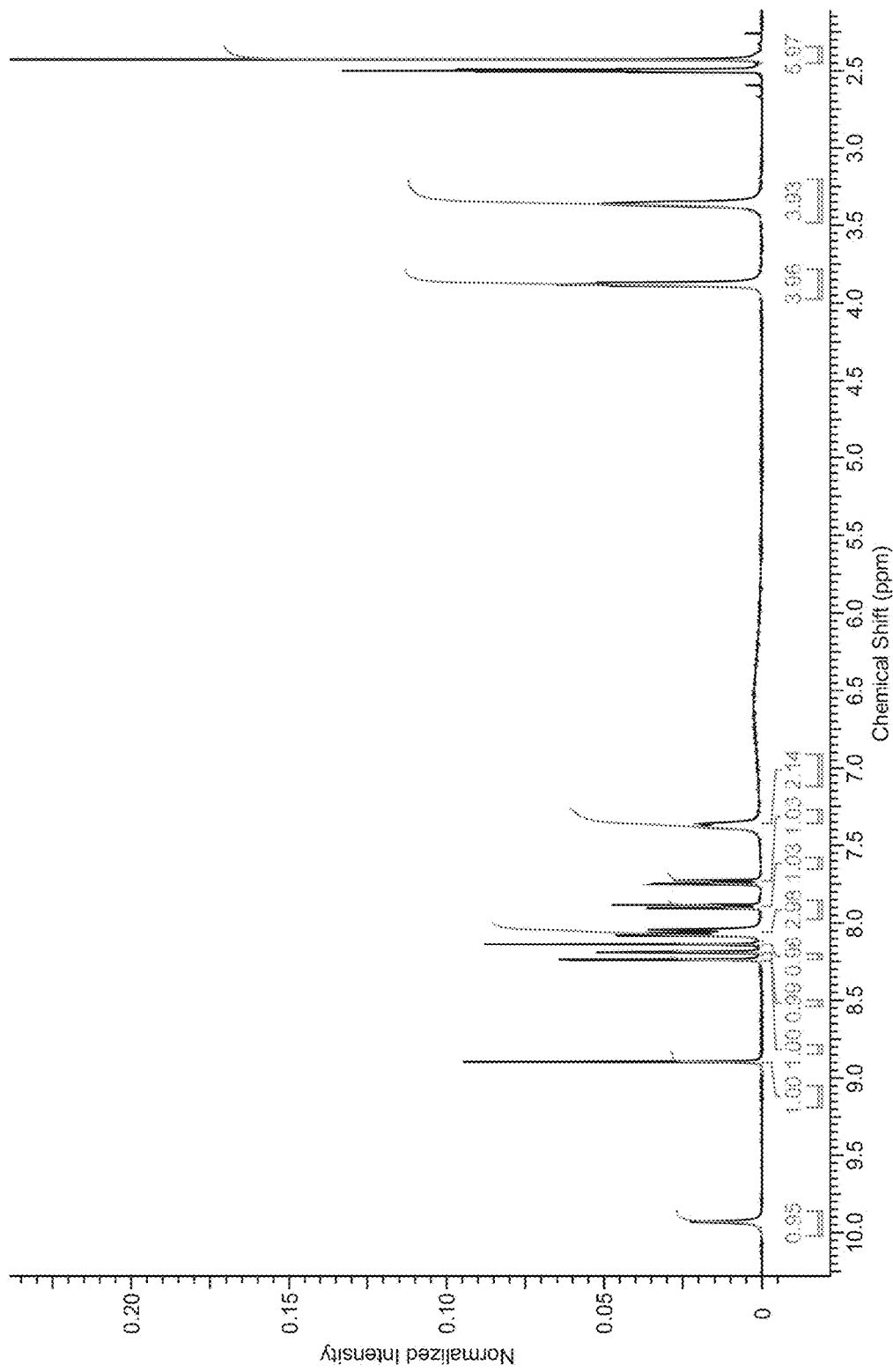
FIG. 14 shows an exemplary proton NMR spectrum of polymorph Form 7.

Samples were prepared in DMSO-$d_6$, unless otherwise stated. Off-line analysis was carried out using ACD Spectrus Processor 2012. FIGS. 13 and 14 are exemplary proton NMR spectra of polymorph Form 3 and polymorph Form 7, respectively.

Example 7: Intrinsic Dissolution Studies of Polymorph Form 3 and a Mono-MSA Salt of a Compound of Formula I This example demonstrates the improved dissolution rate of polymorph Form 3 (i.e., a polymorph of a monohydrate, bis-mesylate salt of a compound of Formula I) compared to a mono-mesylate salt a compound of Formula I.

Intrinsic dissolution rate experiments were conducted using a rotating disk apparatus. Disks of drug substance were prepared by directly compressing 100 mg of powder of polymorph Form 3 in a die at a pressure of 2500 psi for 2 minutes using a hydraulic press (Carver Press, Fred Carver, N.J., USA). The exposed surface area for the resulting disk was 0.5 cm$^2$. A regular USP dissolution apparatus maintained at 37±0.5° C. was used for the dissolution study. Each dissolution vessel contained 500 mL of aqueous dissolution medium of 0.05 N HCl or pH 6.8 20 mM phosphate buffer with 1% cetyltrimetrylammonium bromide (CTAB). The disk holder (die) was half-immersed into the dissolution medium and rotated at 100 rpm. Samples were withdrawn at specified time intervals and analyzed by HPLC.

The dissolution rate (J) of solid per unit surface area may be described by a diffusion model:

$$J = \frac{DA}{h}(C_s - C_b) \quad \text{(Equation 2)}$$

Where D is the diffusion coefficient of the solute, h is the diffusion layer thickness during dissolution at the surface of solid, Cs is the saturation solubility of the solid in the dissolution medium, and Cb is its concentration in the bulk medium. Under sink condition (Cs>>Cb) Equation 2 is reduced to:

$$J = \frac{DA}{h}(C_s) \quad \text{(Equation 3)}$$

where dissolution rate is directly proportional to the saturated solubility.

The intrinsic dissolution rates (IDR) of the free base compound of Formula I, mono-MSA salt of the compound of Formula I, and the polymorph Form 3 (a monohydrate, bis-MSA salt of the compound of Formula I) are summarized in Table 3 below.

TABLE 3

| Physicochemical Properties | Free Base, Compound of Formula I | mono-MSA | polymorph Form 3 (monohydrate, bis-MSA) |
|---|---|---|---|
| Solubility in water (mg/ml) | <0.00005 | 0.08 (final pH 1.6) | >100 (final pH <1.5) |
| Intrinsic dissolution rate in pH 1.3 0.05N HCl with 0.9% NaCl (mg/min/cm$^2$) | 0.00046 | 2.5 | Not determined |
| Intrinsic dissolution rate in pH 6.8 20 mM phosphate with 1% CTAB (mg/min/cm$^2$) | Not determined | 0.003 | 1.2 |

The IDR of the anhydrous crystal form of the free base of Formula I is 0.00046 mg/min/cm$^2$ at pH 1.3. At pH 6.8 the intrinsic dissolution rate could not be determined because no free base was detectable in the dissolution medium.

Figure 7:
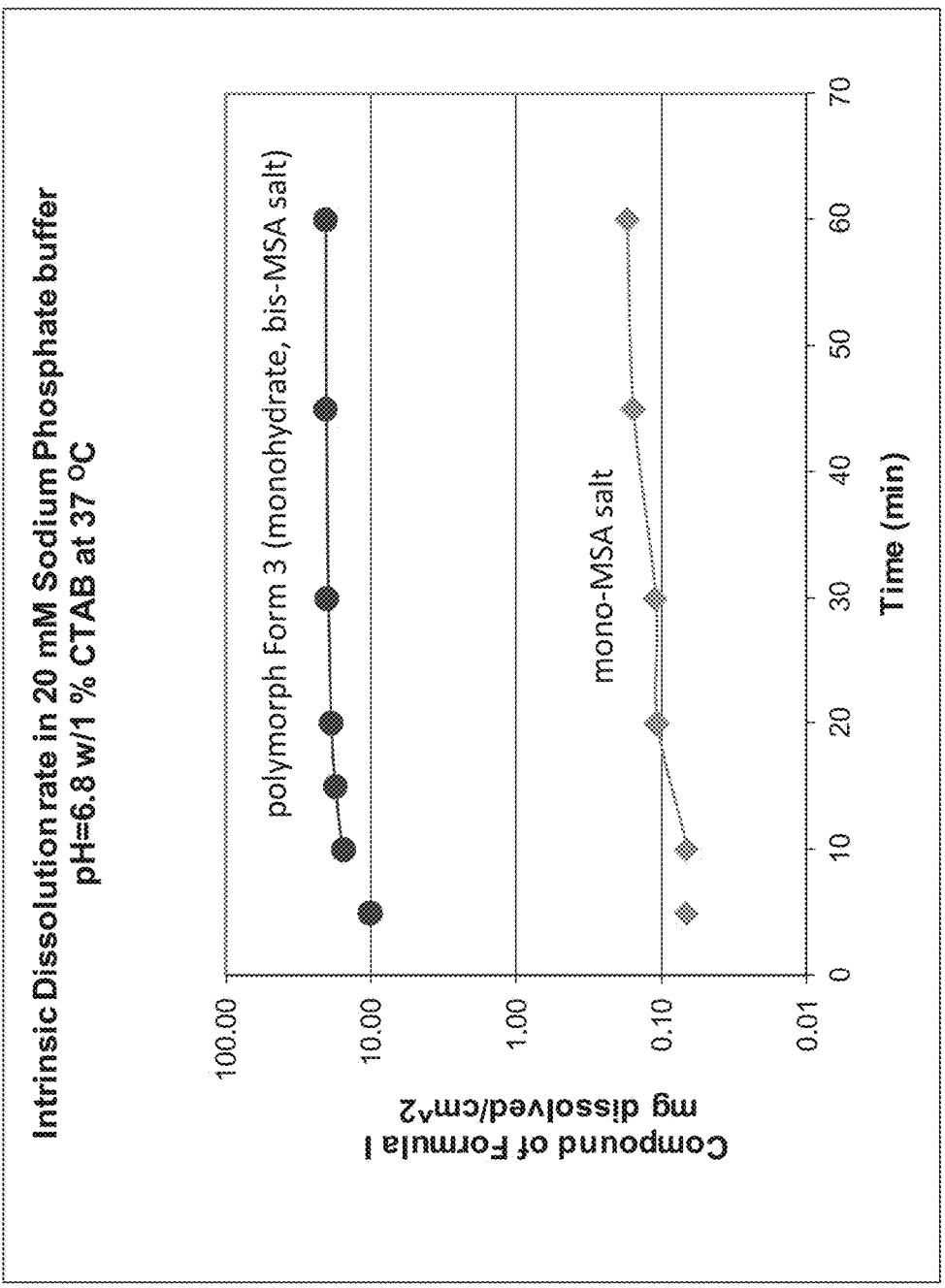
FIG. 7 shows a comparison of dissolution rates between polymorph Form 3 and the mono-mesylate (mono-MSA) salt of a compound of Formula I at pH 6.8.

The IDR of the crystal form of the mono-MSA compound of Formula I showed high pH dependency. From pH 1.3 to 6.8, IDR decreased by about 1000 fold, from 2.5 to 0.003 mg/min/cm$^2$. In contrast, The IDR of the crystal form of polymorph Form 3 showed much higher IDR than the mono-MSA at pH 6.8. At 1.2 mg/min/cm$^2$, the IDR of polymorph Form 3 is 400-fold higher than mono MSA. In addition, FIG. 7 shows a graphical comparison of the dissolution rate of the two compounds at pH 6.8.

Polymorph Form 3 has the unexpected and surprising result of performing significantly better than the mono-MSA compound in increased pH conditions.

Example 8: PK Study in Dog Model

This example demonstrates the pharmacokinetic effects of administering the mono-MSA salt or the bis-MSA salt (polymorph Form 3, which is a polymorph of a monohydrate, bis-MSA salt) of Formula I to pentagastrin- or famotidine-pretreated dogs.

Pentagastrin pretreatment (6 µg/kg intramuscular injection 30 minutes prior to test formulation dosing) in fasted dogs was used to simulate fasting gastric pH in humans. Famotidine pretreatment (20 mg orally 1 hour prior to test formulation dosing) in fasted dogs was used to simulate human gastric pH when acid suppressant was co-dosed with test formulation. The tablets of the mono-MSA salt or bis-MSA salt of a compound of Formula I (conventional tablet and spray dried formulation) were orally administered followed by a 30 mL water flush.

The exposure of the compound of Formula I in dogs dosed with tablets containing the mono-MSA salt form is highly dependent on gastric pH. As shown in Table 2, the area under the curve for 24 hours after dosing (AUC$_{0-24}$) decreased by more than 100-fold in famotidine-pretreated dogs compared to the AUC$_{0-24}$ in pentagastrin-pretreated dogs. These results are consistent with the kinetic solubility profile of mono-MSA salt of a compound of Formula I, where solubility decreases dramatically as pH increases from 2 to 3.

Figure 8:
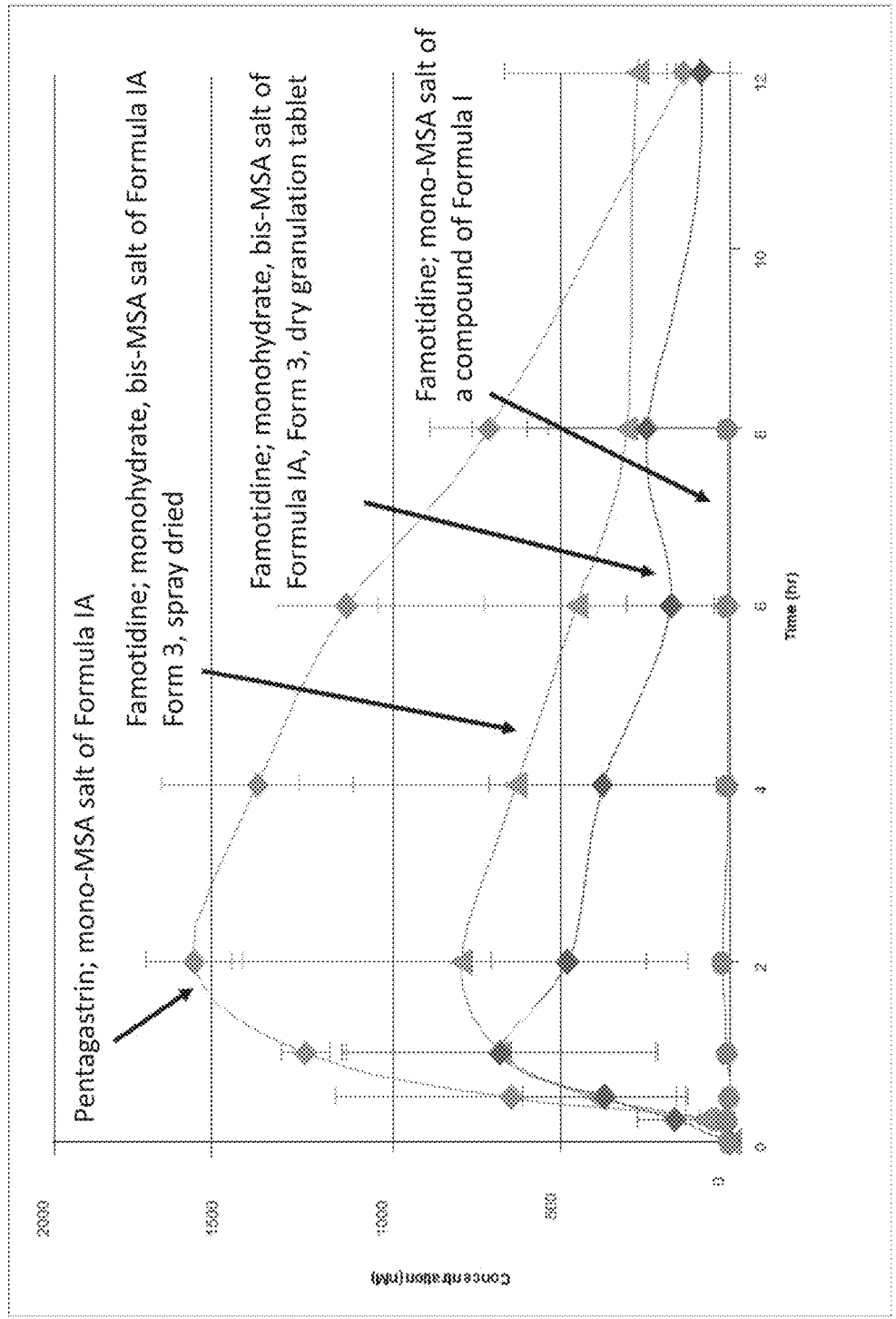
FIG. 8 shows a plot summarizing the results of a PK study of mono- and bis-MSA salt form in dogs that have been pretreated with either pentagastrin or famotidine (an acid suppressant).

When a similar tablet formulation containing Form 3 was dosed in the famotidine-pretreated dogs, the AUC$_{0-24}$ unexpectedly increased by more than 10-fold compared to the mono-MSA salt formulation. A spray-dried formulation provides even further increases in oral bioavailability over the conventional tablet formulation. These surprising and unexpected results show improved bioavailability and suggest that use of Form 3 reduces drug-drug interactions with acid suppressants, compared to the mono-mesylate salt. A graphical representation of the results is shown in FIG. 8.

TABLE 4

| Dog pre-treatment | Compound of Formula I | F (%) Mean | $AUC_{0-24}$ (μM hr) Mean | $AUC_{0-24}$ (μM hr) SD | $C_{max}$ (μM) Mean | $C_{max}$ (μM) SD | $T_{max}$ (hr) Mean | $T_{max}$ (hr) SD |
|---|---|---|---|---|---|---|---|---|
| pentagastrin | mono-MSA salt, conventional tablet, 100 mg 20% drug load (clinical) | 34 | 11 | 1.8 | 1.6 | 0.2 | 2.4 | 1.2 |
| famotidine | | 0.2 | 0.06 | 0.01 | 0.02 | 0.002 | 1.7 | 0.6 |
| pentagastrin | Form 3 (monohydrate, bis-MSA salt), conventional tablet, 100 mg 20% drug load | 13 | 4.1 | 1.4 | 0.8 | 0.2 | 1.8 | 0.4 |
| famotidine | | 15 | 4.9 | 4.2 | 0.7 | 0.5 | 4.9 | 9.4 |
| pentagastrin | Form 3 (monohydrate, bis-MSA salt), 100 mg, spray dried tablet 20% drug load | 18 | 6.1 | 1.8 | 1.1 | 0.1 | 2.3 | 0.8 |
| famotidine | | 20 | 6.4 | 7.8 | 0.8 | 0.5 | 1.7 | 0.5 |

Example 9: Alternative Method of Obtaining Polymorph Form 3

This example describes an alternative method of obtaining polymorph Form 3, wherein the method does not comprise adding seeds of Form 3. Polymorph Form 3 is a polymorph of a monohydrate, bis-mesylate salt of a compound of Formula I (and may also be described is a polymorph of a monohydrate of the compound of Formula IA shown in the reaction scheme below).

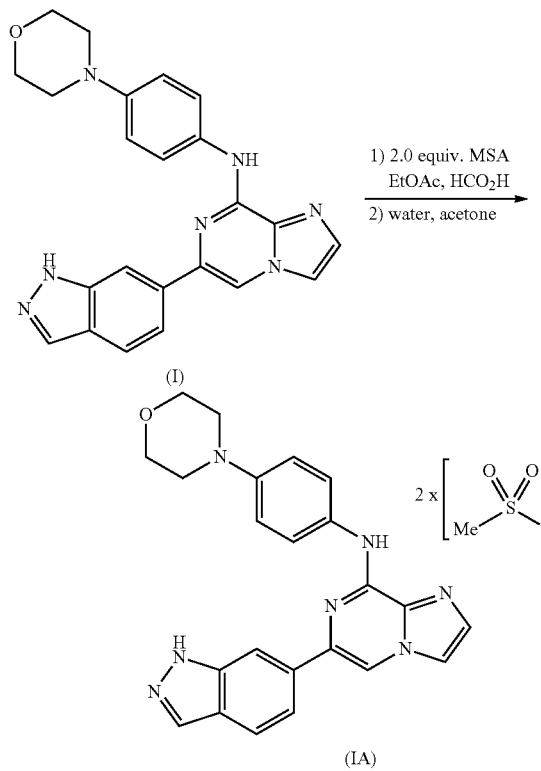

Formic acid (3V, 3.6×) and ethyl acetate (2V, 1.8×) were added to Reactor A and adjusted to 19-25° C. The compound of Formula I (1.0×) was added to Reactor A while maintaining the reactor temperature at 19-25° C., and mixed until the solids dissolved. The solution in Reactor A was transferred to Reactor B. Formic acid (0.08V, 0.1×), ethyl acetate (2V, 1.8×), and methanesulfonic acid (2.0 mol equiv., 0.47×) were added to Reactor A. The solution in Reactor A was transferred to Reactor B while maintaining a temperature of 19-25° C. in Reactor B. Ethyl acetate (5V, 4.5×) was added to Reactor A and then to Reactor B over a minimum of 1 hour. The contents of Reactor B were agitated for about 16 h at 19-25° C., then filtered rinsed with ethyl acetate (4V, 3.6×) and dried under vacuum at 60° C.

The solids were transferred to Reactor A along with acetone (18.9V, 15.0×) and water (0.5V, 0.5×). The pump and lines were rinsed forward to Reactor A with acetone (0.9V, 0.7×). The contents of Reactor A were mixed at 19-25° C. The conversion was monitored by XRPD analysis. The reaction mixture was filtered, rinsed with acetone (3V, 2.4×) and dried under vacuum at 60° C. to obtain polymorph Form 3.

Example 10: Synthesis of Polymorph Form 3

This example describes a method of obtaining polymorph Form 3, which is a polymorph of a monohydrate, bis-mesylate salt of a compound of Formula I as depicted in the reaction scheme below.

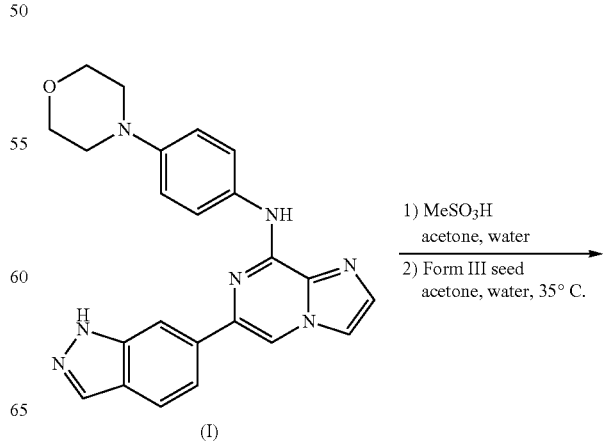

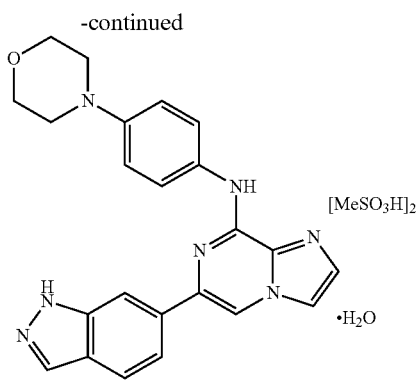

A mixture of methanesulfonic acid (0.56×) and water (0.5×) were added to a mixture of compound of formula I (1.0×), acetone (3.6×) and water (4.0×) while maintaining a content temperature of below about 35° C. until solids dissolved. The solution was agitated for about 10 minutes and the content temperature was adjusted to about 19 to 25° C. Under high agitation, acetone (11.9×) was added over about 2 h. After this period, the content temperature was adjusted to about 0 to 6° C. The mixture was agitated for at least about 5 h, filtered and the filter cake was rinsed with acetone (4.0×). The wet cake was dried under vacuum at a maximum of about 60° C.

The dried solids were transferred back to a reaction vessel and acetone (15.0×), water (0.5×) and acetone (0.4×) were sequentially added. Polymorph Form 3 seeds (0.0147×, 1 mol %) were added and the contents were adjusted to about 32 to 38° C., and agitated until Form 7 to Form 3 conversion was deemed complete by XRD (about 24 to 60 h). The slurry was cooled to about 19 to 25° C. and filtered. The filter cake was rinsed with acetone (2.4×). The wet cake was dried under vacuum at a maximum of about 60° C.

Example 11: Single Crystal X-Ray Structure of Polymorph Form 3

This example describes the single crystal X-ray structure of polymorph Form 3 of a monohydrate, bis-mesylate salt of a compound of Formula I.

Figure 9:
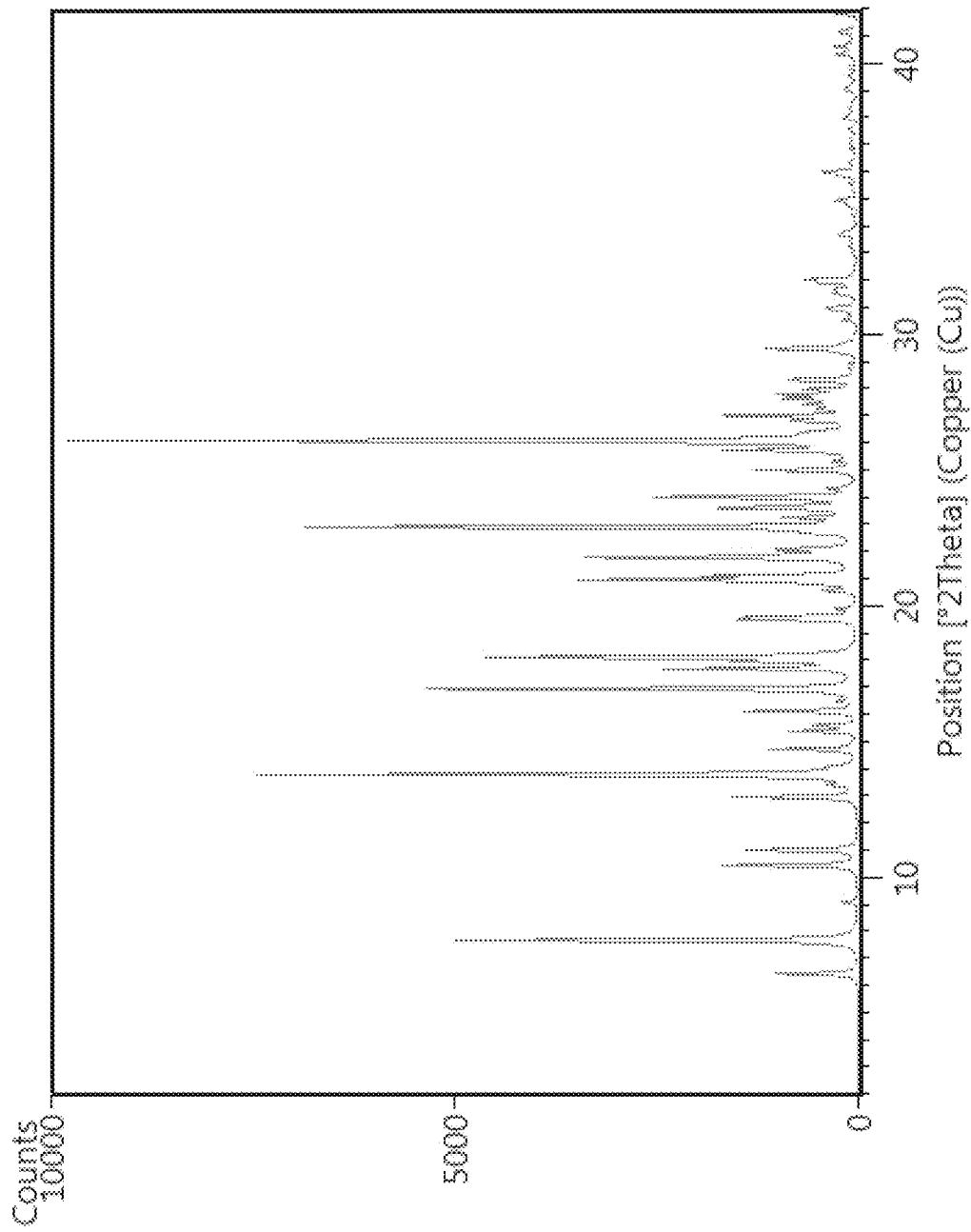
FIG. 9 shows a simulated XRPD pattern of polymorph Form 3.
Figure 10A:
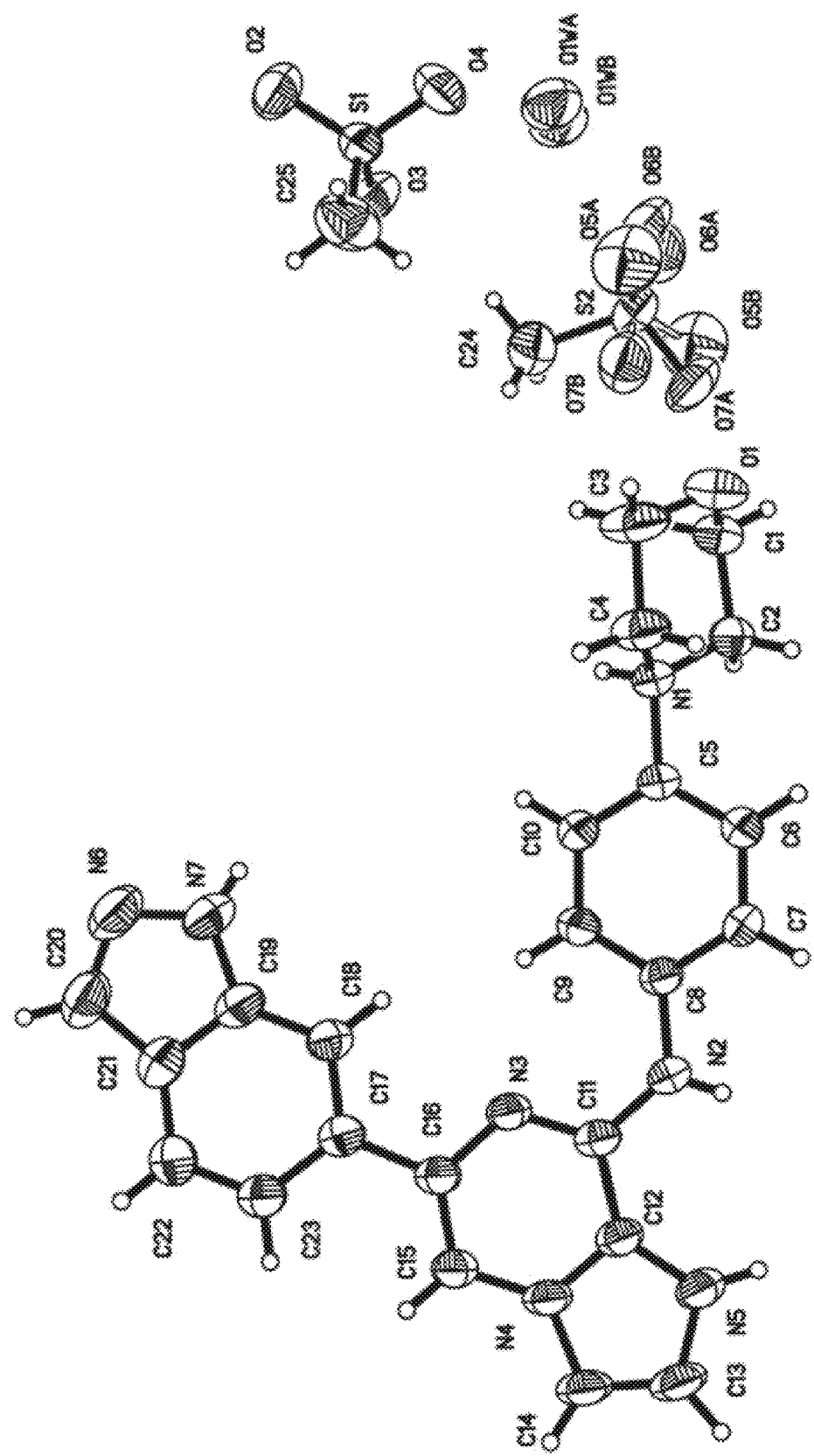
FIG. 10A shows a view of polymorph Form 3 from the crystal structure showing the numbering scheme employed.
Figure 10B:
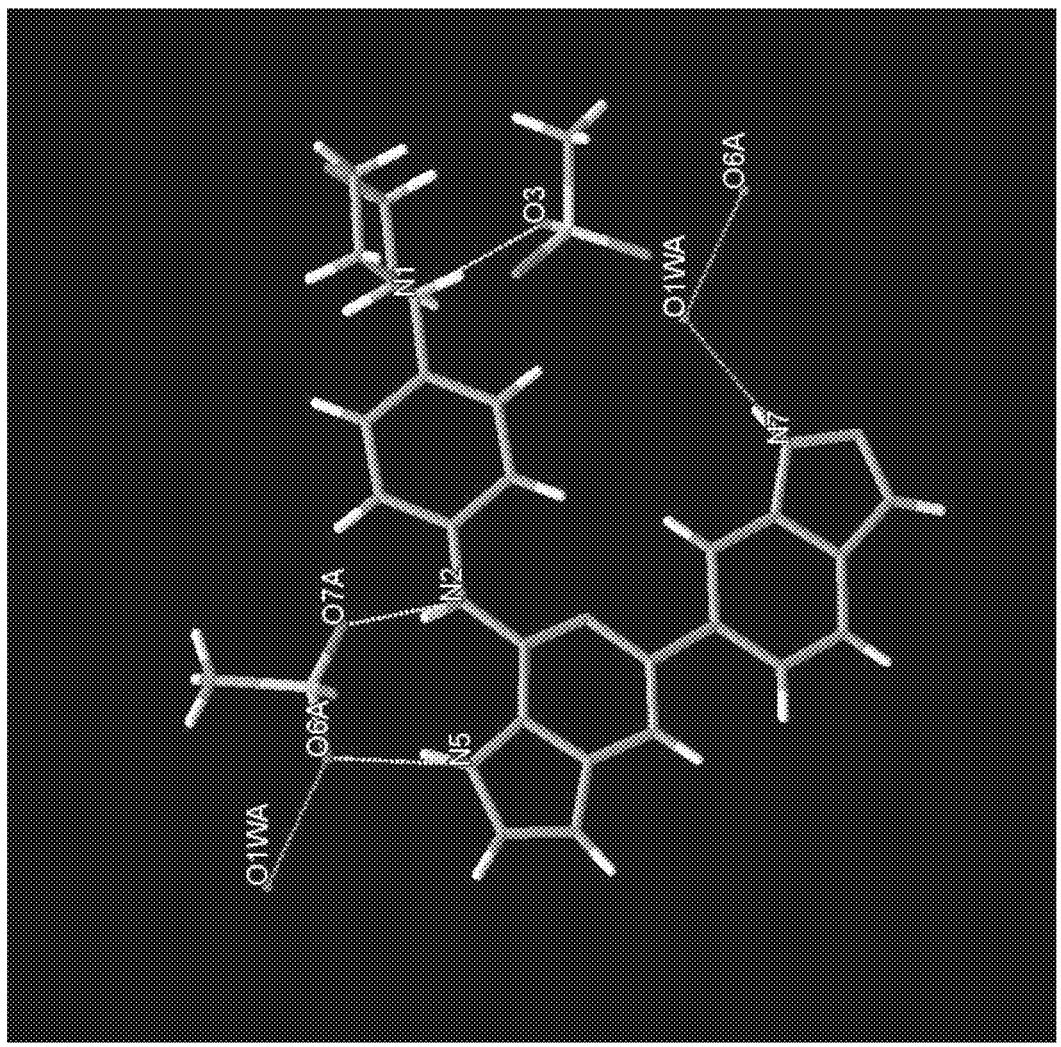
FIG. 10B illustrates the hydrogen bonding interactions of polymorph Form 3.
Figure 11:
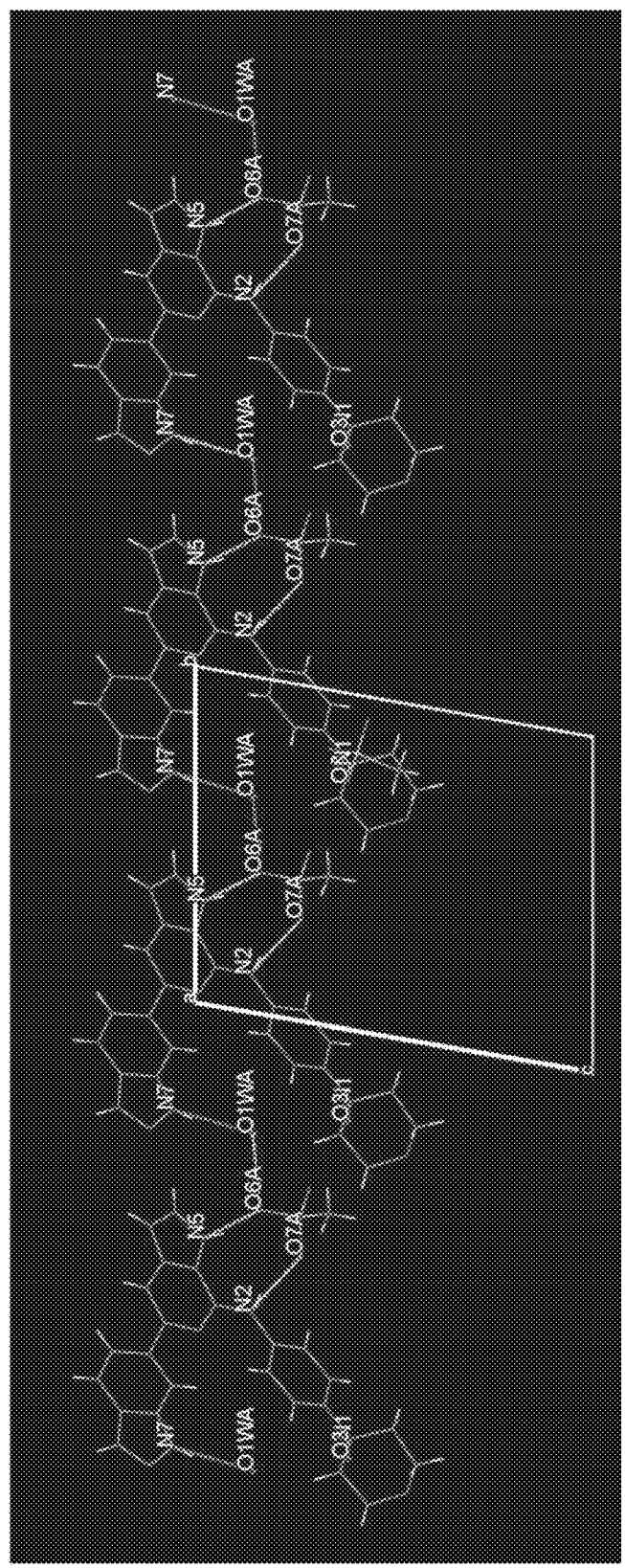
FIG. 11 illustrates the infinite chains of polymorph Form 3, mesylate and ovate molecules viewed down the crystallographic a axis.
Figure 12:
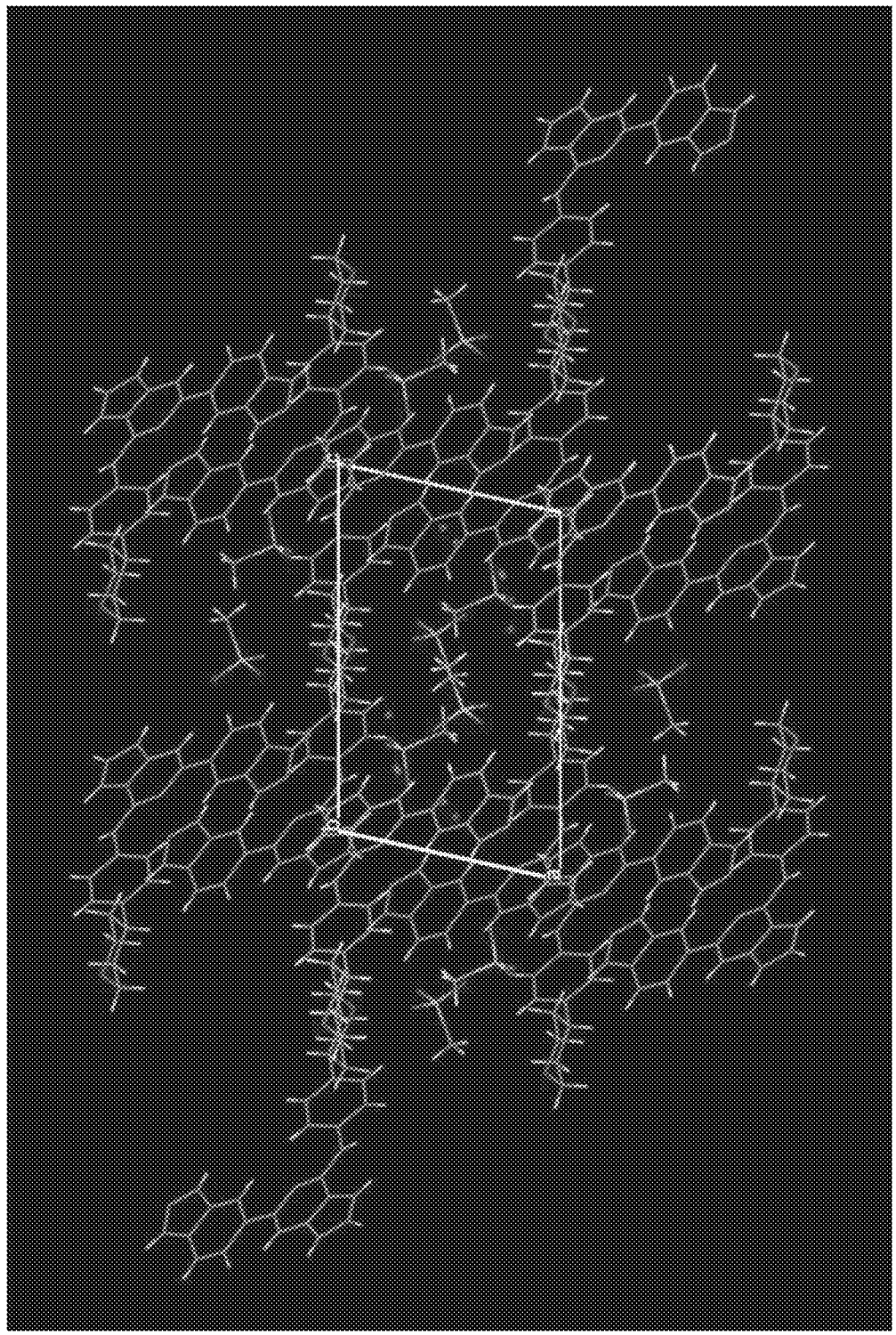
FIG. 12 illustrates the packing of polymorph Form 3 down the crystallographic b axis.

The single crystal X-ray structure of polymorph Form 3 was determined at RT in the triclinic system, space group P-1. There was one cation of the compound of Formula I, 2 mesylate anions and one water molecule in the asymmetric unit and the final R1 [I>2σ(I)]=4.53%. An XRPD pattern was calculated from the crystal structure to serve as a reference for this form (FIG. 9).

Structural Features

A crystal of sufficient size and quality for analysis by single crystal X-ray diffraction was obtained by maturation between 50° C. and RT on an eight hour cycle in isopropyl acetate. The crystal was of block morphology with approximate dimensions 0.50×0.22×0.15 mm.

The structure of polymorph Form 3 was been determined as depicted in FIGS. 10A, 10B, 11 and 12. Table 5 below summarizes the sample and crystal data for polymorph Form 3.

TABLE 5

| Crystallization method | Maturation between RT and 50° C. |
|---|---|
| Empirical formula | $C_{25}H_{31}N_7OS_2$ |
| Formula weight | 621.69 |
| Temperature | 298(2) K |
| Wavelength | 1.54178 Å |
| Crystal size | 0.500 × 0.220 × 0.150 mm |
| Crystal habit | Colourless Column |
| Crystal system | Triclinic |
| Space group | P-1 |
| Unit cell dimensions | a = 8.7831(6) Å   α = 98.108(6)° |
| | b = 11.8484(8) Å   β = 100.955(6)° |
| | c = 14.2485(10) Å   γ = 98.861(6)° |
| Volume | 1416.05(17) Å$^3$ |
| Z | 2 |
| Density (calculated) | 1.458 Mg/m$^3$ |
| Absorption coefficient | 2.239 mm$^{-1}$ |
| F(000)2 | 652 |

Example 12: Alternative Synthetic Route for Polymorph Form 3 Via Mono-MSA Intermediate This example provides a description of the synthesis of polymorph Form 3 (which is a polymorph of a monohydrate, bis-MSA salt of a compound of Formula I) from a mono-MSA salt of a compound of Formula I.

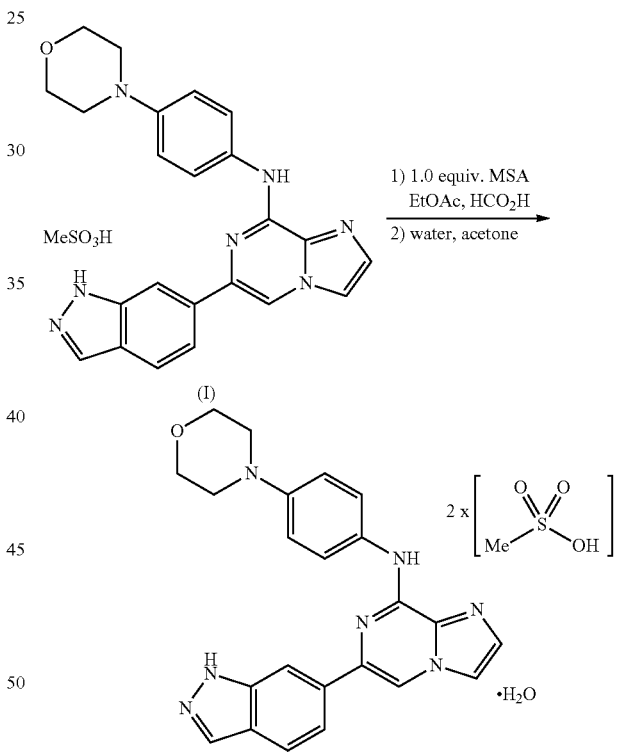

Formic acid (3.7×) is charged to a reaction vessel and combined with ethyl acetate (9.7×). The contents are agitated and adjusted to about 19 to 25° C. The mono-MSA compound of Formula I (1.0×) is charged portion-wise while maintaining the content temperature at about 19 to 25° C. The contents are agitated at about 19 to 25° C. until all solids dissolve.

To the above contents is added a solution of ethyl acetate (0.6×) and methanesulfonic acid (0.169×, corrected for MSA content and water present in the mono-MSA compound) prepared in a separate reaction vessel. The resulting mixture is agitated at about 19 to 25° C. for about 24 h. The reaction mixture is sampled and tested for MSA content by ion chromatography. Agitation is continued until the desired range of MSA content is achieved. Upon reaction completion, the contents of the reaction vessel are filtered, rinsed with ethyl acetate (3.6×) and the wet filter cake is dried under vacuum at about 60° C. The dried solids are transferred back to the reaction vessel.

To the dried solids was added acetone (15.0×) and the resulting mixture is put under maximum agitation. Water (0.50×) is added followed by acetone (0.70×). The mixture is agitated at about 19 to 25° C. until the form conversion to polymorph Form 3 is complete as confirmed by XRPD analysis. The solids are filtered, rinsed with acetone (2.4×), and the wet cake is dried under vacuum at about 60° C.

Throughout this specification, various patents, patent applications and other types of publications (e.g., journal articles) are referenced. The disclosure of all patents, patent applications, and publications cited herein are hereby incorporated by reference in their entirety for all purposes.

What is claimed is:

1. A method of producing polymorph Form 3 of a monohydrate, bis-mesylate salt of a compound of Formula I:

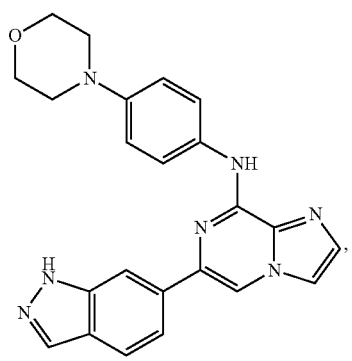

comprising:
adding an amount of polymorph Form 3 of a monohydrate, bis-mesylate salt of a compound of Formula I seeds and a solvent to polymorph Form 7 of a hydrate, bis-mesylate salt of a compound of Formula I to form a mixture; and
producing polymorph Form 3 of a monohydrate, bis-mesylate salt of a compound of Formula I in the mixture,
wherein the polymorph Form 3 of a monohydrate, bis-mesylate salt of a compound of Formula I has an X-ray diffraction pattern comprising 2θ-reflections, plus or minus 0.2 degrees 2θ, selected from the group consisting of A: 13.8, 16.9, 22.9, and 26.1; B: 7.7, 12.9, 17.7, and 18.1; and C: 7.7, 12.9, 13.8, 16.9, 17.7, 18.1, 22.9, and 26.1; and
wherein the polymorph Form 7 of a hydrate, bis-mesylate salt of a compound of Formula I has an X-ray diffraction pattern comprising 2θ-reflections, plus or minus 0.2 degrees 2θ, selected from the group consisting of A: 4.9, 9.8, and 26.7; B: 15.0 and 18.0; and C: 4.9, 9.8, 15.0, 18.0, and 26.7.

2. A method of treating a cancer in a human in need thereof, comprising administering to the human a therapeutically effective amount of a monohydrate of a bis-mesylate salt of a compound of Formula I:

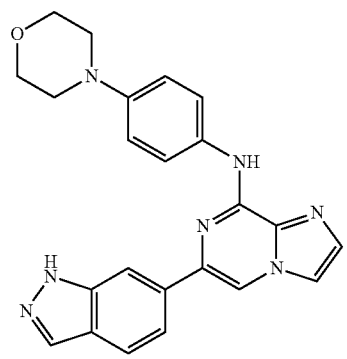

wherein the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantel cell lymphoma (MCL), follicular lymphoma (FL), Waldestrom's macroglobulinemia (WM), T-cell lymphoma, B-cell lymphoma, diffuse large B-cell lymphoma (DLBCL), lymphoplasmacytic lymphoma (LPL), or marginal zone lymphoma (MZL); and further wherein the monohydrate of the bis-mesylate salt is a polymorph characterized by an X-ray diffraction pattern comprising 2θ-reflections, plus or minus 0.2 degrees 2θ, at 13.8, 16.9, 22.9, and 26.1.

3. The method of claim 2, wherein the cancer is acute lymphocytic leukemia (ALL).

4. The method of claim 2, wherein the cancer is acute myeloid leukemia (AML).

5. The method of claim 2, wherein the cancer is chronic lymphocytic leukemia (CLL).

6. The method of claim 2, wherein the cancer is small lymphocytic lymphoma (SLL).

7. The method of claim 2, wherein the cancer is myelodysplastic syndrome (MDS).

8. The method of claim 2, wherein the cancer is myeloproliferative disease (MPD).

9. The method of claim 2, wherein the cancer is chronic myeloid leukemia (CML).

10. The method of claim 2, wherein the cancer is multiple myeloma (MM).

11. The method of claim 2, wherein the cancer is non-Hodgkin's lymphoma (NHL).

12. The method of claim 2, wherein the cancer is mantel cell lymphoma (MCL).

13. The method of claim 2, wherein the cancer is follicular lymphoma (FL).

14. The method of claim 2, wherein the cancer is Waldestrom's macroglobulinemia (WM).

15. The method of claim 2, wherein the cancer is T-cell lymphoma.

16. The method of claim 2, wherein the cancer is B-cell lymphoma.

17. The method of claim 2, wherein the cancer is diffuse large B-cell lymphoma (DLBCL).

18. The method of claim 2, wherein the cancer is lymphoplasmacytic lymphoma (LPL).

19. The method of claim 2, wherein the cancer is marginal zone lymphoma (MZL).

* * * * *